(12) United States Patent
Utsunomiya et al.

(10) Patent No.: US 9,710,920 B2
(45) Date of Patent: Jul. 18, 2017

(54) MOTION INFORMATION PROCESSING DEVICE

(71) Applicant: Toshiba Medical Systems Corporation, Otawara-shi (JP)

(72) Inventors: Kazuki Utsunomiya, Nasushiobara (JP); Masashi Yoshida, Nasushiobara (JP); Hayato Konishi, Sakura (JP); Shigeyuki Ishii, Nasushiobara (JP); Kousuke Sakaue, Nasushiobara (JP); Satoshi Ikeda, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 40 days.

(21) Appl. No.: 14/793,396

(22) Filed: Jul. 7, 2015

(65) Prior Publication Data

US 2015/0310629 A1    Oct. 29, 2015

Related U.S. Application Data

(63) Continuation of application No. PCT/JP2014/051023, filed on Jan. 20, 2014.

(30) Foreign Application Priority Data

Jan. 18, 2013 (JP) ................................. 2013-007872
Aug. 12, 2013 (JP) ................................. 2013-167836
Aug. 21, 2013 (JP) ................................. 2013-171755

(51) Int. Cl.
*G06K 9/00* (2006.01)
*G06T 7/20* (2017.01)
(Continued)

(52) U.S. Cl.
CPC .............. *G06T 7/2033* (2013.01); *A61B 5/11* (2013.01); *A61B 5/112* (2013.01);
(Continued)

(58) Field of Classification Search
CPC ................ G06K 9/00; A61B 5/00; G06T 7/00
(Continued)

(56) References Cited

U.S. PATENT DOCUMENTS 5,997,439 A * 12/1999 Ohsuga .............. A63B 71/0622
                                                           434/247
8,736,682 B2 * 5/2014 Sukenori ................ H04N 5/262
                                                           348/169
9,128,526 B2 * 9/2015 Homma .................. G06F 3/017

FOREIGN PATENT DOCUMENTS

JP     09-056697 A     3/1997
JP     2010-172394 A   8/2010

OTHER PUBLICATIONS

International Search Report mailed Apr. 28, 2014 for PCT/JP2014/051023 filed Jan. 20, 2014 with English Translation.
(Continued)

*Primary Examiner* — Abolfazl Tabatabai
(74) *Attorney, Agent, or Firm* — Oblon, McClelland, Maier & Neustadt, L.L.P.

(57) ABSTRACT

A motion information processing device for supporting a rehabilitation according to an embodiment includes obtaining circuitry and specification circuitry. The obtaining circuitry obtains image information of a subject carrying out a predetermined motion in the rehabilitation and surroundings of the subject. The specification circuitry specifies motion information of the subject carrying out the predetermined motion on the basis of a predetermined feature in the image information obtained by the obtaining circuitry.

25 Claims, 46 Drawing Sheets

(51) Int. Cl.
*A61B 5/11* (2006.01)
*G06Q 10/06* (2012.01)
*G06Q 50/22* (2012.01)
*G09B 19/00* (2006.01)
*G06K 9/44* (2006.01)
*G06T 7/246* (2017.01)
*H04N 7/18* (2006.01)
*A61B 5/103* (2006.01)

(52) U.S. Cl.
CPC ..... *G06K 9/00342* (2013.01); *G06K 9/00348* (2013.01); *G06K 9/44* (2013.01); *G06Q 10/063* (2013.01); *G06Q 50/22* (2013.01); *G06T 7/246* (2017.01); *G06T 7/251* (2017.01); *G09B 19/003* (2013.01); *G06K 2209/055* (2013.01); *G06T 2207/30196* (2013.01); *G06T 2207/30204* (2013.01)

(58) Field of Classification Search
USPC ......... 382/107, 236; 348/14.1, 97, 154, 155, 348/169, 208.1, 407.1; 600/595
See application file for complete search history.

(56) References Cited

OTHER PUBLICATIONS

International Written Opinion mailed Apr. 28, 2014 for PCT/JP2014/051023 filed Jan. 20, 2014.

\* cited by examiner

FIG.3

| JOINT IDENTIFICATION INFORMATION | COORDINATE INFORMATION |
|---|---|
| 2a | (x1, y1, z1) |
| 2b | (x2, y2, z2) |
| 2c | (x3, y3, z3) |
| 2d | (x4, y4, z4) |
| 2e | (x5, y5, z5) |
| 2f | (x6, y6, z6) |
| 2g | (x7, y7, z7) |
| 2h | (x8, y8, z8) |
| 2i | (x9, y9, z9) |
| 2j | (x10, y10, z10) |
| 2k | (x11, y11, z11) |
| 2l | (x12, y12, z12) |
| 2m | (x13, y13, z13) |
| 2n | (x14, y14, z14) |
| 2o | (x15, y15, z15) |
| 2p | (x16, y16, z16) |
| 2q | (x17, y17, z17) |
| 2r | (x18, y18, z18) |
| 2s | (x19, y19, z19) |
| 2t | (x20, y20, z20) |

FIG.7

| NAME | NAME NUMBER | DATE | MOTION INFORMATION | | | |
|---|---|---|---|---|---|---|
| | | | COLOR IMAGE INFORMATION | DISTANCE IMAGE INFORMATION | SPEECH RECOG-NITION RESULT | SKELETON INFORMATION |
| A | 1 | 20120801_1 | COLOR IMAGE INFORMATION | DISTANCE IMAGE INFORMATION | SPEECH RECOG-NITION RESULT | SKELETON INFORMATION |
| | | 20120801_2 | COLOR IMAGE INFORMATION | DISTANCE IMAGE INFORMATION | SPEECH RECOG-NITION RESULT | SKELETON INFORMATION |
| | | 20120802_1 | COLOR IMAGE INFORMATION | DISTANCE IMAGE INFORMATION | SPEECH RECOG-NITION RESULT | SKELETON INFORMATION |
| | | . | . | . | . | . |
| | | . | . | . | . | . |
| B | 2 | 20120803_1 | COLOR IMAGE INFORMATION | DISTANCE IMAGE INFORMATION | SPEECH RECOG-NITION RESULT | SKELETON INFORMATION |
| | | 20120804_1 | COLOR IMAGE INFORMATION | DISTANCE IMAGE INFORMATION | SPEECH RECOG-NITION RESULT | SKELETON INFORMATION |
| | | 20120805_1 | COLOR IMAGE INFORMATION | DISTANCE IMAGE INFORMATION | SPEECH RECOG-NITION RESULT | SKELETON INFORMATION |
| | | . | . | . | . | . |
| | | . | . | . | . | . |
| . | . | | | | | |
| . | . | | | | | |

FIG.11A

| PART | RANGE |
|---|---|
| HEIGHT [cm] | 100 cm TO 200 cm |
| ARM LENGTH [cm] | 60 cm TO 80 cm |
| ... | ... |

FIG.11B

| PART | AVERAGE | VARIANCE |
|---|---|---|
| SHOULDER LENGTH [cm] | 60 cm | 1σ |
| LENGTH FROM HEAD TO WAIST [cm] | 85 cm | 2σ |
| LEFT ARM ANGLE | 80° | 4σ |
| ... | ... | ... |

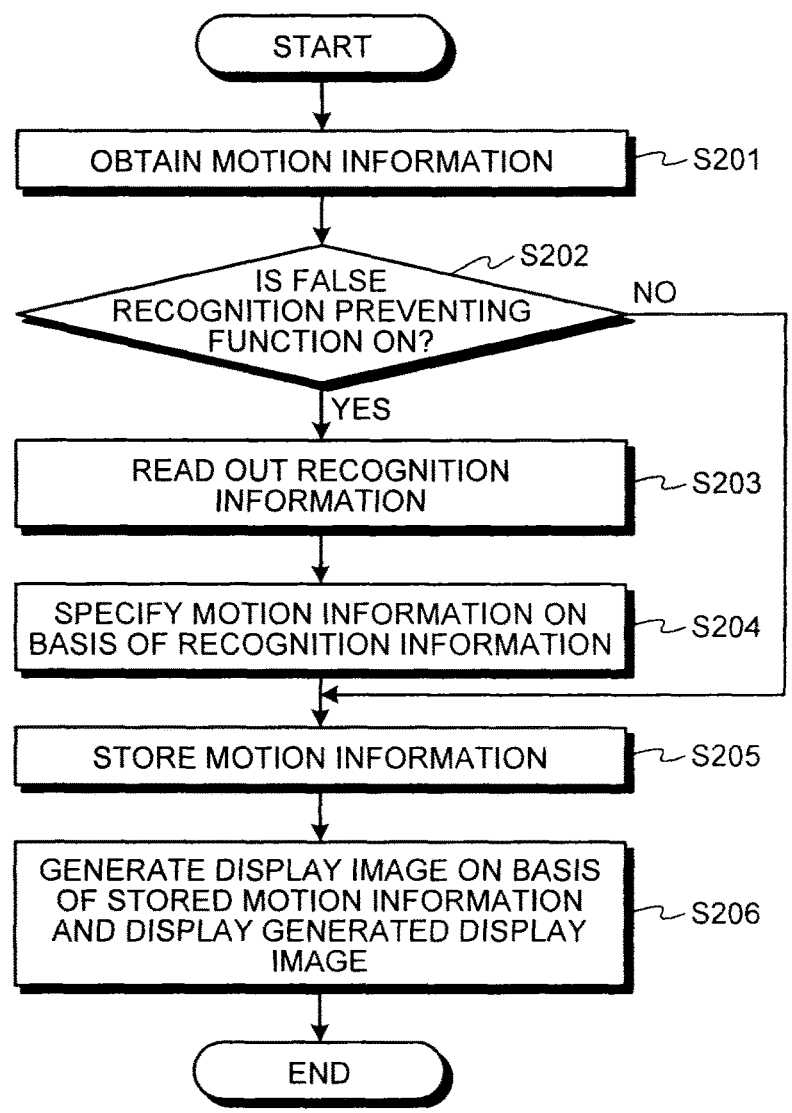

FIG.15
(A)
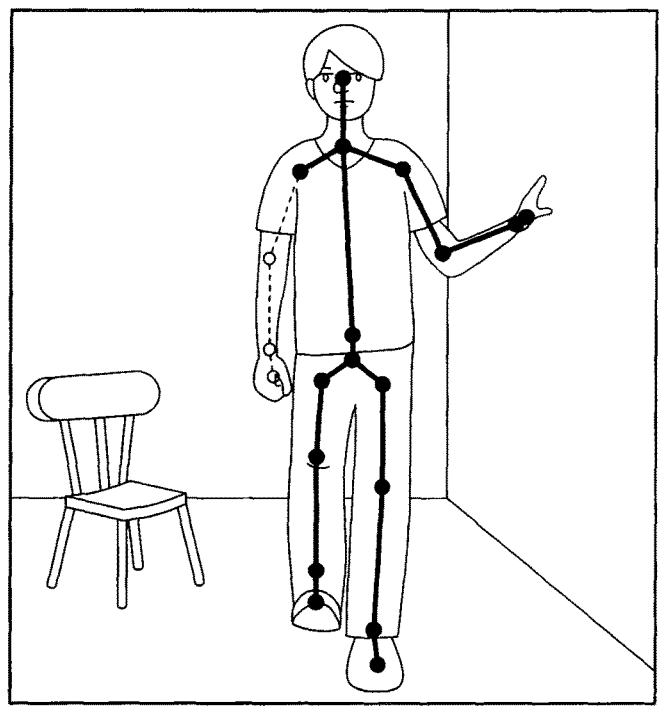
(B)
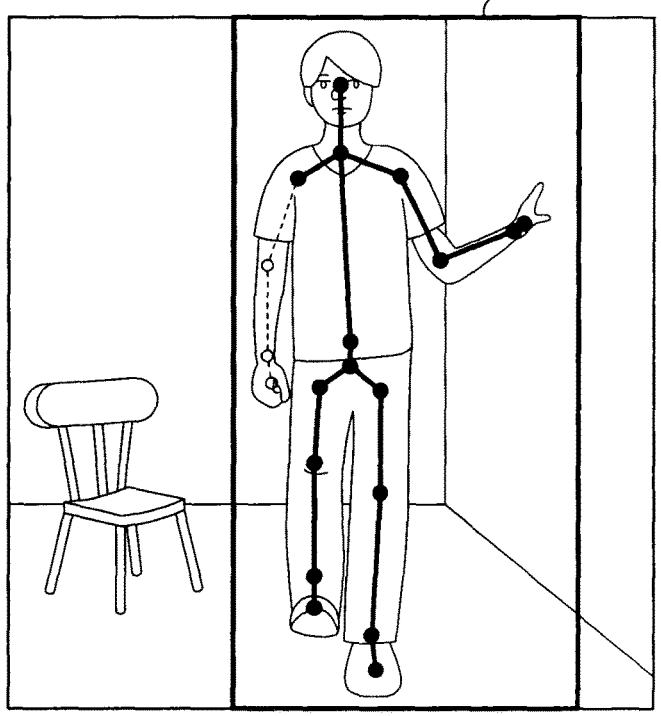

FIG.16
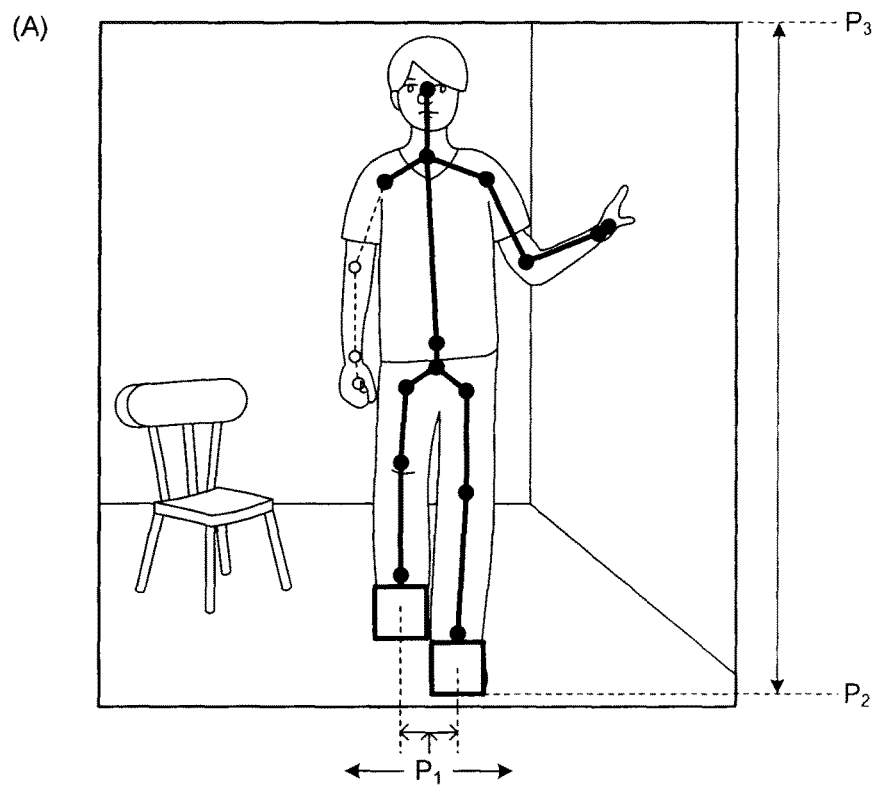
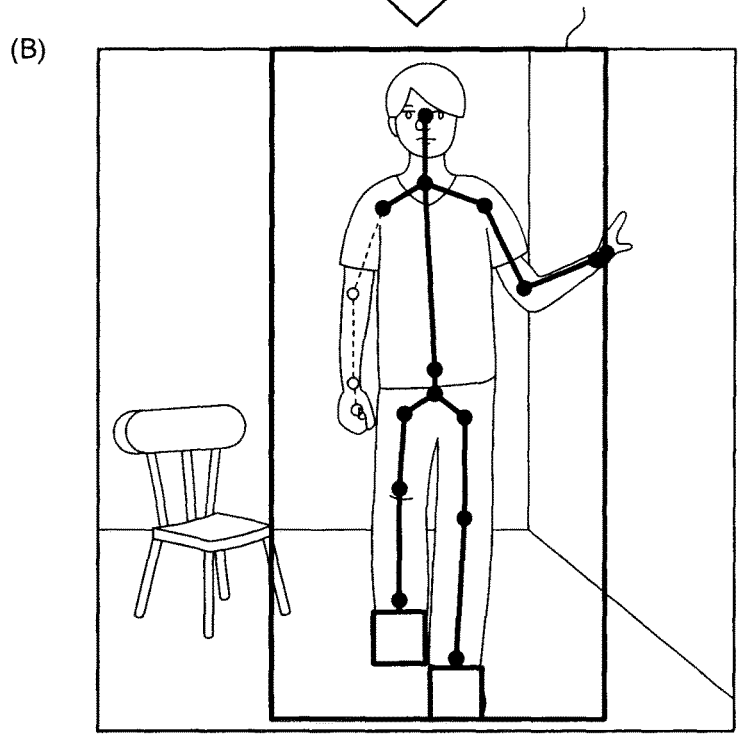

FIG.17
(A) T-SECOND (REFERENCE VALUE)
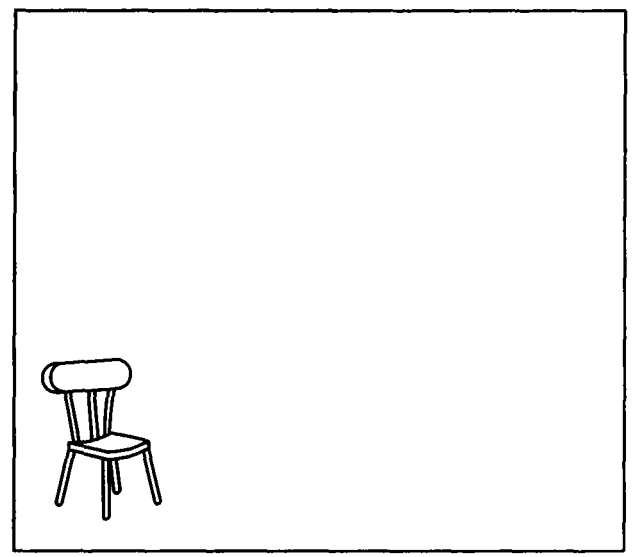
(B) (T+t)-SECOND
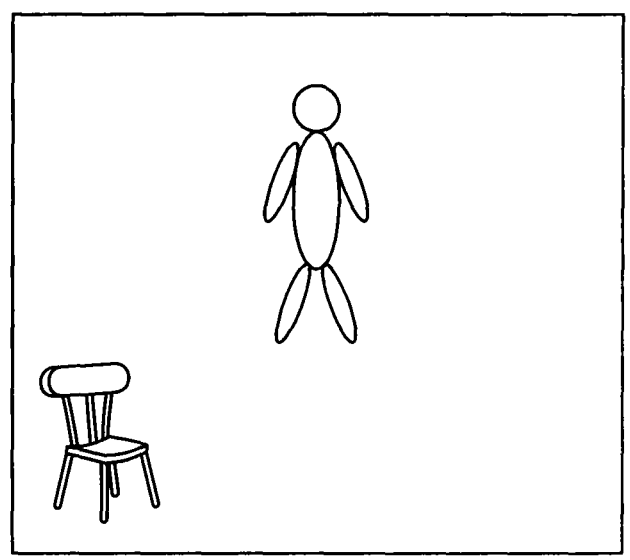
CHAIR IS IGNORABLE

FIG.20

| MOTION ID | SUBJECT MOTION FEATURE INFORMATION |
|---|---|
| 11 | DRAGGING ONE'S LEG |
| 12 | WALKING WITH POOR POSTURE |
| 13 | WALKING SLOWLY |
| ⋮ | ⋮ |

FIG.21

| MOTION ID | CAREGIVER MOTION FEATURE INFORMATION |
|---|---|
| 21 | SUPPORTING SUBJECT'S ARM |
| 22 | WALKING WITH GOOD POSTURE |
| 23 | WALKING FAST |
| ⋮ | ⋮ |

FIG.22

| EQUIPMENT ID | SUBJECT EQUIPMENT FEATURE INFORMATION |
|---|---|
| 11 | CRUTCH |
| 12 | CAST |
| 13 | WHEEL CHAIR |
| ⋮ | ⋮ |

| EQUIPMENT ID | CAREGIVER EQUIPMENT FEATURE INFORMATION |
|---|---|
| 21 | STETHOSCOPE |
| 22 | WHITE COAT |
| 23 | NAMEPLATE |
| ⋮ | ⋮ |

FIG.25

REHABILITATION RECORDS

Esc | OPERATING INSTRUCTIONS

DISEASE NAME | EDIT
SUSPECTED OF LUMBAGO    H18-9-11
CONSTIPATION                       H18-10-2
OSTEOARTHRITIS OF KNEES  H18-10-2

TREATMENTS

ATTENDING PT | TEST SUBSTITUTE | DELETE | START 13:19 ~ END | COMPLETED | TREATMENT | REHABILITATION

PROCEDURES/MEDICATIONS

| | NAME | QUANTITY | UNIT |
| REHABILITATION | EXERCISE EQUIPMENT REHABILITATION FEE (II) [EXERCISE EQUIPMENT REHABILITATION] | | |
| TREATMENT | WOUND TREATMENT (LESS THAN 100 cm²) | 1 | TIME |

SITE 18a
18b

PERSON 18a IS DETERMINED TO BE SUBJECT. CORRECT?
YES/NO

SECTION COMMENTS
DR COMMENTS

BODY INCLINATION:
15°

| PERSONAL FEATURE ID | PERSONAL FEATURE INFORMATION |
|---|---|
| 001 | ( ) cm IN HEIGHT |
| 002 | ( ) cm IN CHEST CIRCUMFERENCE |
| 003 | ( ) cm IN ABDOMINAL CIRCUMFERENCE |
| ⋮ | ⋮ |

| STAFF ID | NAME |
|---|---|
| 1 | AB |
| 2 | CD |
| 3 | EF |
| ⋮ | ⋮ |

FIG.38

| NAME | NAME NUMBER | MOTION INFORMATION FOR BROWSING | | | | | | | | | | | | | |
|---|---|---|---|---|---|---|---|---|---|---|---|---|---|---|---|
| | | DATE | MEDICAL IMAGE INFORMATION | DEPTH IMAGE INFORMATION | SPEECH RECOGNITION RESULT | SKELETON INFORMATION | ・ | | | | | | | | |
| A | 1 | 20120801_1 | MEDICAL IMAGE INFORMATION | DEPTH IMAGE INFORMATION | SPEECH RECOGNITION RESULT | SKELETON INFORMATION | ・ | | | | | | | | |
| | | 20120801_2 | MEDICAL IMAGE INFORMATION | DEPTH IMAGE INFORMATION | SPEECH RECOGNITION RESULT | SKELETON INFORMATION | ・ | | | | | | | | |
| | | 20120802_1 | MEDICAL IMAGE INFORMATION | DEPTH IMAGE INFORMATION | SPEECH RECOGNITION RESULT | SKELETON INFORMATION | ・ | | | | | | | | |
| | | ・ | ・ | ・ | ・ | ・ | ・ | | | | | | | | |
| | | ・ | ・ | ・ | ・ | ・ | ・ | | | | | | | | |
| B | 2 | 20120803_1 | MEDICAL IMAGE INFORMATION | DEPTH IMAGE INFORMATION | SPEECH RECOGNITION RESULT | SKELETON INFORMATION | ・ | | | | | | | | |
| | | 20120804_1 | MEDICAL IMAGE INFORMATION | DEPTH IMAGE INFORMATION | SPEECH RECOGNITION RESULT | SKELETON INFORMATION | ・ | | | | | | | | |
| | | 20120805_1 | MEDICAL IMAGE INFORMATION | DEPTH IMAGE INFORMATION | SPEECH RECOGNITION RESULT | SKELETON INFORMATION | ・ | | | | | | | | |
| ・ | ・ | | | | | | | | | | | | | | |

MOTION INFORMATION PROCESSING DEVICE

CROSS-REFERENCE TO RELATED APPLICATIONS

This application is a continuation of PCT international application Ser. No. PCT/JP2014/051023 filed on Jan. 20, 2014 which designates the United States, incorporated herein by reference, and which claims the benefit of priority from Japanese Patent Application No. 2013-007872, filed on Jan. 18, 2013, Japanese Patent Application No. 2013-167836, filed on Aug. 12, 2013, and Japanese Patent Application No. 2013-171755, filed on Aug. 21, 2013, the entire contents of which are incorporated herein by reference.

FIELD

Embodiments described herein relate generally to a motion information processing device.

BACKGROUND

In rehabilitation, support has been provided by many experts working in cooperation for the purpose of helping those experiencing mental or physical disabilities due to various causes such as illnesses, injuries, or aging or those having congenital disorders to lead better lives. For example, rehabilitation involves support provided by many experts such as rehabilitation specialists, rehabilitation nurses, physical therapists, occupational therapists, speech-language-hearing therapists, clinical psychologists, prosthetists and orthotists, and social workers working in cooperation.

In the meantime, in recent years, development of motion capture technologies for digitally recording motions of people and objects has been advancing. Examples of systems of the motion capture technologies that are known include optical, mechanical, magnetic, and camera systems. For example, a camera system of digitally recording motions of a person by making the person wear a marker, detecting the marker by a tracker such as a camera, and processing the detected marker is known. For another example, as a system that does not use markers and trackers, a system of digitally recording motions of a person by using an infrared sensor to measure the distance from the sensor to the person and detect the size and various motions of the skeleton of the person is known. Kinect (registered trademark), for example, is known as a sensor using such a system.

BRIEF DESCRIPTION OF THE DRAWINGS

FIG. 3 is a table illustrating an example of skeleton information generated by the motion information generation circuitry according to the first embodiment;

FIG. 7 is a table illustrating an example of motion information stored in motion information storage circuitry by the specification circuitry according to the first embodiment;

FIG. 11A is a table illustrating an example of recognition information stored by recognition information storage circuitry according to the second embodiment;

FIG. 11B is a table illustrating an example of recognition information stored by the recognition information storage circuitry according to the second embodiment;

FIG. 13 is a flowchart illustrating procedures of processing performed by the motion information processing device according to the second embodiment;

FIG. 15 is a diagram for explaining an example of processing performed by input circuitry and a specification circuitry according to a fourth embodiment;

FIG. 16 is a diagram for explaining an example of processing performed by specification circuitry according to a fifth embodiment;

FIG. 17 is a diagram for explaining an example of processing performed by specification circuitry according to a sixth embodiment;

FIG. 20 is a table illustrating an example of information stored in subject motion feature storage circuitry;

FIG. 21 is a table illustrating an example of information stored in caregiver motion feature storage circuitry;

FIG. 22 is a table illustrating an example of information stored in subject image feature storage circuitry;

FIG. 25 is a diagram illustrating an example of a display screen displayed by storage circuitry;

FIG. 26 is a diagram illustrating an example of a display screen displayed by the storage circuitry;

FIG. 31 is a table illustrating an example of information stored in personal feature information storage circuitry;

FIG. 38 is a table illustrating an example of motion information for browsing stored in a medical image archiving device according to the eleventh embodiment;

DETAILED DESCRIPTION

A motion information processing device for supporting a rehabilitation according to an embodiment includes obtaining circuitry and specification circuitry. The obtaining circuitry obtains image information of a subject carrying out a predetermined motion in the rehabilitation and surroundings of the subject. The specification circuitry specifies motion information of the subject carrying out the predetermined motion on the basis of a predetermined feature in the image information obtained by the obtaining circuitry.

Hereinafter, motion information processing devices according to embodiments will be described with reference to the drawings. Note that the motion information processing devices described below may be used alone or may be embedded in a system such as a medical record system or a rehabilitation department system, for example.

First Embodiment

Figure 1:
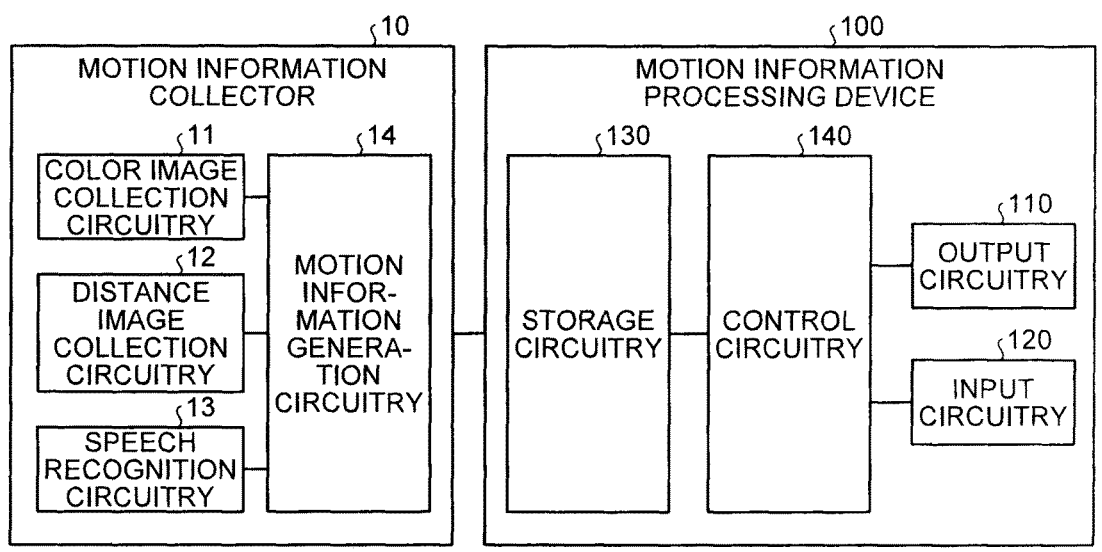
FIG. 1 is a block diagram illustrating an example configuration of a motion information processing device according to a first embodiment.

FIG. 1 is a diagram illustrating an example of the configuration of a motion information processing device 100 according to a first embodiment. The motion information processing device 100 according to the first embodiment is a device to support rehabilitation in a medical institution, at home, in an office, or the like, for example. Note that "rehabilitation" refers to techniques and methods for developing the potentials of patients with disabilities, chronic diseases, geriatric diseases and the like receiving prolonged treatment, and restoring and promoting their vital functions and also their social functions. Examples of such techniques and methods include functional exercises for restoring and promoting vital functions and social functions. Note that examples of the functional exercises include gait training and range of motion exercise. A person who undergoes rehabilitation will be referred to as a "subject." Examples of the subject include a sick person, an injured person, an aged person, and a handicapped person. In addition, a person who assists a subject in rehabilitation will be referred to as a "caregiver." Examples of the caregiver include healthcare professionals such as a doctor, a physical therapist, and a nurse working at medical institutions, and a care worker, a family member, and a friend caring a subject at home, for example. Furthermore, rehabilitation will also be abbreviated as "rehab."

As illustrated in FIG. 1, in the first embodiment, the motion information processing device 100 is connected to a motion information collector 10.

The motion information collector 10 detects motion of a person, an object, or the like in a space in which rehabilitation is carried out, and collects motion information representing the motion of the person, the object, or the like. The motion information will be described in detail later in the description of processing performed by motion information generation circuitry 14. For the motion information collector 10, Kinect (registered trademark) is used, for example.

As illustrated in FIG. 1, the motion information collector 10 includes color image collection circuitry 11, distance image collection circuitry 12, speech recognition circuitry 13, and the motion information generation circuitry 14. Note that the configuration of the motion information collector 10 illustrated in FIG. 1 is only an example, and the embodiment is not limited thereto.

The color image collection circuitry 11 photographs a subject such as a person, an object, or the like in a space in which rehabilitation is carried out, and collects color image information. The color image collection circuitry 11 detects light reflected by a surface of the subject by a photodetector, and converts visible light into an electrical signal, for example. The color image collection circuitry 11 then generates one frame of color image information corresponding to the photographed range by converting the electrical signal into digital data. The color image information of one frame contains photographing time information, and information of pixels contained in the frame and RGB (red, green, and blue) values with which the respective pixels are associated, for example. The color image collection circuitry 11 takes a moving image of the photographed range by generating multiple successive frames of color image information from visible light detected successively. Note that the color image information generated by the color image collection circuitry 11 may be output as a color image in which the RGB values of the pixels are arranged in a bitmap. The color image collection circuitry 11 has a complementary metal oxide semiconductor (CMOS) or a charge coupled device (CCD), for example, as the photodetector.

The distance image collection circuitry 12 photographs a subject such as a person, an object, or the like in a space in which rehabilitation is carried out, and collects distance image information. The distance image collection circuitry 12 irradiates a surrounding area with infrared light and detects with a photodetector a reflected wave that is the irradiation wave reflected by a surface of the subject, for example. The distance image collection circuitry 12 then obtains the distance between the subject and the distance image collection circuitry 12 on the basis of a phase difference between the irradiation wave and the reflected wave and on the time from the irradiation to the detection, and generates one frame of distance image information corresponding to the photographed range. The distance image information of one frame contains photographing time information, and information of pixels contained in the photographed range and the distances between the subject and the distance image collection circuitry 12 with which the respective pixels are associated, for example. The distance image collection circuitry 12 takes a moving image of the photographed range by generating multiple successive frames of distance image information from reflected waves detected successively. Note that the distance image information generated by the distance image collection circuitry 12 may be output as a distance image in which shades of colors according to the distances of the pixels are arranged in a bitmap. The distance image collection circuitry 12 has a CMOS or a CCD, for example, as the photodetector. The photodetector may also be used in common as the photodetector used in the color image collection circuitry 11. The unit of a distance calculated by the distance image collection circuitry 12 is meter [m], for example.

The speech recognition circuitry 13 collects speech therearound, and carries out determination of the direction of a speech source and speech recognition. The speech recognition circuitry 13 has a microphone array including multiple microphones, and carries out beamforming. Beamforming is a technique for selectively collecting speech from a particular direction. The speech recognition circuitry 13 determines the direction of a speech source through beamforming using the microphone array, for example. The speech recognition circuitry 13 also recognizes words from collected speech by using a known speech recognition technology. Specifically, the speech recognition circuitry 13 generates information of a word recognized according to the speech recognition technology with which the direction from which the word has been uttered and the time when the word has been recognized are associated, for example, as a speech recognition result.

The motion information generation circuitry 14 generates motion information indicating a motion of a person, an object, or the like. The motion information is generated by regarding a motion (gesture) of a person as a series of multiple postures (poses), for example. The outline will be explained as follows. The motion information generation circuitry 14 first obtains coordinates of joints forming a human body skeleton from the distance image information generated by the distance image collection circuitry 12 by pattern matching using human body patterns. The coordinates of the joints obtained from the distance image information are values expressed in a coordinate system of a distance image (hereinafter referred to as a "distance image coordinate system"). Thus, the motion information generation circuitry 14 then converts the coordinates of the joints in the distance image coordinate system into values expressed in a coordinate system of a three-dimensional space in which rehabilitation is carried out (hereinafter referred to as a "world coordinate system"). The coordinates of the joint expressed in the world coordinate system constitute skeleton information of one frame. Furthermore, skeleton information of multiple frames constitutes motion information. Hereinafter, processing performed by the motion information generation circuitry 14 according to the first embodiment will be described more concretely.

Figure 2A:
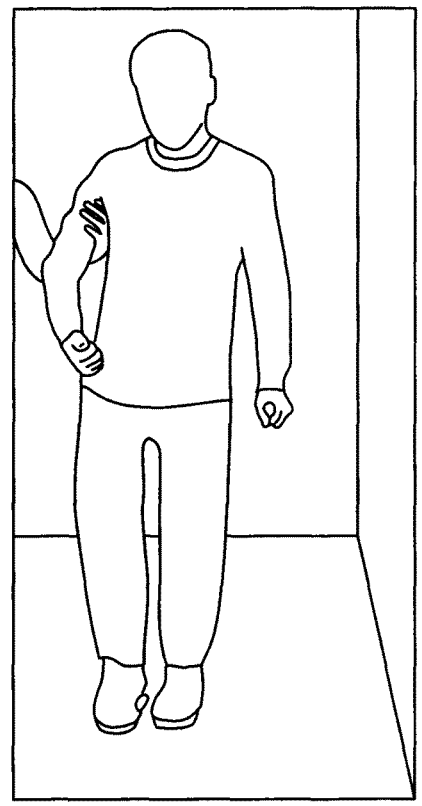
FIG. 2A is a diagram for explaining processing of motion information generation circuitry according to the first embodiment.
Figure 2B:
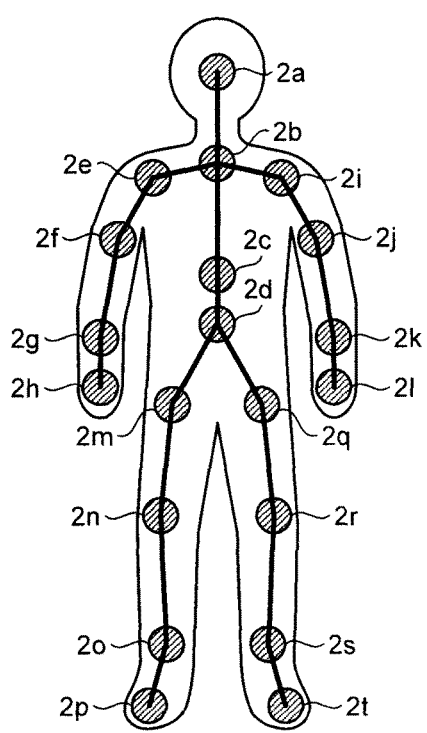
FIG. 2B is a diagram for explaining processing of the motion information generation circuitry according to the first embodiment.
Figure 2C:
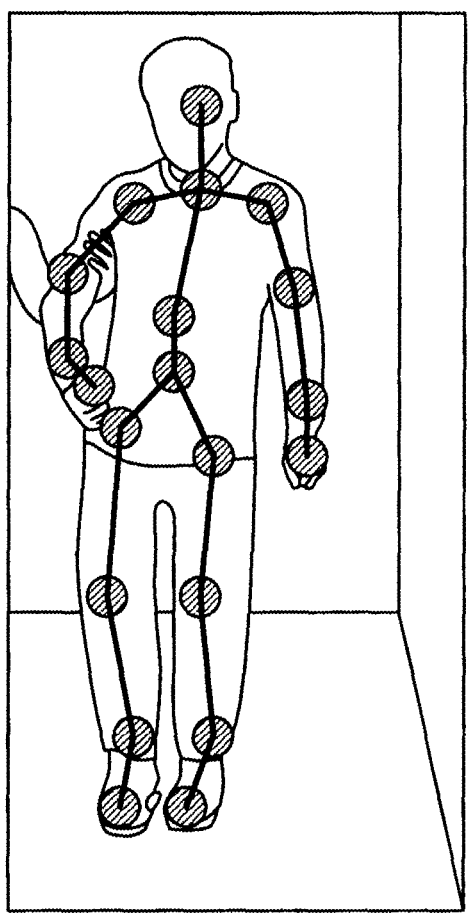
FIG. 2C is a diagram for explaining processing of the motion information generation circuitry according to the first embodiment.

FIGS. 2A to 2C are diagrams for explaining processing performed by the motion information generation circuitry 14 according to the first embodiment. FIG. 2A illustrates an example of a distance image taken by the distance image collection circuitry 12. Note that, in FIG. 2A, an image expressed by line drawing is presented for the purpose of illustration, an actual distance image is an image expressed by color shadings according to the distances, or the like. In this distance image, each pixel has three-dimensional values, which are a "pixel position X" in the horizontal direction of the distance image, a "pixel position Y" in the vertical direction of the distance image, and a "distance Z" between the subject corresponding to the pixel and the distance image collection circuitry 12. Hereinafter, coordinate values in the distance image coordinate system will be expressed by the three-dimensional values (X, Y, Z).

In the first embodiment, the motion information generation circuitry 14 stores human body patterns corresponding to various postures through learning, for example, in advance. Each time distance image information is generated by the distance image collection circuitry 12, the motion information generation circuitry 14 acquires the generated distance image information of each frame. The motion information generation circuitry 14 then carries out pattern matching on the acquired distance image information of each frame using the human patterns.

Here, the human patterns will be described. FIG. 2B illustrates an example of the human patterns. In the first embodiment, the human patterns are patterns used in pattern matching with the distance image information, and are thus expressed in the distance image coordinate system and have information on the surfaces of human bodies (hereinafter referred to as "human body surfaces") similarly to a person drawn in a distance image. A human body surface corresponds to the skin or the surface of clothing of the person, for example. Furthermore, a human body pattern has information on joints forming human skeleton as illustrated in FIG. 2B. Thus, in a human pattern, relative positions of a human body surface and the joints are known.

In the example illustrated in FIG. 2B, the human body pattern has information on 20 joints, from a joint $2a$ to a joint $2t$. The joint $2a$ corresponds to the head, the joint $2b$ corresponds to the center of the shoulders, the joint $2c$ corresponds to the waist, and the joint $2d$ corresponds to the center of the hip. The joint $2e$ corresponds to the right shoulder, the joint $2f$ corresponds to the right elbow, the joint $2g$ corresponds to the right wrist, and the joint $2h$ corresponds to the right hand. The joint $2i$ corresponds to the left shoulder, the joint $2j$ corresponds to the left elbow, the joint $2k$ corresponds to the left wrist, and the joint $2l$ corresponds to the left hand. The joint $2m$ corresponds to the right hip, the joint $2n$ corresponds to the right knee, the joint $2o$ corresponds to the right ankle, and the joint $2p$ corresponds to the tarsus of the right foot. The joint $2q$ corresponds to the left hip, the joint $2r$ corresponds to the left knee, the joint $2s$ corresponds to the left ankle, and the joint $2t$ corresponds to the tarsus of the left foot.

While a case in which the human body pattern has information on 20 joints is illustrated in FIG. 2B, the embodiment is not limited thereto, and the positions and the number of joints may be arbitrarily be set by an operator. For example, for capturing only a change in the motion of the limbs, information on the joint $2b$ and the joint $2c$ of the joints $2a$ to $2d$ need not be acquired. For capturing a change in the motion of the right hand in detail, joints of the fingers of the right hand may be newly set in addition to the joint $2h$. Note that, although the joint $2a$, the joint $2h$, the joint $2l$, the joint $2p$, and the joint $2t$ in FIG. 2B are at distal portions of bones and are thus different from what are actually called joints, these points will be referred to as joints for the purpose of explanation since the points are important points for indicating the positions and orientations of the bones.

The motion information generation circuitry 14 carries out pattern matching with the distance image information of each frame by using such human body patterns. For example, the motion information generation circuitry 14 carries out pattern matching between the human body surface of the human body pattern illustrated in FIG. 2B and the distance image illustrated in FIG. 2A to extract a person in a certain posture from the distance image information. In this manner, the motion information generation circuitry 14 obtains the coordinates of the human body surface of the person drawn in the distance image. Furthermore, as described above, in a human pattern, relative positions of a human body surface and joints are known. The motion information generation circuitry 14 thus calculates the coordinates of the joints in the person drawn in the distance image from the coordinates of the human body surface of the person. In this manner, as illustrated in FIG. 2C, the motion information generation circuitry 14 obtains the coordinates of the joints forming the human body skeleton from the distance image information.

Note that the coordinates of the joints obtained here are coordinates in the distance image coordinate system. Note that the motion information generation circuitry 14 may use information indicating relative positions of the joints supplementarily in carrying out the pattern matching. The information indicating the relative positions of the joints contains connections between joints ("connection between the joint $2a$ and the joint $2b$," for example), and the ranges of motion of the joints, for example. A joint is a part connecting two or more bones. The angle between bones changes with a change in posture, and the ranges of range are different for different joints. A range of motion is expressed by the largest value and the smallest value of the angle between bones that the joint connects, for example. In learning a human body pattern, the motion information generation circuitry 14 also learns the ranges of motion of the joints and stores the learned ranges of motion in association with the respective joints, for example.

Subsequently, the motion information generation circuitry 14 converts the coordinates of the joints in the distance image coordinate system into values expressed in the world coordinate system. The world coordinate system refers to a coordinate system of a three-dimensional space in which rehabilitation is carried out, such as a coordinate system with the origin at the position of the motion information collector 10, the x-axis in the horizontal direction, the y-axis in the vertical direction, and the z-axis in a direction perpendicular to the xy plane. Note that a coordinate value in the z-axis direction may be referred to as a "depth."

Here, processing of conversion from the distance image coordinate system to the world coordinate system will be described. In the first embodiment, it is assumed that the motion information generation circuitry 14 stores in advance a conversion formula for conversion from the distance image coordinate system to the world coordinate system.

Coordinates in the distance image coordinate system and an entrance angle of reflected light associated with the coordinates are input to this conversion formula and coordinates in the world coordinate system are output therefrom, for example. The motion information generation circuitry 14 inputs coordinates (X1, Y1, Z1) of a joint and the entrance angle of reflected light associated with the coordinates to the conversion formula, and converts the coordinates (X1, Y1, Z1) of the joint into coordinates (x1, y1, z1) of the world coordinate system, for example. Note that, since the relation between the coordinates in the distance image coordinate system and the entrance angle of reflected light is known, the motion information generation circuitry 14 can input the entrance angle associated with the coordinates (X1, Y1, Z1) into the conversion formula. Although a case in which the motion information generation circuitry 14 converts coordinates in the distance image coordinate system into coordinates in the world coordinate system has been described here, the motion information generation circuitry 14 may alternatively convert coordinates in the world coordinate system into coordinates in the distance image coordinate system.

The motion information generation circuitry 14 then generates skeleton information from the coordinates of the joints expressed in the world coordinate system. FIG. 3 is a table illustrating an example of the skeleton information generated by the motion information generation circuitry 14. The skeleton information of each frame contains photographing time information of the frame and the coordinates of the joints. The motion information generation circuitry 14 generates skeleton information containing joint identification information and coordinate information associated with each other as illustrated in FIG. 3, for example. Note that the photographing time information is not illustrated in FIG. 3. The joint identification information is identification information for identifying a joint, and is set in advance. For example, joint identification information "$2a$" corresponds to the head, and joint identification information "$2b$" corresponds to the center of the shoulders. The other joint identification information data similarly indicate the respective corresponding joints. The coordinate information indicates coordinates of each joint in each frame in the world coordinate system.

In the first row of FIG. 3, the joint identification information "$2a$" and the coordinate information "(x1, y1, z1)" are associated. Specifically, the skeleton information of FIG. 3 indicates that the head is present at the position of coordinates (x1, y1, z1) in a certain frame. In addition, in the second row of FIG. 3, the joint identification information "$2b$" and the coordinate information "(x2, y2, z2)" are associated. Specifically, the skeleton information of FIG. 3 indicates that the center of the shoulders is present at the position of coordinates (x2, y2, z2) in a certain frame. Similarly for the other joints, the skeleton information indicates that each joint is present at a position expressed by the corresponding coordinates in a certain frame.

In this manner, the motion information generation circuitry 14 carries out pattern matching on the distance image information of each frame each time the distance image information of each frame is acquired from the distance image collection circuitry 12, and converts the coordinates from the distance image coordinate system into those in the world coordinate system to generate the skeleton information of each frame. The motion information generation circuitry 14 then outputs the generated skeleton information of each frame to the motion information processing device 100 to store the skeleton information in motion information storage circuitry 131, which will be described later.

Note that the processing of the motion information generation circuitry 14 is not limited to the technique described above. For example, although a technique in which the motion information generation circuitry 14 carries out pattern matching using human body patterns has been described above, the embodiment is not limited thereto. For example, a technique in which patterns of each part is used instead of or in addition to the human body patterns may be used.

Furthermore, for example, although a technique in which the motion information generation circuitry 14 obtains coordinates of joints from the distance image information has been described above, the embodiment is not limited thereto. For example, a technique in which the motion information generation circuitry 14 obtains coordinates of joints by using color image information in addition to the distance image information may be used. In this case, the motion information generation circuitry 14 carries out pattern matching between a human body pattern expressed in a coordinate system of a color image and the color image information, and obtains coordinates of the human body surface from the color image information, for example. The coordinate system of the color image does not include information corresponding to the "distance Z" in the distance image coordinate system. Thus, the motion information generation circuitry 14 obtains the information on the "distance Z" from the distance image information, for example, and obtains coordinates of joints in the world coordinate system through a calculation process using these to information data.

The motion information generation circuitry 14 also outputs color image information generated by the color image collection circuitry 11, distance image information generated by the distance image collection circuitry 12, and a speech recognition result output from the speech recognition circuitry 13, where necessary, to the motion information processing device 100 to store the color image information, the distance image information, and the speech recognition result in the motion information storage circuitry 131, which will be described later. Note that a pixel position in the color image information and a pixel position in the distance image information can be associated with each other in advance according to the positions of the color image collection circuitry 11 and the distance image collection circuitry 12 and the photographing direction. Thus, a pixel position in the color image information and a pixel position in the distance image information can also be associated with the world coordinate system calculated by the motion information generation circuitry 14. Furthermore, the height and the lengths of body parts (the length of an arm, the length of the abdomen, etc.) can be obtained or the distance between two pixels specified on a color image can be obtained by using the association and a distance [m] calculated by the distance image collection circuitry 12. Similarly, the photographing time information in the color image information and the photographing time information in the distance image information can also be associated with each other in advance. In addition, the motion information generation circuitry 14 can refer to the speech recognition result and the distance image information, and if a joint $2a$ is present about the direction in which a word recognized through speech recognition at certain time has been uttered, can output the word as a word uttered by a person having the joint $2a$. Furthermore, the motion information generation circuitry 14 also outputs information indicating relative positions of the joints, where necessary, to the motion information processing device 100 to store the information in the motion information storage circuitry 131, which will be described later.

The motion information generation circuitry 14 also generates depth image information of one frame corresponding to the photographed range by using a depth that is a coordinate value in the z-axis direction of the world coordinate system. The depth image information of one frame contains photographing time information, and information of pixels contained in the photographed range with which the depths associated with the respective pixels are associated, for example. In other words, the depth image information associates the pixels with depth information instead of the distance information with which the pixels in the distance image information are associated, and can indicate the pixel positions in the distance image coordinate system similar to that of the distance image information. The motion information generation circuitry 14 outputs the generated depth image information to the motion information processing device 100 to store the depth image information in the motion information storage circuitry 131. Note that the depth image information may be output as a depth image in which shades of colors according to the depths of the pixels are arranged in a bitmap.

Although a case in which motion of one subject is detected by the motion information collector 10 has been described here, the embodiment is not limited thereto. If multiple subjects are included in the detection range of the motion information collector 10, the motion information collector 10 may detect motions of multiple subjects. If multiple subjects are photographed in distance image information of the same frame, the motion information collector 10 associates the skeleton information data of the multiple subjects generated by the distance image information of the same frame, and outputs the associated skeleton information data as motion information to the motion information processing device 100.

Note that the configuration of the motion information collector 10 is not limited to the configuration described above. For example, in a case where motion information is generated by detecting motion of a person through another motion capture technology such as an optical, mechanical, or magnetic technology, the motion information collector 10 need not necessarily include the distance image collection circuitry 12. In such a case, the motion information collector 10 includes a marker to be worn by a human body to detect the motion of a person and a sensor for detecting the marker as a motion sensor. The motion information collector 10 then detects the motion of the person by using the motion sensor and generates motion information. The motion information collector 10 also associates pixel positions of the color image information and coordinates of the motion information with each other by using the positions of the marker contained in the image photographed by the color image collection circuitry 11, and outputs the association result to the motion information processing device 100 where necessary. In addition, for example, if the motion information collector 10 does not output the speech recognition result to the motion information processing device 100, the motion information collector 10 need not have the speech recognition circuitry 13.

Furthermore, although the motion information collector 10 outputs coordinates in the world coordinate system as the skeleton information in the embodiment described above, the embodiment is not limited thereto. For example, the motion information collector 10 may output coordinates in the distance image coordinate system before conversion, and the conversion from the distance image coordinate system to the world coordinate system may be carried out in the motion information processing device 100 where necessary.

The description refers back to FIG. 1. The motion information processing device 100 performs processing for supporting rehabilitation by using the motion information output from the motion information collector 10. Specifically, the motion information processing device 100 prevents false recognition of a subject in supporting rehab by using image information containing the motion information collected by the motion information collector 10.

As described above, among various exercises that have been carried out as functional exercises in rehab, in rehab such as gait training that is carried out using a wide space, for example, the motion information collector 10 described above may collect information on a person or an object (such as a chair and equipment) other than the subject carrying out rehab. In particular, in a small hospital or a clinic (a medical office), it is difficult to allocate a large space reserved for rehab, and the motion information collector 10 may collect information of a person or an object other than the subject. As a result, the motion information processing device 100 may carry out processing on the basis of false recognition of information on the person or the object other than the subject as information on the subject, which may interfere with processing in various rehab supports. The motion information processing device 100 according to the present embodiment is therefore configured to enable prevention of false recognition of a subject.

The motion information processing device 100 is an information processing device such as a computer or a workstation, for example, and includes output circuitry 110, input circuitry 120, storage circuitry 130, and control circuitry 140 as illustrated in FIG. 1.

The output circuitry 110 outputs various information data for supporting rehabilitation. For example, the output circuitry 110 outputs various information data for supporting rehab by using the motion information of the subject carrying out the rehab. Specifically, the output circuitry 110 outputs various processing results using the motion information of a subject specified by the control circuitry 140, which will be described later. The output circuitry 110 also displays a graphical user interface (GUI) for an operator who operates the motion information processing device 100 to input various request by using the input circuitry 120, displays display information generated by the motion information processing device 100, or outputs an alarm. The output circuitry 110 is a monitor, a speaker, a headphone, or a headphone part of a headset, for example. The output circuitry 110 may be a display that is worn on the body of a user such as a spectacle type display or a head mounted display.

The input circuitry 120 receives input of various information data for supporting rehabilitation. For example, the input circuitry 120 receives input of various information data for preventing false recognition of a subject. For example, the input circuitry 120 receives input of various requests (such as a request for setting a predetermined threshold for determining whether or not what is recognized is the subject, a request for selecting various information data, and a measurement request for measurement on the GUI) from the operator of the motion information processing device 100, and transfers the received requests to the motion information processing device 100. The input circuitry 120 is a mouse, a keyboard, a touch command screen, a trackball, a microphone, or a microphone part of a headset, for example. The input circuitry 120 may be a sensor for acquiring biological information such as a sphygmomanometer, a heart rate monitor, or a clinical thermometer.

The storage circuitry 130 is a storage device such as a semiconductor memory device such as a random access memory (RAM) and a flash memory, a hard disk device, or an optical disk device, for example. The control circuitry 140 can be an integrated circuit such as an application specific integrated circuit (ASIC) or a field programmable gate array (FPGA), or can be implemented in a predetermined program executed by a central processing unit (CPU).

Figure 4:
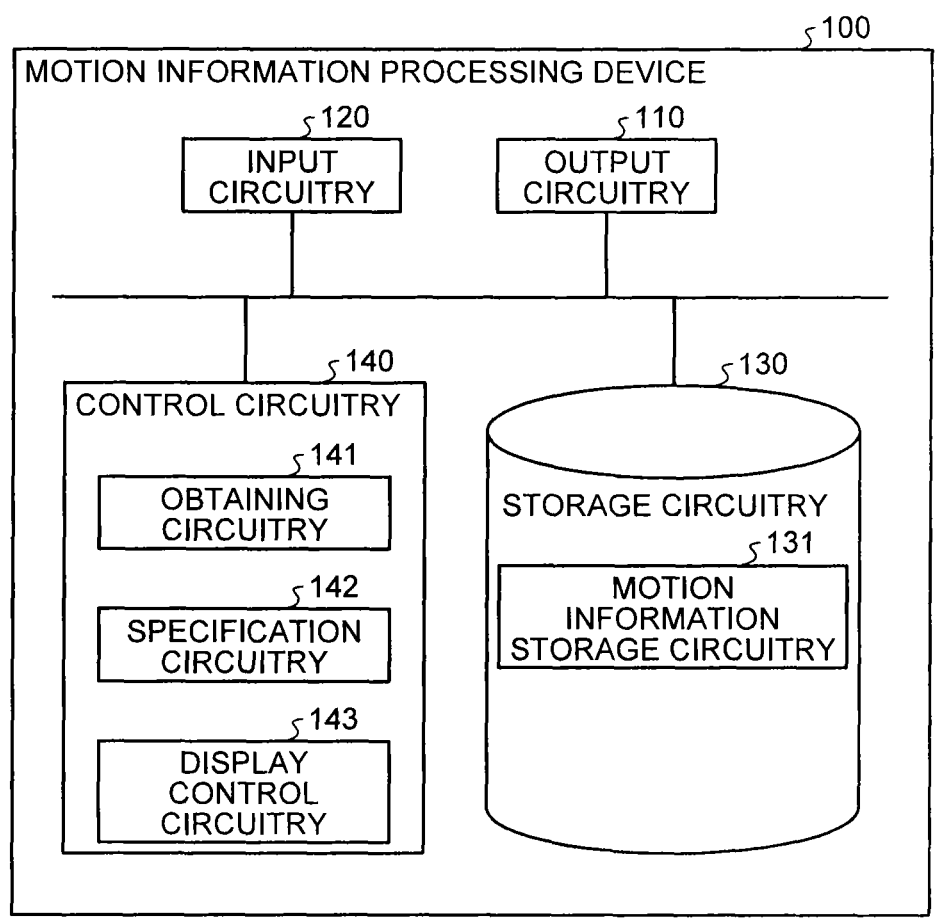
FIG. 4 is a block diagram illustrating a detailed example configuration of the motion information processing device according to the first embodiment.

The configuration of the motion information processing device 100 according to the first embodiment has been described above. With such a configuration, the motion information processing device 100 according to the first embodiment prevents false recognition of a subject by the configuration described hereinafter in detail. In the following embodiment, an example in which gait training is carried out as rehab will be described. FIG. 4 is a diagram illustrating an example of a detailed configuration of the motion information processing device 100 according to the first embodiment. First, the storage circuitry 130 in the motion information processing device 100 will be described. As illustrated in FIG. 4, in the motion information processing device 100, the storage circuitry 130 includes the motion information storage circuitry 131, for example.

The motion information storage circuitry 131 stores various information data collected by the motion information collector 10. Specifically, the motion information storage circuitry 131 stores motion information generated by the motion information generation circuitry 14, and motion information determined to be the motion information of the subject by the control circuitry 140, which will be described later, among the motion information generated by the motion information generation circuitry 14. More specifically, the motion information storage circuitry 131 stores skeleton information of each frame generated by the motion information generation circuitry 14 in the motion information determined to be the motion information of the subject by the control circuitry 140. Note that the motion information storage circuitry 131 can also associate color image information, distance image information, and a speech recognition result output by the motion information generation circuitry 14 for each frame and store the association result.

Note that details of the motion information determined to be the motion information of the subject by the control circuitry 140 and stored in the motion information storage circuitry 131 will be described later.

Next, details of the control circuitry 140 in the motion information processing device 100 will be described. As illustrated in FIG. 4, in the motion information processing device 100, the control circuitry 140 includes obtaining circuitry 141, specification circuitry 142, and a display control circuitry 143, for example.

The obtaining circuitry 141 obtains image information of a subject carrying out a predetermined motion and the surroundings of the subject. Specifically, the obtaining circuitry 141 obtains motion information collected by the motion information collector 10 and stored in the motion information storage circuitry 131. For example, the obtaining circuitry 141 obtains color image information, distance image information, a speech recognition result, skeleton information, and the like stored for each frame in the motion information storage circuitry 131.

Note that the motion information collector 10 may collect information on a person or an object other than the subject carrying out rehab as described above. In particular, in such a case in which rehab is carried out using almost the entirety of a small space, a person or an object other than the subject is likely to be included in the area from which motion information is collected, and the motion information collector 10 may collect information on such person or object and store the information in the motion information storage circuitry 131. The obtaining circuitry 141 obtains motion information of each frame containing such information. Specifically, if skeleton information of a person or an object other than the subject has been collected by the motion information collector 10, the obtaining circuitry 141 obtains motion information containing skeleton information of the subject and skeleton information of the person or object other than the subject in each frame. In such a case, information on the subject and information of the person or object other than the subject are also contained in color image information and distance image information, and the obtaining circuitry 141 can obtain such information.

Figure 5:
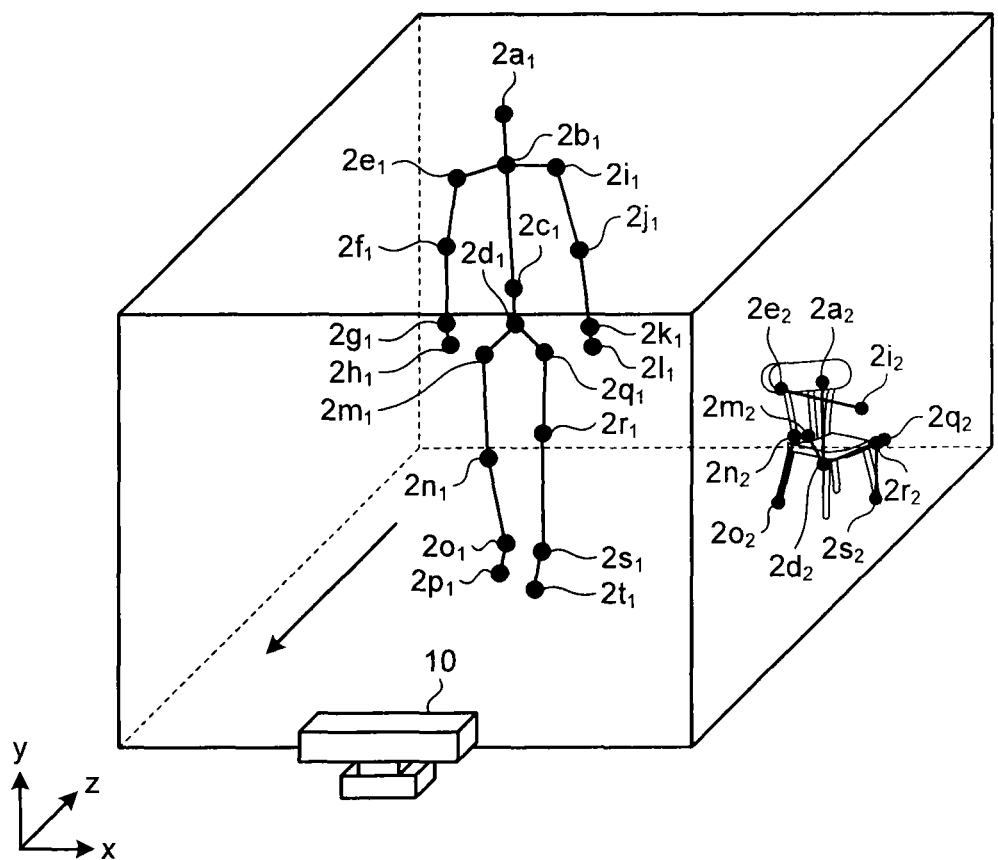
FIG. 5 is a diagram illustrating an example of skeleton information obtained by obtaining circuitry according to the first embodiment.

FIG. 5 is a diagram illustrating an example of skeleton information obtained by the obtaining circuitry 141 according to the first embodiment. Note that FIG. 5 illustrates an example in which the motion information collector 10 has collected skeleton information of a chair placed in the area from which motion information is collected in addition to skeleton information corresponding to the subject carrying out gait training in the area in the direction indicated by an arrow in FIG. 5. For example, the motion information collector 10 collects skeleton information containing joints $2a_1$ to $2t_1$ corresponding to parts of a human body and skeleton information containing joints ($2a_2$, $2d_2$, $2e_2$, $2i_2$, $2m_2$, $2n_2$, $2o_2$, $2q_2$, $2r_2$, and $2s_2$) for each frame as illustrated in FIG. 5, and store the collected skeleton information data in the motion information storage circuitry 131.

In such a case, the obtaining circuitry 141 obtains two type of skeleton information (skeleton information containing the joints $2a_1$ to $2t_1$ and the joints ($2a_2$, $2d_2$, $2e_2$, $2i_2$, $2m_2$, $2n_2$, $2o_2$, $2q_2$, $2r_2$, and $2s_2$)) each contained in all the frames collected during a series of motions of the subject in gait training. Note that the obtaining circuitry 141 can also obtain color image information, distance image information and the like in each frame in addition to the skeleton information described above.

The description refers back to FIG. 4, in which the specification circuitry 142 specifies motion information of the subject carrying out a predetermined motion on the basis of predetermined features in the image information obtained by the obtaining circuitry 141. Specifically, the specification circuitry 142 extracts subject information indicating the subject as the predetermined feature from the image information obtained by the obtaining circuitry 141, and specifies the motion information of the subject carrying out the predetermined motion on the basis of the extracted subject information. For example, the specification circuitry 142 extracts information indicating a moving object contained in the image information as the subject information, and specifies motion information of the subject carrying out the predetermined motion on the basis of the extracted subject information. Note that the specification circuitry 142 determines an object whose position changes in a three-dimensional space around the subject to be a moving object in the image information obtained over time by the obtaining circuitry 141.

Figure 6A:
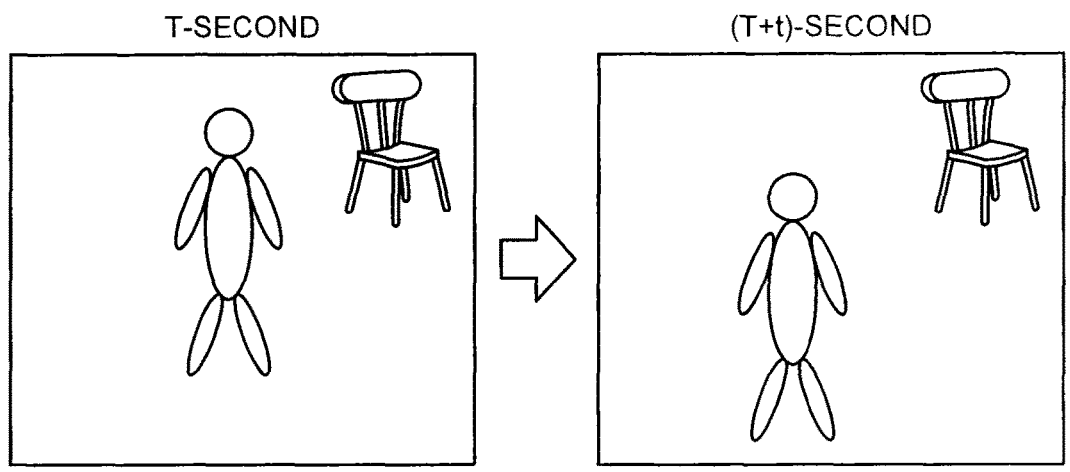
FIG. 6A is a diagram for explaining an example of processing performed by specification circuitry according to the first embodiment.
Figure 6B:
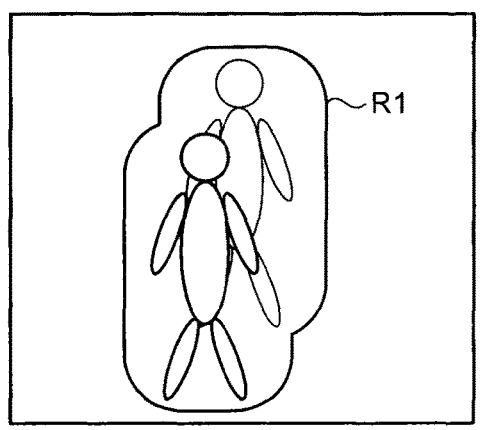
FIG. 6B is a diagram for explaining an example of processing performed by the specification circuitry according to the first embodiment.

FIGS. 6A and 6B are diagrams for explaining an example of processing performed by the specification circuitry 142 according to the first embodiment. FIGS. 6A and 6B illustrate an example of processing using the motion information collected by the motion information collector 10 illustrated in FIG. 5. The specification circuitry 142 reads out an image of a "T-second" frame and a "(T+t)-second" frame of the motion information collected by the motion information collector 10 as illustrated in FIG. 6A, for example. The specification circuitry 142 then extracts a moving object (a moving person or object) in the three-dimensional space from which the motion information has been collected from the read image.

In one example, the specification circuitry 142 extracts the moving object from a difference between a "T-second image" that is an image of the T-second frame and a "(T+t)-second image" that is an image of the (T+t)-second frame, and sets a predetermined area containing the extracted moving object as a recognition target area R1 for specifying the motion information as illustrated in FIG. 6B. If gait training is carried out toward the motion information collector 10 as illustrated in FIG. 5, the specification circuitry 142 obtains the difference in depth between the pixels in the "T-second image" and those in the "(T+t)-second image" to extract pixels whose depth information has changed, for example. For an object such as a chair that does not move, the difference will be "0" since the depth information does not change, and the object can be determined to be an object other than the subject and deleted. The specification circuitry 142 then carries out an area expansion process such as morphological operation on pixels whose depth information has changed, for example, to set the recognition target area R1.

Specifically, the specification circuitry 142 calculates the difference between the "T-second image" and the "(T+t)-second image" to extract pixels corresponding to the moving object in the image. The specification circuitry 142 then carries out the area expansion process on the extracted pixels to set the recognition target area R1 containing the entire moving object. The specification circuitry 142 then specifies motion information contained in the set recognition target area R1 as the motion information of the subject. For example, the specification circuitry 142 specifies skeleton information containing the joints $2a_1$ to $2t_1$ illustrated in FIG. 5 as the motion information of the subject carrying out rehab.

Although a case in which the subject carries out gait training toward the motion information collector 10 has been described in the example above, the embodiment is not limited thereto, and there may be a case in which gait training is carried out in a manner that the subject moves across the motion information collector 10, for example. In such a case, the recognition target area can also be set by calculating the difference in depth similarly to the example described above and extracting the pixels whose depth information has been changed.

Furthermore, although a case in which a moving object is extracted on the basis of a change in depth information has been described in the example above, the embodiment is not limited thereto, and there may be a case in which pixel values in color image information are used, for example. In such a case, the recognition target area is set by obtaining the difference between pixel values of a color image of a "T-second" frame and pixel values of a color image of a "(T+t)-second" frame and extracting pixels whose pixel values have been changed, for example.

Alternatively, the recognition target area can also be set by collecting temperature information for each frame through thermography, calculating the difference in the collected temperature information between a "T-second image" and a "(T+t)-second image," and extracting pixels whose temperature information has been changed, for example.

In the example above, a case in which the moving object is extracted on the basis of the difference between images of two frames, which are the "T-second image" and the "(T+t)-second image" has been described. The embodiment, however, is not limited thereto, and there may be a case in which a moving object is extracted on the basis of differences between images of three or more frames, for example. In one example, a case in which the differences in depth between a "T-second image," a "(T+t)-second image," and a "(T+2*t*)-second image" are obtained, an area in which the depth becomes gradually shallower (or deeper), an area in which the depth changes in one direction over time, or the like is extracted, and the extracted area is set as the recognition target area may be used. As a result, a subject carrying out a regular motion such as gait training can be properly identified even if motion information of a person other than the subject carrying out gait training is collected by the motion information collector 10, for example.

The specification circuitry 142 specifies the motion information (skeleton information) contained in the recognition target area R1 set by any of various methods described above as the motion information (skeleton information) of the subject. The specification circuitry 142 then stores the specified skeleton information in association with color image information, distance image information or the like collected by the motion information collector 10 into the motion information storage circuitry 131.

FIG. 7 is a table illustrating an example of motion information stored in the motion information storage circuitry 131 by the specification circuitry 142 according to the first embodiment. The specification circuitry 142 stores motion information in which a name number, a date, and motion information are associated with each name as illustrated in FIG. 7 in the motion information storage circuitry 131. Note that the "name number" refers to an identifier for uniquely identifying a subject, and is assigned to each name. The "date" refers to the date and time when the subject has carried out rehab (such as gait training). The "motion information" refers to information collected by the motion information collector 10.

The specification circuitry 142 stores "name: A, name number: 1, date: 20120801_1, motion information: color image information, distance image information, speech recognition result, skeleton information," as illustrated in FIG. 7, for example. The above information indicates that motion information containing "color image information," "distance image information," a "speech recognition result," and "skeleton information" is stored as motion information in the "first" gait training carried out by a person with a "name: A" whose "name number" is "1" on "Aug. 1" in "2012." Note that the specification circuitry 142 associates and stores the skeleton information specified as the skeleton information of the subjects as the skeleton information illustrated in FIG. 7. The specification circuitry 142 also stores the "color image information," the "distance image information," the "speech recognition result," and the "skeleton information" of each of all the frames photographed during the gait training as the motion information illustrated in FIG. 7 in association with time in time series.

The specification circuitry 142 also stores "name: A, name number: 1, date: 20120801_2, motion information: color image information, distance image information, speech recognition result, skeleton information," as illustrated in FIG. 7, for example. Specifically, the specification circuitry 142 similarly stores motion information in the "second" gait training carried out by the person with the "name: A" on "Aug. 1" in "2012". Note that, similarly in the "second" gait training, the skeleton information specified as the skeleton information of the subject is associated and stored.

The specification circuitry 142 also stores motion information containing "color image information," "distance image information," a "speech recognition result," and "skeleton information" for a person with "name: B, name number: 2," as illustrated in FIG. 7. In this manner, the specification circuitry 142 stores motion information in gait training collected for each subject in association with the subject. Note that the motion information illustrated in FIG. 7 is merely an example. Specifically, the specification circuitry 142 can further associate and store information other than the "color image information," the "distance image information," the "speech recognition result," and the "skeleton information" illustrated in FIG. 7, and if the motion information collector 10 does not include the speech recognition circuitry 13, for example, stores the motion information without the speech recognition result.

The "color image information" and the "distance image information" contained in the motion information contain image data in bitmap, JPEG, or other binary formats, a link to the image data, or the like. Furthermore, the "speech recognition result" contained in the motion information may contain speech data or a link to the speech data in addition to the recognition information described above.

Figure 8:
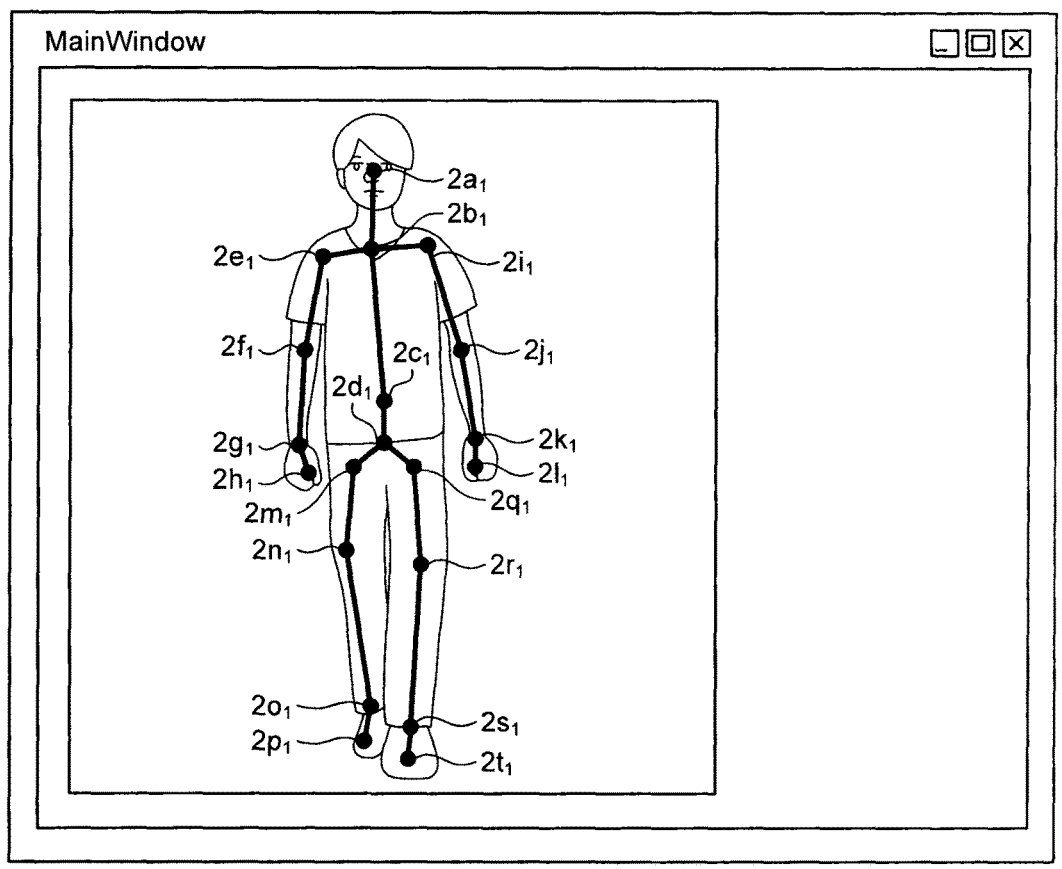
FIG. 8 is a diagram illustrating an example of a display image displayed by display control circuitry according to the first embodiment.

The description refers back to FIG. 4, in which the display control circuitry 143 performs control to display a display image in which information indicating the subject is superimposed on the image information at the position corresponding to the motion information specified by the specification circuitry 142. Specifically, the display control circuitry 143 displays the display image by using the motion information stored in the motion information storage circuitry 131 by the specification circuitry 142. FIG. 8 is a diagram illustrating an example of the display image displayed by the display control circuitry 143 according to the first embodiment. For example, the display control circuitry 143 performs control to display a display image in which dots and lines indicating the skeleton information specified by the specification circuitry 142 are superimposed on color image information collected by the motion information collector 10 on the output circuitry 110, as illustrated in FIG. 8.

The display information in which skeleton information is properly superimposed on the subject contained in color image information can be displayed by superimposing the skeleton information specified as the motion information of the subject by the specification circuitry 142 on the color image information in this manner.

Figure 9:
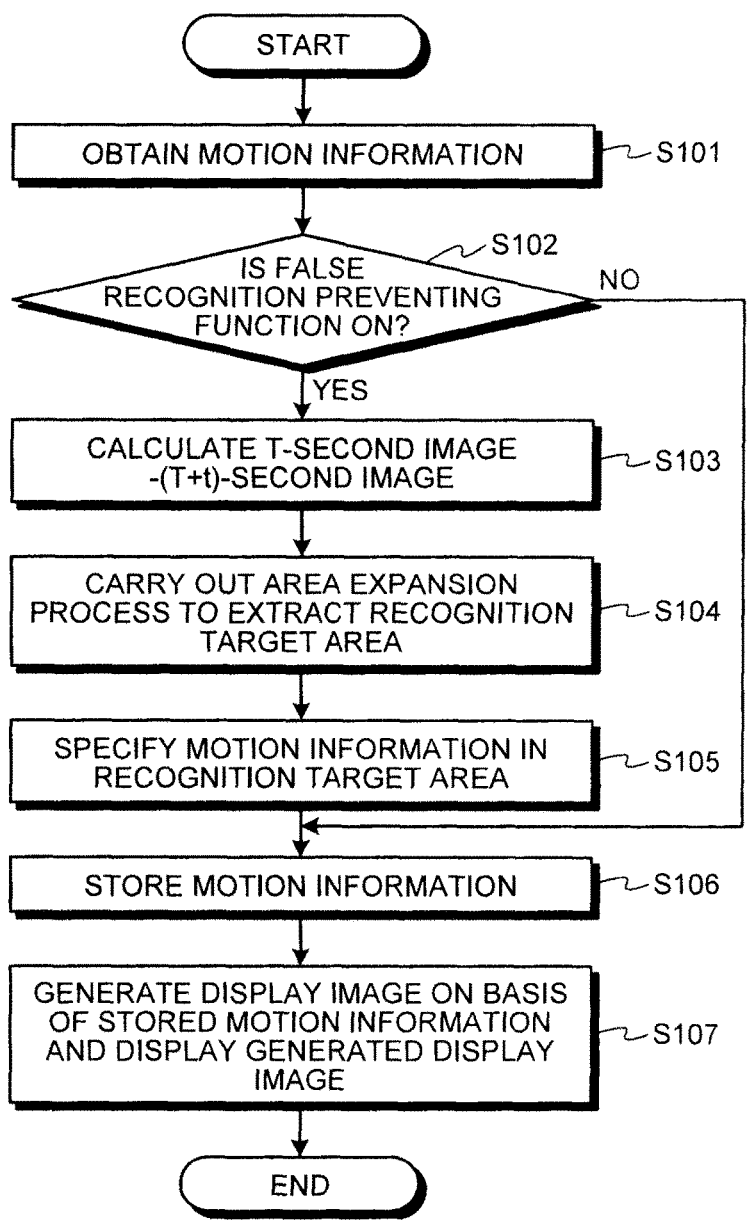
FIG. 9 is a flowchart illustrating procedures of processing performed by the motion information processing device according to the first embodiment.

Next, processing of the motion information processing device 100 according to the first embodiment will be described with reference to FIG. 9. FIG. 9 is a flowchart illustrating procedures of the processing performed by the motion information processing device 100 according to the first embodiment. As illustrated in FIG. 9, in the motion information processing device 100 according to the first embodiment, the obtaining circuitry 141 obtains motion information of a subject (step S101). The specification circuitry 142 then determines whether or not a false recognition preventing function for preventing false recognition of a subject is ON (step S102).

If the false recognition preventing function is ON (Yes in step S102), the specification circuitry 142 obtains a "T-second image" and a "(T+t)-second image," and calculates "T-second image—(T+t)-second image" (step S103). The specification circuitry 142 then carries out the area expansion process to extract the recognition target area (step S104).

Thereafter, the specification circuitry 142 specifies motion information (skeleton information) in the extracted recognition target area (step S105), and stores the specified motion information (skeleton information) in the motion information storage circuitry 131 (step S106).

If the false recognition preventing function is not ON in step S102 (No in step S102), the motion information is stored in the motion information storage circuitry 131 without the specification by the specification circuitry 142 (step S106).

The display control circuitry 143 then performs control to generate a display image on the basis of the motion information stored in the motion information storage circuitry 131 and display the display image on the output circuitry 110 (step S107). In the example of processing described above, a case in which the recognition target area is extracted when the skeleton information is saved and the motion information in the extracted recognition target area is specified has been described. The embodiment, however, is not limited thereto, and there may be a case in which the extraction is performed at arbitrary timing, for example. For example, the extraction may be performed in real time when the motion information is obtained.

As described above, according to the first embodiment, the obtaining circuitry 141 obtains image information of a subject carrying out a predetermined motion and the surroundings of the subject. The specification circuitry 142 specifies motion information of the subject carrying out the predetermined motion on the basis of predetermined features in the image information obtained by the obtaining circuitry 141. The motion information processing device 100 according to the first embodiment can therefore specify the motion information of the subject from information collected by the motion information collector 10, which can prevent false recognition of the subject.

As a result, the motion information processing device 100 allows proper rehab support using the motion information (skeleton information) of the subject in rehab support using the motion information collected by the motion information collector 10.

Furthermore, according to the first embodiment, the specification circuitry 142 extracts subject information indicating the subject as the predetermined feature from the image information obtained by the obtaining circuitry 141, and specifies the motion information of the subject carrying out the predetermined motion on the basis of the extracted subject information. The motion information processing device 100 according to the first embodiment can therefore properly extract the motion information of the subject contained in the information collected by the motion information collector 10.

Furthermore, according to the first embodiment, the specification circuitry 142 specifies information indicating a moving object contained in image information as subject information, and specifies motion information of the subject carrying out a predetermined motion on the basis of the extracted subject information. The motion information processing device 100 according to the first embodiment therefore allows easy extraction of motion information of the subject from information collected by the motion information collector 10.

Furthermore, according to the first embodiment, the specification circuitry 142 determines an object whose position changes in a three-dimensional space around the subject to be a moving object in the image information obtained over time by the obtaining circuitry 141. The motion information processing device 100 according to the first embodiment therefore allows easy extraction of a moving object.

Furthermore, according to the first embodiment, the display control circuitry 143 performs control to display a display image in which information indicating the subject is superimposed on the image information at a position corresponding to the motion information specified by the specification circuitry 142. The motion information processing device 100 according to the first embodiment therefore allows provision of a display image in which information is properly superimposed on a subject in a color image.

Second Embodiment

In the first embodiment described above, a case in which a moving object is used as a predetermined feature contained in image information is used has been described. In a second embodiment, a case in which a condition according to skeleton information of a human body is used will be described. Note that determination that will be described below may be used additionally in specifying motion information of a subject described in the first embodiment, or may be used alone.

Figure 10:
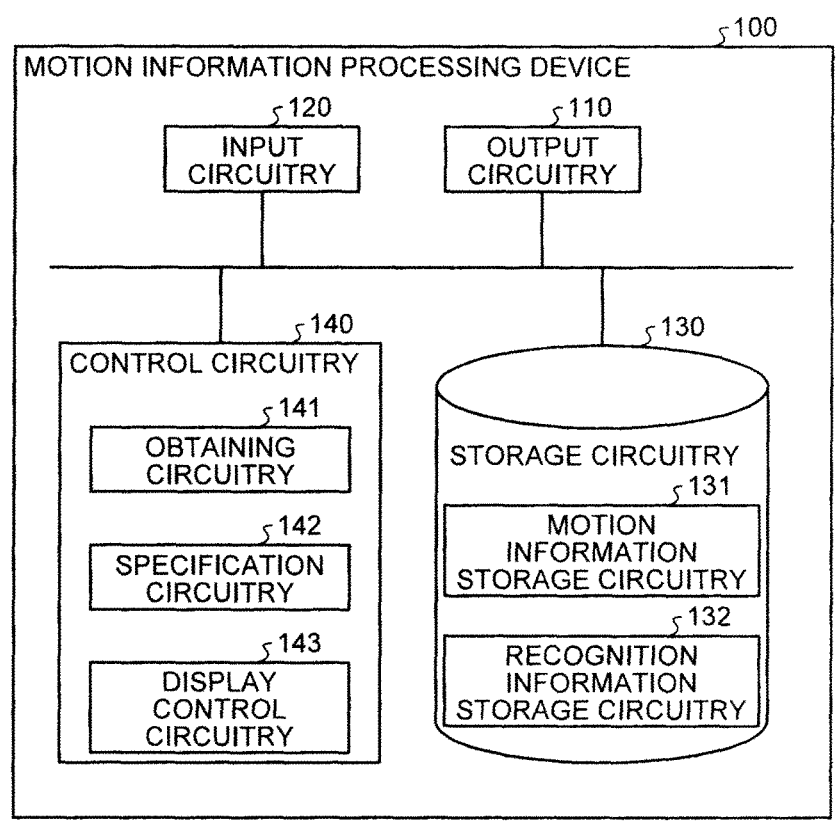
FIG. 10 is a block diagram illustrating a detailed example configuration of a motion information processing device according to a second embodiment.

FIG. 10 is a diagram illustrating an example of a detailed configuration of the motion information processing device 100 according to the second embodiment. The motion information processing device 100 according to the second embodiment illustrated in FIG. 10 is different from the motion information processing device 100 according to the first embodiment illustrated in FIG. 4 in that the storage circuitry 130 additionally includes a recognition information storage circuitry 132 and in the processing performed by the specification circuitry 142. Hereinafter, the description will be focused mainly on these differences.

The recognition information storage circuitry 132 stores recognition information for specifying skeleton information of a subject among skeleton information contained in motion information collected by the motion information collector 10. Specifically, the recognition information storage circuitry 132 stores information for identifying skeleton information indicating a human body skeleton among skeleton information data contained in motion information. FIGS. 11A and 11B are tables illustrating examples of recognition information stored by the recognition information storage circuitry 132 according to the second embodiment.

For example, the recognition information storage circuitry 132 stores recognition information in which a part and a range are associated as illustrated in FIG. 11A. Note that the "part" presented in FIG. 11A refers to a part of a human body. Furthermore, the "range" presented in FIG. 11A refers to a possible range of a human body skeleton. For example, the recognition information storage circuitry 132 stores recognition information of "part: height [cm], range: 100 cm-200 cm" as illustrated in FIG. 11A. The aforementioned information indicates that skeleton information with a "height" of "100 cm-200 cm" is skeleton information of a human body.

Similarly, the recognition information storage circuitry 132 stores recognition information of "part: arm length [cm], range: 60 cm-80 cm" as illustrated in FIG. 11A. In this manner, the recognition information storage circuitry 132 stores recognition information in which a range for identifying a part is set for each of various parts of a human body.

The recognition information storage circuitry 132 can also store recognition information in which a part, an average, and a variance are associated as illustrated in FIG. 11B. Note that the "part" presented in FIG. 11B refers to a part of a human body. The "average" presented in FIG. 11B refers to an average of the associated part as the skeleton of a human body. The "variance" presented in FIG. 11B refers to a variance of the associated part from the average.

For example, the recognition information storage circuitry 132 stores recognition information of "part: shoulder length [cm], average: 60 cm, variance: "1σ" as illustrated in FIG. 11B. The aforementioned information indicates that the "average" of the "shoulder length" as the human body skeleton is "60 cm" and the degree of "variance (possible range of the shoulder length)" is "1σ." Similarly, the recognition information storage circuitry 132 stores "part: length from head to waist [cm], average: 85 cm, variance: 2σ," "part: left arm angle, average: 80°, variance: 4σ" and so on as illustrated in FIG. 11B. In this manner, the recognition information storage circuitry 132 stores recognition information in which an average and a variance for identifying a part are set for each of various parts of a human body.

Note that the examples illustrated in FIGS. 11A and 11B are merely example, and the recognition information can be arbitrarily set. For example, the part, the range, the average, the variance, and the like can be arbitrarily set by the operator. The recognition information to be used as a condition can be used in combination in various manners. For example, there may be a case in which all of the information data presented in FIGS. 11A and 11B are essential, or a case in which only the height and the arm length are essential. Alternatively, for example, there may be a case in which either one of the shoulder length and the left arm angle needs to be satisfied.

Figure 12A:
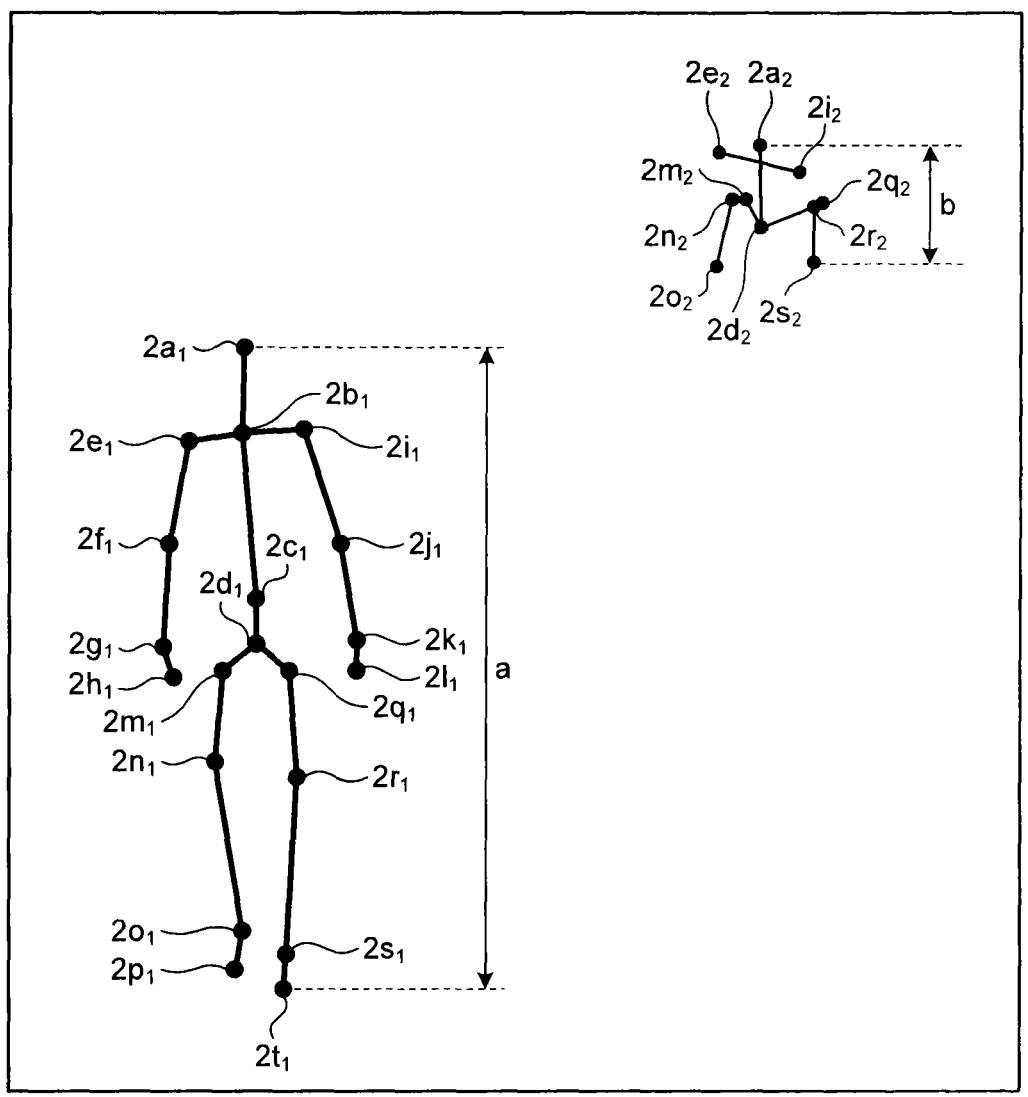
FIG. 12A is a diagram for explaining an example of processing performed by specification circuitry according to the second embodiment.
Figure 12B:
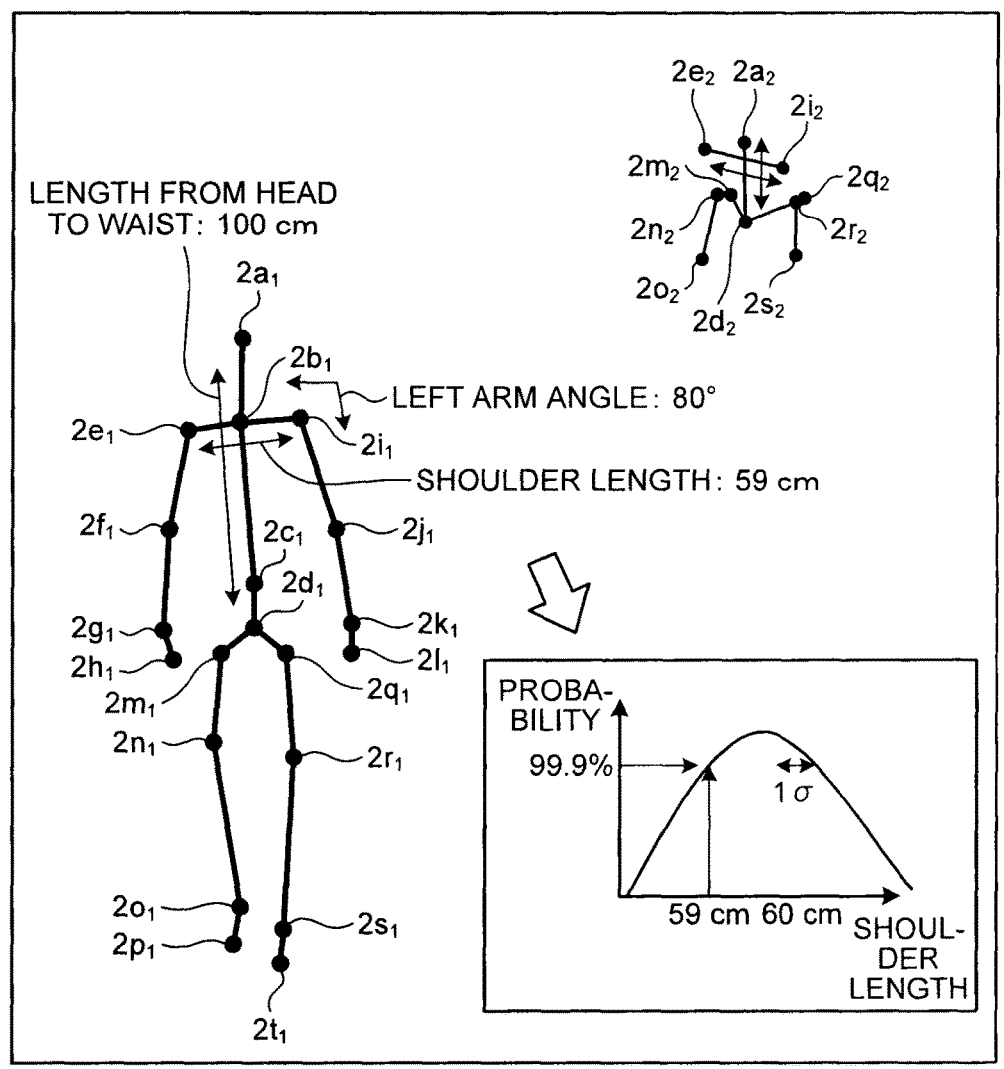
FIG. 12B is a diagram for explaining an example of processing performed by the specification circuitry according to the second embodiment.

The description refers back to FIG. 10, in which the specification circuitry 142 according to the second embodiment extracts information indicating a human body skeleton contained in image information as subject information, and specifies motion information of the subject carrying out a predetermined motion on the basis of the extracted subject information. Note that the specification circuitry 142 determines a set of joint points according to the human body structure to be information indicating a human body skeleton among information data of joint points contained in image information. FIGS. 12A and 12B are diagrams for explaining an example of processing performed by the specification circuitry 142 according to the second embodiment. Note that FIG. 12A illustrates processing in a case where the recognition information illustrated in FIG. 11A is used. FIG. 12B illustrates processing in a case where the recognition information illustrated in FIG. 11B is used.

First, the processing in the case where the recognition information illustrated in FIG. 11A is used will be described. The specification circuitry 142 according to the second embodiment reads out motion information of one frame collected by the motion information collector 10 and stored in the motion information storage circuitry 131 as illustrated in FIG. 12A, and carries out processing using the recognition information illustrated in FIG. 11A on skeleton information contained in the read motion information, for example. In one example, the specification circuitry 142 refers to the identification information in FIG. 11A "part: height [cm], range: 100 cm-200 cm" and carries out a specification process using the height information. Specifically, the specification circuitry 142 calculates a height "a" from the y coordinate value of the joint "$2a_1$" corresponding to the head and the y coordinate value of the joint "$2t_1$" corresponding to the tarsus of the left foot illustrated in FIG. 12A, for example. If the calculated height "a" is within the range of "100 cm-200 cm," the specification circuitry 142 then specifies skeleton information containing the joint "$2a_1$" and the joint "$2t_1$" as skeleton information of the subject.

The specification circuitry 142 also calculates a height "b" from the y coordinate value of the joint "$2a_2$" corresponding to the head and the y coordinate of the joint "$2s_2$" corresponding to the left ankle illustrated in FIG. 12A. If the calculated height "b" is not within the range of "100 cm-200 cm," the specification circuitry 142 specifies that skeleton information containing the joint "$2a_1$" and the joint "$2t_1$" is not skeleton information of the subject. Although specification using the height is illustrated in FIG. 12A, the embodiment is not limited thereto. Specifically, a specification process using any of the ranges of various parts can be carried out. Furthermore, although a case in which only the height is specified has been described in the example above, the embodiment is not limited thereto, and there may be a case in which motion information of the subject is specified by performing determination in a comprehensive manner using the ranges of two or more parts, for example.

In the example above, a case in which the height "a" and the height "b" are each calculated by using the y coordinates of the joint corresponding to the head and the joints corresponding to the left head has been described. While the motion information processing device 100 according to the present embodiment can increase the processing speed and allows efficient processing by calculating the heights by the simple method described above, the embodiment is not limited thereto, and the heights can be calculated by using three-dimensional coordinates of the joint corresponding to the head and the joint corresponding to the left foot, for example. For example, there may be a case in which the height "a" is calculated by using the x value, the y value, and the z value of the joint "$2a_1$" corresponding to the head and the x value, the y value, and the z value of the joint "$2t_1$" corresponding to the tarsus of the left foot. As a result, the motion information processing device 100 according to the present embodiment can achieve more accurate determination.

Next, processing in a case where the recognition information illustrated in FIG. 11B is used will be described. The specification circuitry 142 according to the second embodiment reads out motion information of one frame collected by the motion information collector 10 and stored in the motion information storage circuitry 131 as illustrated in FIG. 12B, and carries out processing using the recognition information illustrated in FIG. 11B on skeleton information contained in the read motion information, for example. In one example, the specification circuitry 142 refers to the identification information in FIG. 11B "part: shoulder length [cm], average: 60 cm, variance: "1σ" and carries out a specification process using the shoulder length information.

Specifically, the specification circuitry 142 calculates the "shoulder length: 59 cm" from the x coordinate value of the joint "$2e_1$" corresponding to the right shoulder and the x coordinate value of the joint "$2i_1$" corresponding to the left shoulder illustrated in FIG. 12B. The specification circuitry 142 then refers to the identification information "part: shoulder length [cm], average: 60 cm, variance: "1σ" and calculates the probability that the calculated "shoulder length: 59 cm" is a shoulder length of a human body. Specifically, the specification circuitry 142 calculates the probability of "99.9%" that the shoulder length is that of a human body as illustrated in FIG. 12B. Although a case in which the shoulder length is calculated by using the x coordinates of the joint corresponding to the right shoulder and the joint corresponding to the left shoulder has been described in the example above, the embodiment is not limited thereto, and there may be a case in which the shoulder length is calculated by using three-dimensional coordinates of the joint corresponding to the right shoulder and the joint corresponding to the left shoulder.

Note that the specification circuitry 142 may specify skeleton information of a subject on the basis of the calculated probability "99.9%," or may further calculate the likelihood of being a human body skeleton for a plurality of parts and specify the skeleton information on the basis of the calculated information. For example, the specification circuitry 142 calculates the "length from head to waist: 100 cm" from the joint "$2a_1$" corresponding to the head and the joint "$2d_1$" corresponding to the waist, and further calculates the "left arm angle: 80°" as illustrated in FIG. 12B.

The specification circuitry 142 then refers to the recognition information similarly to the case of the shoulder length, and calculates the "probability: 99.8%" of the "length from head to waist," for example. Similarly, the specification circuitry 142 refers to the recognition information, and calculates the "probability: 100%" of the "left arm angle," for example. The specification circuitry 142 then carries out a specification process of motion information of a subject by using the calculated probability. Note that the specification circuitry 142 carries out the specification process by comparing three probabilities (those of the shoulder length, the length from the head to the waist, and the left arm angle) with respective thresholds, or may carry out the specification process by comparing a value obtained by multiplying the three probabilities with a threshold.

For example, the specification circuitry 142 compares "99.7%" obtained by multiplying the "probability of shoulder length: 99.9%," "probability of length from head to waist: 99.8%" and "probability of left arm angle: 100%" with a predetermined threshold, and specifies the corresponding skeleton information when the value exceeds the predetermined threshold as skeleton information of a subject. Note that the predetermined threshold can be arbitrarily set. In the case where three probabilities are compared with respective thresholds, the corresponding skeleton information may be determined to be skeleton information of a subject if all of the three probabilities exceed the thresholds or the corresponding skeleton information may be determined to be skeleton information of a subject if two out of three probabilities exceed the thresholds. Note that these thresholds can also be arbitrarily set.

The specification circuitry 142 carries out processing similar to that described above by using skeleton information containing the joints ($2a_2$, $2d_2$, $2e_2$, $2i_2$, $2m_2$, $2n_2$, $2o_2$, $2q_2$, $2r_2$, and $2s_2$) in FIG. 12B. Specifically, the specification circuitry 142 calculates the shoulder length, the length from the head to the waist, or the like by using coordinates of the joints ($2a_2$, $2d_2$, $2e_2$, $2i_2$, $2m_2$, $2n_2$, $2o_2$, $2q_2$, $2r_2$, and $2s_2$) to obtain the probability of being a human body skeleton. The specification circuitry 142 the compares the probability with a predetermined threshold to determine whether or not the skeleton information containing the joints ($2a_2$, $2d_2$, $2e_2$, $2i_2$, $2m_2$, $2n_2$, $2o_2$, $2q_2$, $2r_2$, and $2s_2$) is skeleton information of a subject. For example, in the case of the skeleton information "joints ($2a_2$, $2d_2$, $2e_2$, $2i_2$, $2m_2$, $2n_2$, $2o_2$, $2q_2$, $2r_2$, and $2s_2$)" of the chair illustrated in FIG. 12B, the skeleton information is quite different from a human body skeleton, and thus the specification circuitry 142 determines that the skeleton information is not skeleton information of a subject.

Next, processing of the motion information processing device 100 according to the second embodiment will be described with reference to FIG. 13. FIG. 13 is a flowchart illustrating procedures of the processing performed by the motion information processing device 100 according to the second embodiment. As illustrated in FIG. 13, in the motion information processing device 100 according to the second embodiment, the obtaining circuitry 141 obtains motion information of a subject (step S201). The specification circuitry 142 then determines whether or not the false recognition preventing function is ON in the motion information collected by the motion information collector 10 (step S202).

If the false recognition preventing function is ON (Yes in step S202), the specification circuitry 142 reads out recognition information (step S203), and specifies motion information of a subject on the basis of the read recognition information (step S204). Subsequently, the specification circuitry 142 stores the specified motion information (skeleton information) in the motion information storage circuitry 131 (step S205).

If the false recognition preventing function is not ON in step S202 (No in step S202), the motion information is stored in the motion information storage circuitry 131 without the specification by the specification circuitry 142 (step S205). The display control circuitry 143 then performs control to generate a display image on the basis of the motion information stored in the motion information storage circuitry 131 and display the display image on the output circuitry 110 (step S206).

As described above, according to the second embodiment, the specification circuitry 142 extracts information indicating a human body skeleton contained in image information as subject information, and specifies motion information of the subject carrying out a predetermined motion on the basis of the extracted subject information. The motion information processing device 100 according to the second embodiment can therefore extract a human as a moving object, and prevent false recognition of a subject more accurately.

Furthermore, according to the second embodiment, the specification circuitry 142 determines a set of joint points according to the human body structure to be information indicating a human body skeleton among information data of joint points contained in image information. The motion information processing device 100 according to the second embodiment therefore enables extraction of a human as a moving object with high accuracy.

Third Embodiment

In a third embodiment, a case in which skeleton information of a subject is specified on the basis of the number of recognized joints among skeleton information data collected by the motion information collector 10 will be described. The third embodiment is different from the first and second embodiments in the processing of the specification circuitry 142. Hereinafter, the description will be focused mainly on this difference.

The specification circuitry 142 according to the third embodiment determines whether skeleton information is skeleton information of a subject on the basis of the number of joint points collected as the skeleton information among information of joint points contained in image information. In the case of the skeleton information illustrated in FIG. 5 as an example, the specification circuitry 142 compares skeleton information containing 20 joint points (joints $2a_1$ to $2t_1$) that have been recognized and skeleton information containing 10 joint points ($2a_2$, $2d_2$, $2e_2$, $2i_2$, $2m_2$, $2n_2$, $2o_2$, $2q_2$, $2r_2$, and $2s_2$) that have been recognized with respective predetermined thresholds to specify skeleton information of a subject. If a threshold is the number of joint points "15," for example, the specification circuitry 142 specifies the skeleton information containing 20 joint points (joint $2a_1$ to $2t_1$) that have been recognized as skeleton information of a subject.

If the likelihood of the recognition of the joint points is output from the motion information collector 10, the specification circuitry 142 counts the number of joint points with a predetermined likelihood, and compares the counted number with a threshold. If the number of joint points with the predetermined likelihood exceeds a predetermined threshold, the specification circuitry 142 then specifies the skeleton information with the number of joint points having the predetermined likelihood exceeding the predetermined threshold as the skeleton information of a subject, and stores the specified skeleton information in the motion information storage circuitry 131. In this process, the specification circuitry 142 can store the specified skeleton information in which the joints points are associated with information on the likelihood of recognition.

Figure 14:
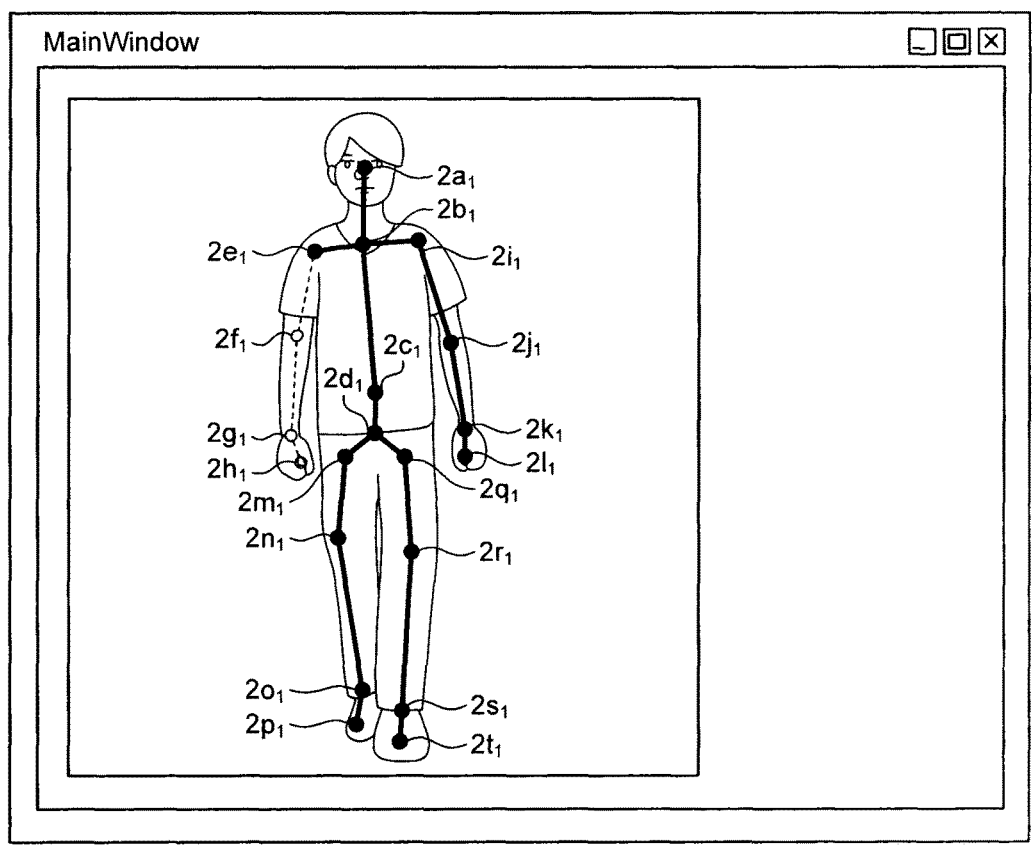
FIG. 14 is a diagram illustrating an example of a display image displayed by display control circuitry according to a third embodiment.

In this case, the display control circuitry 143 according to the third embodiment can generate a display image in which the information on the likelihood of the joint points is reflected, and display the generated display image. FIG. 14 is a diagram illustrating an example of the display image displayed by the display control circuitry 143 according to the third embodiment. As illustrated in FIG. 14, for example, the display control circuitry 143 generates a display image in which joint points having a predetermined likelihood of recognition of joint points are represented by black dots, information indicating bones between the black dots by solid lines is superimposed thereon, joint points not having the predetermined likelihood of recognition of joint points are represented by small white circles, and information indicating bones between the small white circles by broken lines, and displays the generated display image.

As described above, according to the third embodiment, the specification circuitry 142 specifies skeleton information of a subject on the basis of the number of recognized joint points. The motion information processing device 100 according to the third embodiment therefore enables specification of skeleton information of a subject by a simple method.

Fourth Embodiment

In the first to third embodiments described above, a case in which skeleton information of a subject is specified from the entire area from which motion information is collected by the motion information collector 10 has been described. In a fourth embodiment, a case in which a recognition target area is specified by an operator will be described. The fourth embodiment is different from the first to third embodiments in an instruction received by the input circuitry 120 and in the processing performed by the specification circuitry 142. Hereinafter, the description will be focused mainly on these differences.

The input circuitry 120 according to the fourth embodiment receives a specification operation for specifying a predetermined area in image information. Specifically, the input circuitry 120 receives an input operation for specifying a recognition target area for recognition of a subject.

The specification circuitry 142 according to the fourth embodiment uses information contained within a predetermined area received by the input circuitry 120 to determine motion information of a subject carrying out a predetermined motion to be a predetermined feature from information contained in the predetermined area. Specifically, the specification circuitry 142 determines skeleton information contained in the recognition target area received by the input circuitry 120 to be the skeleton information of the subject.

FIG. 15 is a diagram for explaining an example of processing performed by the input circuitry 120 and the specification circuitry 142 according to the fourth embodiment. The input circuitry 120 receives an input operation for specifying a recognition target area R2 as illustrated in (B) of FIG. 15 on an image illustrated in (A) of FIG. 15, for example. When the recognition target area R2 illustrated in (B) of FIG. 15 is specified, the specification circuitry 142 then determines skeleton information contained in the specified recognition target area R2 to be the skeleton information of the subject. As a result, even when skeleton information corresponding to the chair illustrated in FIG. 15 is collected, for example, the skeleton information of the subject can be reliably determined.

As described above, according to the fourth embodiment, the input circuitry 120 receives a specification operation for specifying a predetermined area in image information. The specification circuitry 142 then determines motion information of a subject carrying out a predetermined motion to be a predetermined feature within the area received by the input circuitry 120. The motion information processing device 100 according to the fourth embodiment can therefore specify a recognition target area in a simple manner and easily determine skeleton information of a subject.

Fifth Embodiment

In the fourth embodiment described above, a case in which a recognition target area is specified through the input circuitry 120 has been described. In a fifth embodiment, a case in which a recognition target area is set on the basis of information within an image will be described. The fifth embodiment is different from the first to fourth embodiments in the processing performed by the specification circuitry 142. Hereinafter, the description will be focused mainly on this difference.

The specification circuitry 142 according to the fifth embodiment extracts a set item set for a subject in advance as subject information, and determines motion information of the subject carrying out a predetermined motion on the basis of the extracted subject information. Specifically, first, the subject carrying out rehab wears a thing that functions as a mark and carries out rehab. The specification circuitry 142 extracts the mark contained in an image, set a recognition target area on the basis of the extracted mark, and determines skeleton information within the set recognition target area to be skeleton information of the subject.

FIG. 16 is a diagram for explaining an example of processing performed by the specification circuitry 142 according to the fifth embodiment. FIG. 16 illustrates a case in which marks set in advance are worn on the feet of the subject. The subject carries out gait training with the marks of a predetermined color (red, for example) on his/her feet as illustrated in (A) of FIG. 16, for example. The specification circuitry 142 extracts the marks worn on the feet of the subject from color image information collected by the motion information collector 10. The specification circuitry 142 then calculates a midpoint $P_1$ that is the center of the width between the extracted marks on the feet as illustrated in (A) of FIG. 16, and determines a width defining a predetermined distance to the left and to the right from the calculated midpoint $P_1$.

When the distance between the marks on the feet is "15 cm," for example, the specification circuitry 142 determines "45 cm" that is three times the distance to be the width of a recognition target area R3. Specifically, the specification circuitry 142 determines "22.5 cm" to the left and to the right from the midpoint $P_1$ to be the width of the recognition target area R3. The specification circuitry 142 then determines the length from a lower end $P_2$ of the marks on the feet to an upper end $P_3$ of the color image information to be the length of the recognition target area R3.

Specifically, the specification circuitry 142 sets the recognition target area R3 in the color image information as illustrated in (B) of FIG. 16, and determines skeleton information contained in the set recognition target area R3 to be skeleton information of the subject. Note that the example illustrated in FIG. 16 is only an example, and the embodiment is not limited thereto. For example, the marks set on the subject in advance may also be set in various manners other than the color thereof. In one example, there may be a case in which the subject wears things of a predetermined shape.

Note that information on a mark set on the subject in advance is stored in the storage circuitry 130 in advance, and the specification circuitry 142 reads out the information on the mark stored in the storage circuitry 130 and extracts the mark contained in the color image information.

As described above, according to the fifth embodiment, the specification circuitry 142 extracts a set item set for a subject in advance as subject information, and determines motion information of the subject carrying out a predetermined motion on the basis of the extracted subject information. The motion information processing device 100 according to the fifth embodiment therefore allows a recognition target area to be set in a simple manner.

Sixth Embodiment

While the first to fifth embodiments have been described above, various different embodiments other than the first to fifth embodiments can be employed.

In the first to fifth embodiments described above, a case in which motion information collected in a state in which rehab is being carried out has been described. The embodiment, however, is not limited thereto, and there may be a case in which various information data are extracted from motion information during rehab on the basis of information before the rehab is carried out, for example.

FIG. 17 is a diagram for explaining an example of processing performed by the specification circuitry 142 according to the sixth embodiment. The specification circuitry 142 obtains the depth of a "T-second" frame that is image information (motion information) in a state before the rehab is carried out as a reference value as illustrated in (A) of FIG. 17, for example. The specification circuitry 142 then obtains the depth of a "(T+t)-second" frame that is image information (motion information) in a state in which the rehab is being carried out as illustrated in (B) of FIG. 17. In this process, the specification circuitry 142 can extract a part in which the depth has changed in the "(T+t)-second" frame from that in the "T-second" frame to reduce information to be processed. For example, as illustrated in FIG. 17, the chair that is contained in both images and whose depth information does not change can be ignored.

As a result, objects that are at a shallower or deeper position than the reference value can be easily determined, and objects whose depth has been changed to be shallower, deeper or to the left or right during rehab can be easily extracted, for example. Note that the aforementioned processing can be carried out in combination with the first to fifth embodiments where appropriate.

Furthermore, in the first to fifth embodiments described above, a case in which gain training is carried out as rehab has been described. The motion information processing device 100 according to the present application, however, can also be applied to rehab exercises other than gait training. For example, the specification circuitry 142 can also determine skeleton information of a subject carrying out range of motion exercise.

As described above, according to the first to sixth embodiments, the motion information processing device according to the present embodiments can therefore configured prevent false recognition of a subject.

Seventh Embodiment

As described above, in the first to sixth embodiments, a case of supporting rehabilitation by allowing prevention of falsely recognizing a person or object other than the person carrying out a predetermined motion has been described. However, a person who is photographed is not always the subject. Specifically, if a person is within the photographed range of the motion information collector 10, the person is photographed by the motion information collector 10 whether the person is the subject, a caregiver, or even a person not involved in rehab, for example. Thus, in seventh to tenth embodiments below, a case of providing a motion information processing device capable of determining whether or not a digitally recorded motion of a person is that of a subject of rehabilitation will be described. Although the person carrying out a predetermined motion has been referred to as a "subject" in the first to sixth embodiments, a person that is a subject of rehabilitation will be referred to as a "subject" in the seventh to tenth embodiments.

Figure 18A:
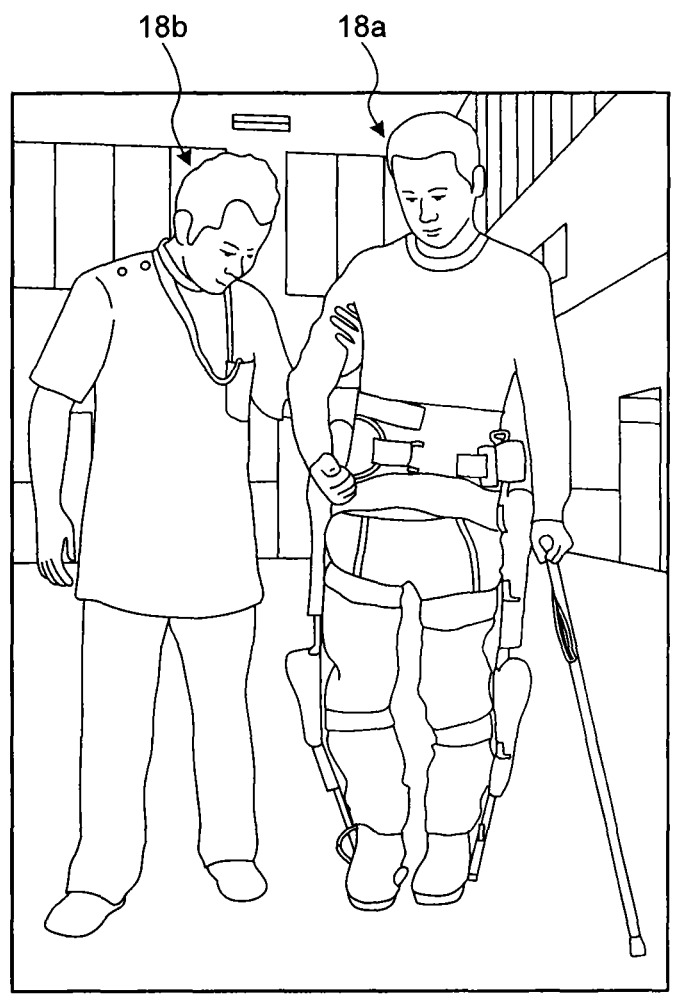
FIG. 18A is a diagram illustrating an example of a distance image taken by distance image collection circuitry.
Figure 18B:
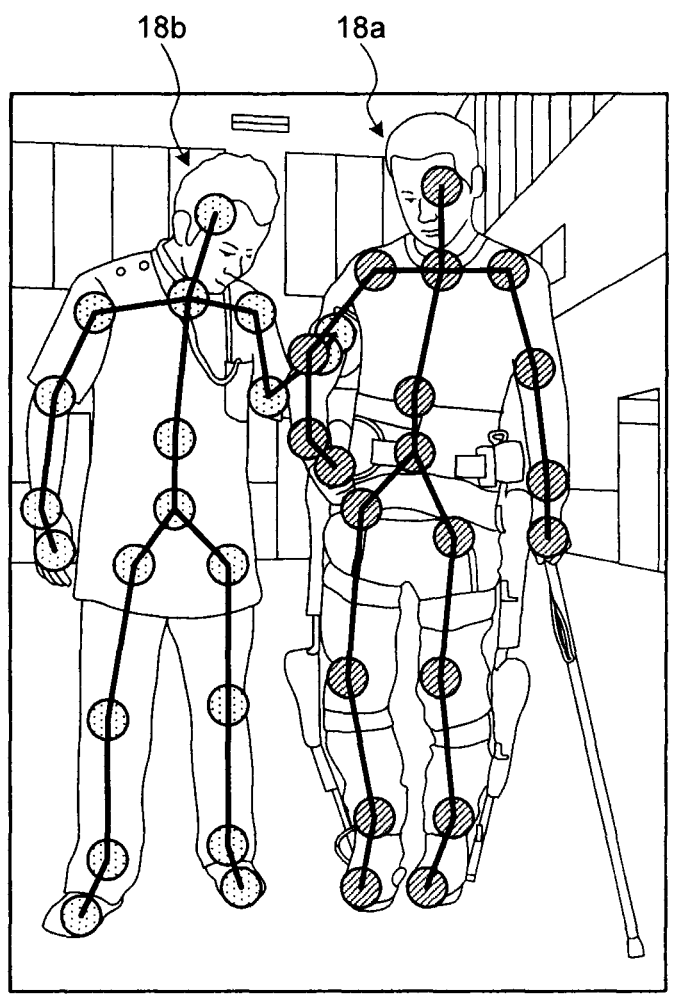
FIG. 18B is a diagram illustrating an example of a distance image taken by the distance image collection circuitry.

FIGS. 18A and 18B are diagrams illustrating an example of a distance image taken by the distance image collection circuitry 12. FIGS. 18A and 18B illustrates a case in which a person 18a (subject) receives assistance from a person 18b (caregiver) in rehab. Specifically, the person 18a (subject) is supported by the left hand of the person 18b (caregiver) on his/her right arm to carry out gait training. Note that, in FIGS. 18A and 18B, a distance image expressed by color shadings according to the distances is expressed by line drawing for the purpose of illustration.

As illustrated in FIG. 18A, the motion information collector 10 takes a distance image containing the person 18a (subject) and the person 18b (caregiver) as objects. In generating motion information from the distance image, the motion information collector 10 recognizes the person 18a and the person 18b as individual persons, not as a subject and a caregiver and generates motion information of the respective persons as illustrated in FIG. 18B. Thus, for analyzing motion relating to rehab of the subject by using the motion information generated here, it is necessary to specify the person who is the subject. Furthermore, the motion of caregiver may be falsely evaluated when the motion of the subject should be analyzed.

Thus, a motion information processing device 200 according to the seventh embodiment performs processing described below to determine whether or not a digitally recorded motion of a person is that of a subject of rehabilitation.

Furthermore, the motion information processing device 200 according to the seventh embodiment may analyze the motion of a caregiver to support the caregiver so as to indirectly support the subject assisted by the caregiver. In such a case, the motion information processing device 200 according to the seventh embodiment may determine whether or not the digitally recorded motion of a person is that of a caregiver by performing the processing described below.

Figure 19:
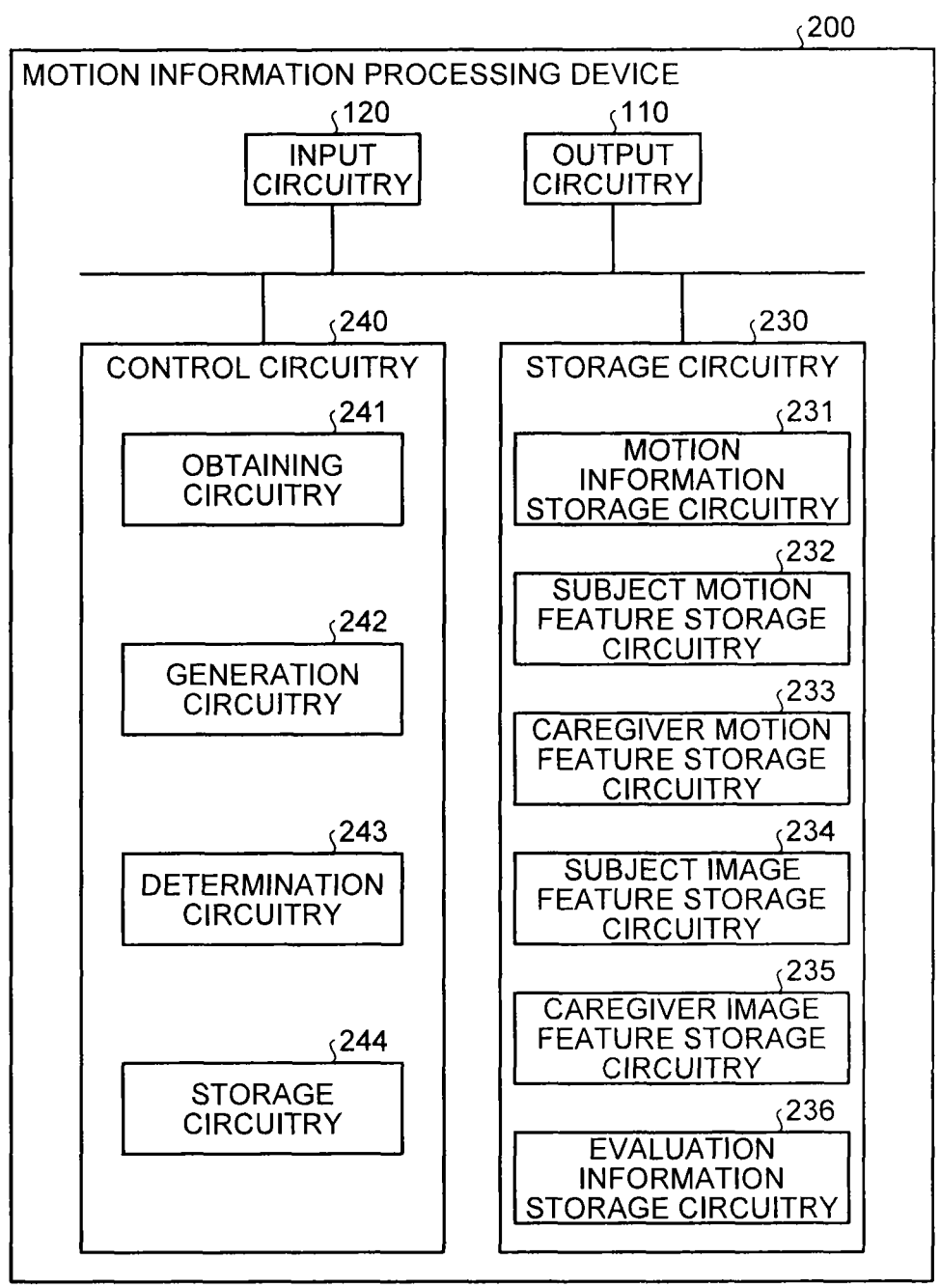
FIG. 19 is a block diagram illustrating a detailed example configuration of a medical information processing device according to a seventh embodiment.

FIG. 19 is a block diagram illustrating a detailed example configuration of the motion information processing device 200 according to the seventh embodiment. As illustrated in FIG. 19, in the motion information processing device 200, storage circuitry 230 includes motion information storage circuitry 231, subject motion feature storage circuitry 232, caregiver motion feature storage circuitry 233, subject image feature storage circuitry 234, caregiver image feature storage circuitry 235, and evaluation information storage circuitry 236.

The motion information storage circuitry 231 stores various information data collected by the motion information collector 10. For example, the motion information storage circuitry 231 stores information in which motion information and color image information are associated with each other for a motion of a person. The motion information is skeleton information of each frame generated by the motion information generation circuitry 14. Coordinates of joints in the skeleton information and pixel positions in the color image information are associated with each other in advance. Photographing time information in the skeleton information and photographing time information in the color image information are also associated with each other in advance. Furthermore, for example, the motion information and the color image information are stored in the motion information storage circuitry 231 each time the motion information and the color image information are collected by the motion information collector 10.

The motion information storage circuitry 231 stores the motion information for each rehab such as gait training or range of motion exercise that is carried out, for example. Note that motions of multiple persons may be included in one exercise of rehab. In a specific example, as illustrated in FIG. 4A, when a subject carries out gait training with assistance from a caregiver, one gait training is carried out by combination of the motions of the subject and the caregiver. In such a case, the motion information storage circuitry 231 associates skeleton information data of multiple persons generated from distance image information of the same frame with one another, and stores the associated information as one motion information item. Thus, the motion information indicates motions of multiple persons at the same time. The motion information storage circuitry 231 stores motion information in association with photographing start time information on the time when photographing of the motion is started, for example. Although a case in which motion information indicates motions of multiple persons will be described below, the embodiment is not limited thereto, and there may be a case in which the motion information indicates a motion of one person.

The subject motion feature storage circuitry 232 stores subject motion feature information indicating a feature of the motion of the subject. For example, the subject motion feature storage circuitry 232 stores information in which a motion ID (identification) and the subject motion feature information are associated with each other. In the information, the motion ID is identification information for identifying a motion, and a number is allotted thereto each time a motion is defined by the designer of the motion information processing device 200. The subject motion feature information is information indicating a feature of a motion of a subject, and is defined by the designer of the motion information processing device 200 in advance, for example.

FIG. 20 is a table illustrating an example of information stored in the subject motion feature storage circuitry 232. In the first record of FIG. 20, a motion ID "11" and subject motion feature information "dragging one's leg" are associated. Specifically, the subject motion feature storage circuitry 232 stores one of the features of the motion of the subject being "dragging one's leg" as the motion with the motion ID "11." The subject motion feature information "dragging one's leg" is determined according to whether or not the maximum change in the y coordinate of a tarsus (joint 2p or joint 2t) during the motion is smaller than 1 cm, for example. In the second record of FIG. 20, a motion ID "12" and subject motion feature information "walking with poor posture" are associated. Specifically, the subject motion feature storage circuitry 232 stores one of the features of the motion of the subject being "walking with poor posture" as the motion with the motion ID "12." The subject motion feature information "walking with poor posture" is determined according to whether or not the average of an angle between the backbone (a line connecting the joint 2b and the joint 2c) and the vertical direction during the motion is equal to or larger than 3°, for example. In the third record of FIG. 20, a motion ID "13" and subject motion feature information "walking slowly" are associated. Specifically, the subject motion feature storage circuitry 232 stores one of the features of the motion of the subject being "walking slowly" as the motion with the motion ID "13." The subject motion feature information "walking slowly" is determined according to whether or not the maximum value of the moving speed of the waist (joint 2c) during the motion is lower than 1 [m/s], for example. As for the other records, the subject motion feature storage circuitry 232 similarly stores the motion ID and the subject motion feature information in association with each other. Although the subject motion feature storage circuitry 232 used when gait training is carried out is presented here as an example, the embodiment is not limited thereto, and when range of motion exercise is carried out, a subject motion feature storage circuitry 232 in which a feature of a motion of a subject carrying out range of motion exercise is stored may be used. Alternatively, the subject motion feature storage circuitry 232 may store a feature of a motion of a subject carrying out gait training and a feature of a motion of a subject carrying out range of motion exercise without any distinction therebetween.

The caregiver motion feature storage circuitry 233 stores caregiver motion feature information indicating a feature of a motion of a caregiver. For example, the caregiver motion feature storage circuitry 233 stores information in which a motion ID and the caregiver motion feature information are associated with each other. The caregiver motion feature information is information indicating a feature of a motion of a caregiver, and is defined by the designer of the motion information processing device 200 in advance.

FIG. 21 is a table illustrating an example of information stored in the caregiver motion feature storage circuitry 233. In the first record of FIG. 21, a motion ID "21" and caregiver motion feature information "supporting subject's arm" are associated. Specifically, the caregiver motion feature storage circuitry 233 stores one of the features of the motion of the caregiver being "supporting subject's arm" as the motion with the motion ID "21." The caregiver motion feature information "supporting subject's arm" is determined according to whether or not a hand (the joint 2h or the joint 2l) of a person is within 5 cm from an arm (a line connecting the joint 2e and the joint 2f or a line connecting the joint 2i and the joint 2j) of another person for a predetermined time during the motion, for example. In the second record of FIG. 21, a motion ID "22" and caregiver motion feature information "walking with good posture" are associated. Specifically, the caregiver motion feature storage circuitry 233 stores one of the features of the motion of the caregiver being "walking with good posture" as the motion with the motion ID "22." The caregiver motion feature information "walking with good posture" is determined according to whether or not the average of an angle between the backbone (a line connecting the joint 2b and the joint 2c) and the vertical direction during the motion is smaller than 3°, for example. In the third record of FIG. 21, a motion ID "23" and caregiver motion feature information "walking fast" are associated. Specifically, the caregiver motion feature storage circuitry 233 stores one of the features of the motion of the caregiver being "walking fast" as the motion with the motion ID "23." The caregiver motion feature information "walking fast" is determined according to whether or not the maximum value of the moving speed of the waist (joint 2c) during the motion is equal to or higher than 1 [m/s], for example. As for the other records, the caregiver motion feature storage circuitry 233 similarly stores the motion ID and the caregiver motion feature information in association with each other. Although the caregiver motion feature storage circuitry 233 used when gait training is carried out is presented here as an example, the embodiment is not limited thereto, and when range of motion exercise is carried out, a caregiver motion feature storage circuitry 233 in which a feature of a motion of a subject carrying out range of motion exercise is stored may be used. Alternatively, the caregiver motion feature storage circuitry 233 may store a feature of a motion of a subject carrying out gait training and a feature of a motion of a subject carrying out range of motion exercise without any distinction therebetween.

The subject image feature storage circuitry 234 stores subject feature information indicating a physical feature of a subject or a feature of an object accompanying a subject. For example, the subject image feature storage circuitry 234 stores subject image feature information indicating a feature of an image of a subject. For example, the subject image feature storage circuitry 234 stores information in which an equipment ID and subject equipment feature information are associated with each other. In the information, the equipment ID is identification information for identifying equipment, and a number is allotted thereto each time equipment is defined by the designer of the motion information processing device 200. The subject equipment feature information is information indicating a feature of equipment of a subject, and is image information of equipment that can be used in pattern matching, for example. The subject equipment feature information is defined in advance by the designer of the motion information processing device 200. Note that the subject image feature storage circuitry 234 is an example of a subject feature storage circuitry.

FIG. 22 is a table illustrating an example of information stored in the subject image feature storage circuitry 234. In the first record of FIG. 22, an equipment ID "11" and subject equipment feature information "crutch" are associated. Specifically, the subject image feature storage circuitry 234 stores one of the features of the image of the subject being image information of a "crutch" as equipment with the equipment ID "11." In the second record of FIG. 22, an equipment ID "12" and subject equipment feature information "cast" are associated. Specifically, the subject image feature storage circuitry 234 stores one of the features of the image of the subject being image information of a "cast" as equipment with the equipment ID "12." In the third record of FIG. 22, an equipment ID "13" and subject equipment feature information "wheel chair" are associated. Specifically, the subject image feature storage circuitry 234 stores one of the features of the image of the subject being image information of a "wheel chair" as equipment with the equipment ID "13." Although the subject image feature storage circuitry 234 used when gait training is carried out is presented here as an example, the embodiment is not limited thereto, and when range of motion exercise is carried out, a subject image feature storage circuitry 234 in which a feature of equipment of a subject carrying out range of motion exercise is stored may be used. Alternatively, the subject image feature storage circuitry 234 may store a feature of a motion of a subject carrying out gait training and a feature of equipment of a subject carrying out range of motion exercise without any distinction therebetween.

The caregiver image feature storage circuitry 235 stores caregiver feature information indicating a physical feature of a caregiver or a feature of an object accompanying a caregiver. For example, the caregiver image feature storage circuitry 235 stores caregiver image feature information indicating a feature of an image of a caregiver. For example, the caregiver image feature storage circuitry 235 stores information in which an equipment ID and caregiver equipment feature information are associated with each other. In the information, the caregiver equipment feature information is information indicating a feature of equipment of a caregiver, and is image information of equipment that can be used in pattern matching, for example. The caregiver equipment feature information is defined in advance by the designer of the motion information processing device 200. Note that the caregiver image feature storage circuitry 235 is an example of a caregiver feature storage circuitry.

Figures 23, 24:
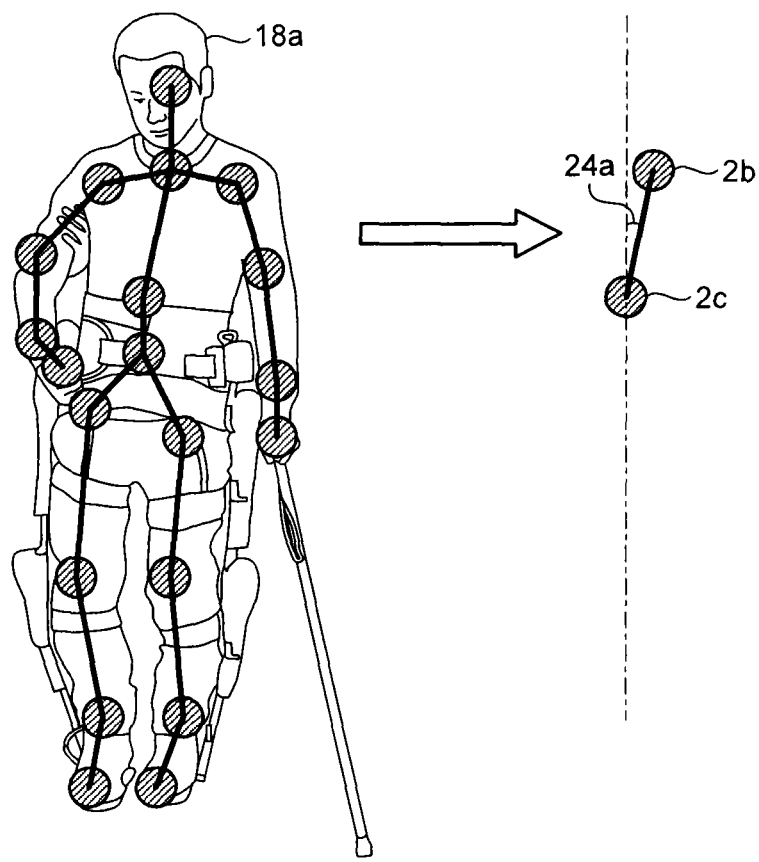
FIG. 23 is a table illustrating an example of information stored in caregiver image feature storage circuitry.
FIG. 24 is a diagram for explaining processing performed by generation circuitry.

FIG. 23 is a table illustrating an example of information stored in the caregiver image feature storage circuitry 235. In the first record of FIG. 23, an equipment. ID "21" and caregiver equipment feature information "stethoscope" are associated. Specifically, the caregiver image feature storage circuitry 235 stores one of the features of the image of the caregiver being image information of a "stethoscope" as equipment with the equipment ID "21." In the second record of FIG. 23, an equipment ID "22" and caregiver equipment feature information "white coat" are associated. Specifically, the caregiver image feature storage circuitry 235 stores one of the features of the image of the caregiver being image information of a "white coat" as equipment with the equipment ID "22." In the third record of FIG. 23, an equipment ID "23" and caregiver equipment feature information "nameplate" are associated. Specifically, the caregiver image feature storage circuitry 235 stores one of the features of the image of the caregiver being image information of a "nameplate" as equipment with the equipment ID "23."

The evaluation information storage circuitry 236 stores information in which evaluation information and a determination result are associated for each subject. In the information, the evaluation information is information for evaluating a motion of a person in rehabilitation. For example, the evaluation information is a posture with which or speed at which a subject or a caregiver walk, or the like. The evaluation information is generated by generation circuitry 242, which will be described later. The determination result is a result of determination performed by determination circuitry 243, which will be described later, and any one of a subject, a caregiver, and indeterminable is stored, for example.

The description refers back to FIG. 19. In the motion information processing device 200, control circuitry 240 includes obtaining circuitry 241, the generation circuitry 242, the determination circuitry 243, and storage circuitry 244.

The obtaining circuitry 241 obtains motion information to be evaluated. For example, when an input specifying motion information to be evaluated is received from the input circuitry 120, the obtaining circuitry 241 obtains the specified motion information and associated color image information from the motion information storage circuitry 231.

In one example, when specification of photographing start time information of motion information to be evaluated is received, the obtaining circuitry 241 obtains the motion information and color image information associated with the motion information from the motion information storage circuitry 231. Note that the motion information may contain skeleton information data of multiple persons generated from distance image information of the same frame or may contain skeleton information of one person.

The generation circuitry 242 generates evaluation information for evaluating rehabilitation from the motion information obtained by the obtaining circuitry 241. For example, the generation circuitry 242 calculates the postures with which and the speeds at which a subject and a caregiver walk. In a case where the motion information obtained by the obtaining circuitry 241 contains skeleton information data of multiple persons generated from distance image information of the same frame, the generation circuitry 242 generates evaluation information for skeleton information of each individual person. The generation circuitry 242 outputs the generated evaluation information to the storage circuitry 244.

FIG. 24 is a diagram for explaining processing performed by the generation circuitry 242. FIG. 24 explains a case in which the posture with which and the speed at which each of the person 18a and the person 18b walks are calculated on the basis of motion information collected in the gait training in FIG. 18A. For example, the generation circuitry 242 extracts the coordinates of the joint 2b and the coordinates of the joints 2c of the person 18a of the respective frames from the motion information obtained by the obtaining circuitry 241. The generation circuitry 242 regards a line connecting the extracted joint 2b and joint 2c as the backbone of the person 18a, and obtains an angle 24a between the backbone and the vertical direction for each frame. The generation circuitry 242 then calculates an average value of the angles 24a in multiple frames while gait training is carried out as the posture with which the person 18a walks.

The generation circuitry 242 also calculates the posture with which the person 18b walks similarly to that of the person 18a.

In addition, for example, the generation circuitry 242 obtains the moving distance [m] that the coordinates of the joint 2c corresponding to the waist of the person 18a have moved at predetermined time intervals (0.5 seconds, for example). The generation circuitry 242 then calculates the moving speed [m/s] of the person 18a at predetermined time intervals on the basis of the moving distance per the predetermined time. The generation circuitry 242 then calculates an average value of the moving speed of the person 18a while the person 18a is carrying out gait training as the speed at which the person 18a walks. The generation circuitry 242 also calculates the speed at which the person 18b walks similarly to that of the person 18a.

Although a case in which the posture and the speed of walk during gait training are calculated as evaluation information generated by the generation circuitry 242 has been described here, the embodiment is not limited thereto. For example, the generation circuitry 242 may select and calculate other evaluation information as appropriate depending on the content of functional exercises of rehabilitation or the condition of the subject.

The determination circuitry 243 determines whether or not a person associated with motion information obtained by the obtaining circuitry 241 is a subject of rehabilitation by using information indicating a feature of a subject. For example, the determination circuitry 243 refers to the subject motion feature information stored in the subject motion feature storage circuitry 232 as information indicating a feature of a subject, and determines whether or not the person associated with the motion information obtained by the obtaining circuitry 241 is a subject.

For example, the determination circuitry 243 determines whether or not a person associated with the motion information obtained by the obtaining circuitry 241 is a subject. The determination circuitry 243 also determines whether or not a person associated with the motion information obtained by the obtaining circuitry 241 is a caregiver. If skeleton information data of multiple persons generated from distance image information of the same frame are contained in the motion information obtained by the obtaining circuitry 241, the determination circuitry 243 determines whether or not the person is a subject or whether or not the person is a caregiver for skeleton information of each individual person. The determination circuitry 243 outputs the result of determination to the storage circuitry 244. In the following, processing of the determination circuitry 243 will be concretely described.

First, processing for determining whether or not a person is a subject will be described. The determination circuitry 243 selects one unprocessed record from records in the subject motion feature storage circuitry 232 and the subject image feature storage circuitry 234, for example. The determination circuitry 243 then determines whether or not the obtained motion information and color image information satisfy the condition of the selected record.

Here, a case in which the record with the motion ID "11" has been selected from the subject motion feature storage circuitry 232 will be described. In this case, as illustrated in FIG. 20, the determination circuitry 243 determines whether or not the motion information obtained by the obtaining circuitry 241 corresponds to the subject motion feature information "dragging one's leg." Specifically, the determination circuitry 243 extracts the y coordinates of a tarsus (joint 2p or joint 2t) from the frames contained in the obtained motion information. The determination circuitry 243 then calculates the difference between the largest value and the smallest value of the extracted y coordinates as a maximum change amount. If the calculated maximum change amount is smaller than 1 cm, the determination circuitry 243 determines that the obtained motion information corresponds to the subject motion feature information, that is, the subject is dragging his/her leg.

In addition, a case in which the record with the motion ID "12" has been selected from the subject motion feature storage circuitry 232 will be described. In this case, as illustrated in FIG. 20, the determination circuitry 243 determines whether or not the motion information obtained by the obtaining circuitry 241 corresponds to the subject motion feature information "walking with poor posture." If the walking posture has been calculated by the generation circuitry 242, the determination circuitry 243 obtains the posture with which a person contained in the obtained motion information walks from the generation circuitry 242. If the obtained walking posture is not smaller than 3°, the determination circuitry 243 then determines that the obtained motion information corresponds to the subject motion feature information, that is, the subject is walking with poor posture. If the walking posture has not been calculated by the generation circuitry 242, the determination circuitry 243 may perform the same processing as that described above with reference to the generation circuitry 242 to calculate the walking posture.

In addition, a case in which the record with the motion ID "13" has been selected from the subject motion feature storage circuitry 232 will be described. In this case, as illustrated in FIG. 20, the determination circuitry 243 determines whether or not the motion information obtained by the obtaining circuitry 241 corresponds to the subject motion feature information "walking slowly." If the walking speed has been calculated by the generation circuitry 242, the determination circuitry 243 obtains the moving speed [m/s] at which a person contained in the obtained motion information walks at predetermined time intervals (0.5 seconds, for example) from the generation circuitry 242. If the maximum moving speed of the obtained moving speed is lower than 1 [m/s], the determination circuitry 243 then determines that the obtained motion information corresponds to the subject motion feature information, that is, the subject is walking slowly. If the walking speed has not been calculated by the generation circuitry 242, the determination circuitry 243 may perform the same processing as that described above with reference to the generation circuitry 242 to calculate the walking speed.

In addition, a case in which the record with the equipment ID "11" has been selected from the subject image feature storage circuitry 234 will be described. In this case, as illustrated in FIG. 22, the determination circuitry 243 carries out pattern matching between color image information obtained by the obtaining circuitry 241 and subject equipment feature information "crutch." When an image of a crutch is extracted from the color image information as a result of pattern matching, the determination circuitry 243 determines whether or not the extracted pixel positions of the crutch overlap with coordinates in skeleton information contained in motion information to be evaluated. If the pixel positions of the crutch overlap with the coordinates in the skeleton information, the determination circuitry 243 determines that the obtained color image information corresponds to the subject equipment feature information, that is, the subject holds a crutch. As for the other records, the determination circuitry 243 similarly determines whether or not the obtained color image information corresponds to the subject equipment feature information.

As described above, the determination circuitry 243 determines whether or not the obtained motion information and color image information corresponds to the selected record. If it is determined that the obtained information corresponds to the selected record, the determination circuitry 243 increments a held subject feature number n by 1. The held subject feature number n represents the number of features as a subject that a person associated with motion information to be evaluated has. As for the other unprocessed records, the determination circuitry 243 similarly determines whether or not the obtained motion information and color image information correspond to the record. When the held subject feature number n has reached 5, the determination circuitry 243 determines that the person associated with the motion information to be evaluated to be a subject. If the held subject feature number n does not reach 5 when the determination circuitry 243 has performed determination on all the records in the subject motion feature storage circuitry 232 and the subject image feature storage circuitry 234, the determination circuitry 243 determines that the person associated with the motion information to be evaluated is not a subject. Although a case in which the threshold for the held subject feature number n for determining whether or not a person is a subject is 5 has been presented as an example, the embodiment is not limited thereto, and the threshold may be set to any value by the operator.

Furthermore, although a case in which the held subject feature number n is incremented by 1 when information corresponds to a record has been described, the embodiment is not limited thereto, and each record may be weighted, for example.

Next, processing for determining whether or not a person is a caregiver will be described. The determination circuitry 243 selects one unprocessed record from records in the caregiver motion feature storage circuitry 233 and the caregiver image feature storage circuitry 235, for example. The determination circuitry 243 then determines whether or not the obtained motion information and color image information correspond to the selected record.

Here, a case in which the record with the motion ID "21" has been selected from the caregiver motion feature storage circuitry 233 will be described. In this case, as illustrated in FIG. 21, the determination circuitry 243 determines whether or not the motion information obtained by the obtaining circuitry 241 corresponds to the caregiver motion feature information "supporting subject's arm." Specifically, the determination circuitry 243 extracts the coordinates of a hand (joint 2h or joint 2l) from the frames contained in the obtained motion information. If an arm (a line connecting the joint 2e and the joint 2f or a line connecting the joint 2i and the joint 2j) of another person is present within 5 cm from the obtained hand for a predetermined time during gait training, the determination circuitry 243 then determines that the obtained motion information corresponds to the caregiver motion feature information, that is, the caregiver is supporting the subject's arm.

In addition, a case in which the record with the motion ID "22" has been selected from the caregiver motion feature storage circuitry 233 will be described. In this case, as illustrated in FIG. 21, the determination circuitry 243 determines whether or not the motion information obtained by the obtaining circuitry 241 corresponds to the caregiver motion feature information "walking with good posture." If the walking posture has been calculated by the generation circuitry 242, the determination circuitry 243 obtains the posture with which a person contained in the obtained motion information walks from the generation circuitry 242. If the obtained walking posture is smaller than 3°, the determination circuitry 243 then determines that the obtained motion information corresponds to the caregiver motion feature information, that is, the caregiver is walking with good posture. If the walking posture has not been calculated by the generation circuitry 242, the determination circuitry 243 may perform the same processing as that described above with reference to the generation circuitry 242 to calculate the walking posture.

In addition, a case in which the record with the motion ID "23" has been selected from the caregiver motion feature storage circuitry 233 will be described. In this case, as illustrated in FIG. 21, the determination circuitry 243 determines whether or not the motion information obtained by the obtaining circuitry 241 corresponds to the caregiver motion feature information "walking fast." If the walking speed has been calculated by the generation circuitry 242, the determination circuitry 243 obtains the moving speed [m/s] at which a person contained in the obtained motion information walks at predetermined time intervals (0.5 seconds, for example) from the generation circuitry 242. If the maximum moving speed of the obtained moving speed is equal to or higher than 1 [m/s], the determination circuitry 243 then determines that the obtained motion information corresponds to the caregiver motion feature information, that is, the caregiver is walking fast. If the walking speed has not been calculated by the generation circuitry 242, the determination circuitry 243 may perform the same processing as that described above with reference to the generation circuitry 242 to calculate the walking speed.

In addition, a case in which the record with the equipment ID "21" has been selected from the caregiver image feature storage circuitry 235 will be described. In this case, as illustrated in FIG. 23, the determination circuitry 243 carries out pattern matching between color image information obtained by the obtaining circuitry 241 and caregiver equipment feature information "stethoscope." When an image of a stethoscope is extracted from the color image information as a result of pattern matching, the determination circuitry 243 determines whether or not the extracted pixel positions of the stethoscope overlap with coordinates in skeleton information contained in motion information to be evaluated. If the pixel positions of the stethoscope overlap with the coordinates in the skeleton information, the determination circuitry 243 determines that the obtained color image information corresponds to the caregiver equipment feature information, that is, the caregiver holds a stethoscope. As for the other records, the determination circuitry 243 similarly determines whether or not the obtained color image information corresponds to the caregiver equipment feature information.

As described above, the determination circuitry 243 determines whether or not the obtained motion information and color image information corresponds to the selected record. If it is determined that the obtained information corresponds to the selected record, the determination circuitry 243 increments a held caregiver feature number m by 1. The held caregiver feature number m represents the number of features as a caregiver that a person associated with motion information to be evaluated has. As for the other unprocessed records, the determination circuitry 243 similarly determines whether or not the obtained motion information and color image information correspond to the record. When the held caregiver feature number m has reached 5, the determination circuitry 243 determines that the person associated with the motion information to be evaluated to be a caregiver. If the held caregiver feature number m does not reach 5 when the determination circuitry 243 has performed determination on all the records in the caregiver motion feature storage circuitry 233 and the caregiver image feature storage circuitry 235, the determination circuitry 243 determines that the person associated with the motion information to be evaluated is not a caregiver. Although a case in which the threshold for the held caregiver feature number m for determining whether or not a person is a caregiver is 5 has been presented as an example, the embodiment is not limited thereto, and the threshold may be set to any value by the operator. Furthermore, although a case in which the held caregiver feature number m is incremented by 1 when information corresponds to a record has been described, the embodiment is not limited thereto, and each record may be weighted, for example.

As described above, the determination circuitry 243 determines whether or not a person associated with motion information to be evaluated is a subject, or whether or not the person is a caregiver, and outputs the determination result to the storage circuitry 244. If a person associated with motion information to be evaluated is determined not to be a subject nor a caregiver, the determination circuitry 243 outputs a determination result of indeterminable to the storage circuitry 244.

The storage circuitry 244 outputs the determination result of the determination by the determination circuitry 243. For example, the storage circuitry 244 associates the evaluation information generated by the generation circuitry 242 and the determination result of determination by the determination circuitry 243 with each other, and stores the associated information in the evaluation information storage circuitry 236. Note that the storage circuitry 244 is an example of an output control circuitry.

For example, the storage circuitry 244 displays a screen for allowing confirmation of the determination result of determination by the determination circuitry 243 on the output circuitry 110. When the displayed determination result is confirmed, the storage circuitry 244 then associates the determination result and the evaluation information generated by the generation circuitry 242 in association with each other and stores the associated information in the evaluation information storage circuitry 236.

FIG. 25 is a diagram illustrating an example of a display screen displayed by the storage circuitry 244. In the example illustrated in FIG. 25, a case in which a person associated with the motion information to be evaluated is the person 18*a* in FIG. 18A is illustrated. In addition, a case in which evaluation information of "walking with posture of 15°" is output by the generation circuitry 242 and a determination result of being a "subject" is output by the determination circuitry 243 for the person 18*a* will be described.

As illustrated in FIG. 25, the storage circuitry 244 displays a question message "Person 18*a* is determined to be subject. Correct?" and selection buttons of "Yes/No" for responding to the question message on the output circuitry 110. If "Yes" is selected, the storage circuitry 244 then associates the motion information to be evaluated, the determination result "subject," and the evaluation information "walking with posture of 15°" with one another and stores the association result in the evaluation information storage circuitry 236. Alternatively, for example, the storage circuitry 244 may enter the evaluation information "body inclination: 15°" in a free entry field of rehabilitation records as illustrated in FIG. 25.

Figure 26:
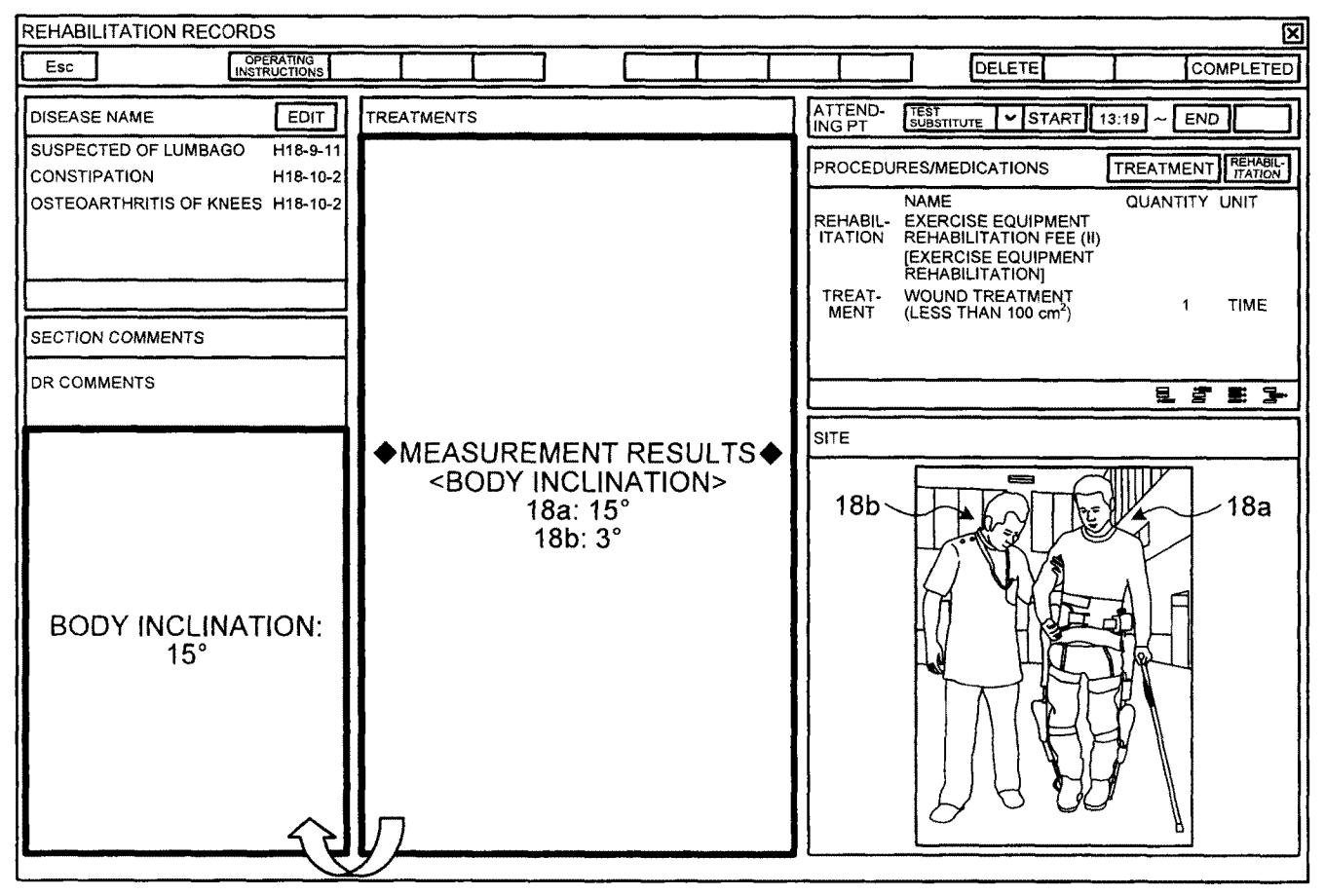

Alternatively, for example, the storage circuitry 244 may store the determination result without confirmation in the evaluation information storage circuitry 236. FIG. 26 is a diagram illustrating an example of a display screen displayed by the storage circuitry 244. Note that FIG. 26 illustrates an example of a display screen displayed under the same condition as that of FIG. 25, and further illustrates a case in which the evaluation information "walking with posture of 3°" for the person 18b is output.

As illustrated in FIG. 26, the storage circuitry 244 displays evaluation information "<body inclination> 18a: 15°, 18b: 3°" for the person 18a and the person 18b. The storage circuitry 244 then associates the motion information to be evaluated, the determination result "subject," and the evaluation information "walking with posture of 15°" with one another and stores the association result in the evaluation information storage circuitry 236. Alternatively, for example, the storage circuitry 244 may display the evaluation information "body inclination: 15°" in a free entry field of rehabilitation records as illustrated in FIG. 26.

In this manner, the storage circuitry 244 outputs the determination result to the evaluation information storage circuitry 236 to store the determination result in the evaluation information storage circuitry 236, and outputs the determination result to the output circuitry 110 to display the determination result on the output circuitry 110. Note that the output of a determination result from the storage circuitry 244 is not limited to the above examples. For example, the storage circuitry 244 may output a determination result to another information processing device or an external storage device.

Figure 27:
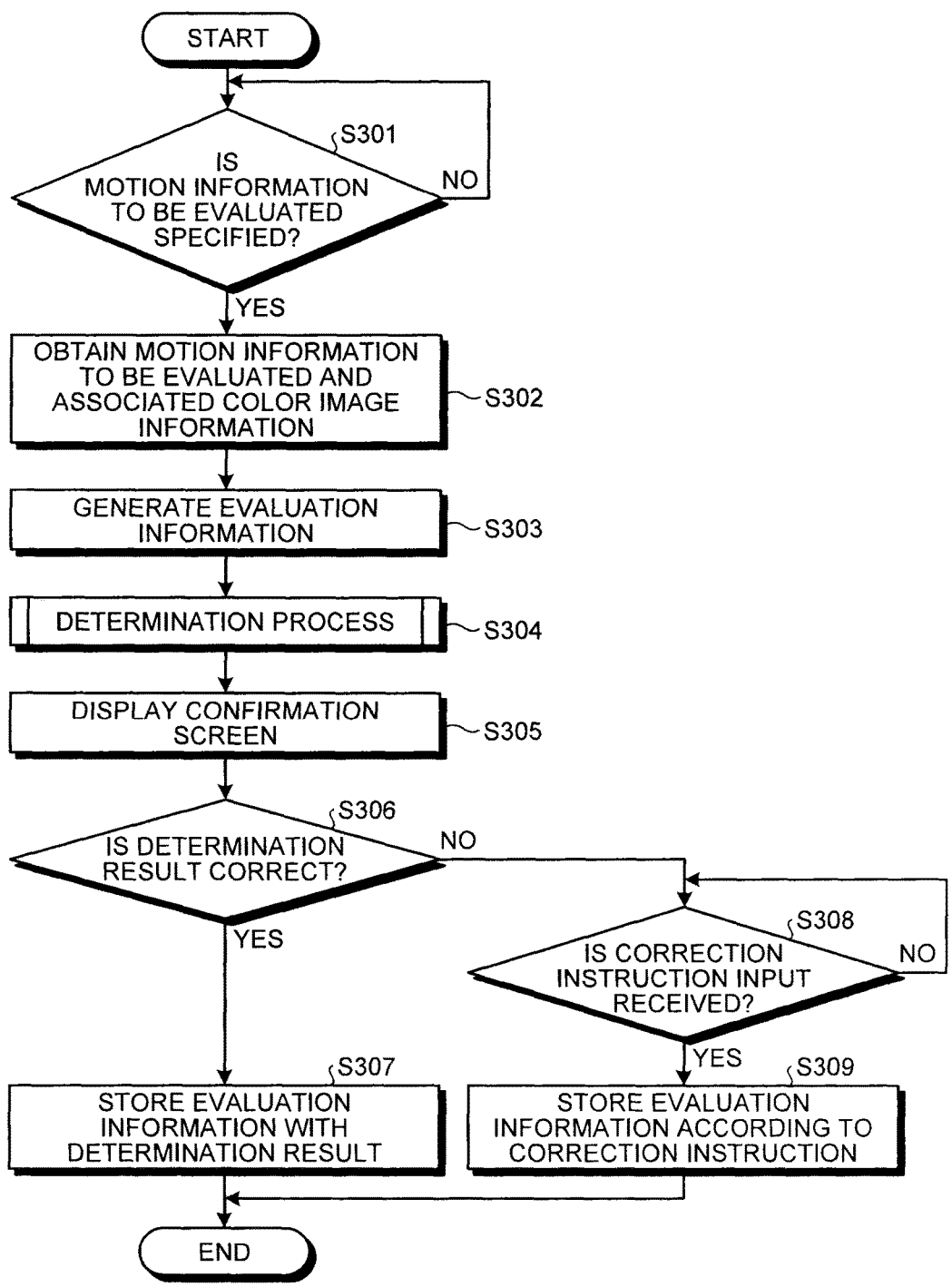
FIG. 27 is a flowchart for explaining an example of procedures of processing performed by a motion information processing device according to the seventh embodiment.

Next, procedures of processing of the motion information processing device 200 according to the seventh embodiment will be described with reference to FIG. 27. FIG. 27 is a flowchart for explaining an example of procedures of processing performed by the motion information processing device 200 according to the seventh embodiment.

As illustrated in FIG. 27, when motion information to be evaluated is specified (Yes in step S301), the obtaining circuitry 241 obtains the motion information to be evaluated, and color image information associated with the motion information (step S302). Note that the obtaining circuitry 241 is in standby state until the motion information to be evaluated is specified (No in step S301).

The generation circuitry 242 generates evaluation information from the motion information obtained by the obtaining circuitry 241 (step S303). For example, the generation circuitry 242 generates the walking posture and the walking speed as evaluation information from the motion information to be evaluated.

The determination circuitry 243 performs a determination process of determining whether or not a person associated with the motion information obtained by the obtaining circuitry 241 is a subject or whether or not the person is a caregiver (step S304).

Figure 28:
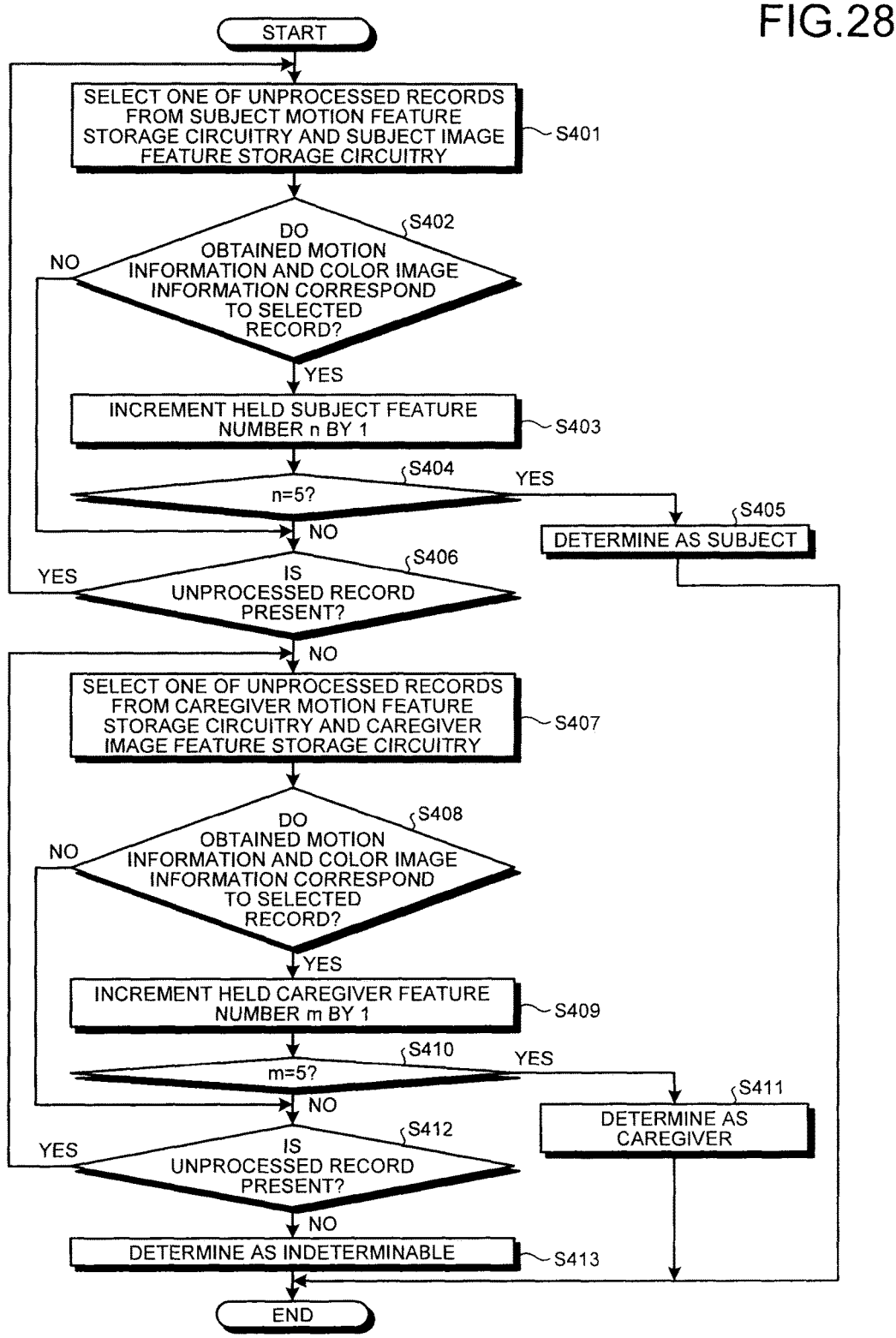
FIG. 28 is a flowchart for explaining an example of procedures of a determination process performed by determination circuitry according to the seventh embodiment.

Here, procedures of processing of the determination circuitry 243 according to the first embodiment will be described with reference to FIG. 28. FIG. 28 is a flowchart for explaining an example of procedures of the determination process performed by the determination circuitry 243 according to the seventh embodiment.

The determination circuitry 243 selects one unprocessed record from the subject motion feature storage circuitry 232 and the subject image feature storage circuitry 234 (step S401). The determination circuitry 243 then determines whether or not the obtained motion information and color image information correspond to the selected record (step S402). If the obtained information corresponds to the selected record (Yes in step S402), the determination circuitry 243 increments the held subject feature number n by 1 (step S403). The determination circuitry 243 then determines whether or not the held subject feature number n has reached 5 (step S404). If the held subject feature number n has reached 5 (Yes in step S404), the determination circuitry 243 determines that the person associated with the motion information obtained by the obtaining circuitry 241 is a subject (step S405).

If the held subject feature number n has not reached 5 (No in step S404), the determination circuitry 243 determines whether or not an unprocessed record is present in the subject motion feature storage circuitry 232 and the subject image feature storage circuitry 234 (step S406). If an unprocessed record is present (Yes in step S406), the determination circuitry 243 proceeds to the processing in step S401.

If no unprocessed record is present (No in step S406), the determination circuitry 243 selects one unprocessed record from the caregiver motion feature storage circuitry 233 and the caregiver image feature storage circuitry 235 (step S407). The determination circuitry 243 then determines whether or not the obtained motion information and color image information correspond to the selected record (step S408). If the obtained information corresponds to the selected record (Yes in step S408), the determination circuitry 243 increments the held caregiver feature number m by 1 (step S409). The determination circuitry 243 then determines whether or not the held caregiver feature number m has reached 5 (step S410). If the held caregiver feature number m has reached 5 (Yes in step S410), the determination circuitry 243 determines that the person associated with the motion information obtained by the obtaining circuitry 241 is a caregiver (step S411).

If the held caregiver feature number m has not reached 5 (No in step S410), the determination circuitry 243 determines whether or not an unprocessed record is present in the caregiver motion feature storage circuitry 233 and the caregiver image feature storage circuitry 235 (step S412). If an unprocessed record is present (Yes in step S412), the determination circuitry 243 proceeds to the processing in step S407.

If no unprocessed record is present (No in step S412), the determination circuitry 243 determines that the person associated with the motion information obtained by the obtaining circuitry 241 is indeterminable (step S413).

The description refers back to FIG. 27. After the determination process is performed by the determination circuitry 243, the storage circuitry 244 displays a confirmation screen for confirmation whether or not the determination result is correct or false on the output circuitry 110 (step S305). If the input circuitry 120 has received an input indicating that the determination result is correct (Yes in step S306), the storage circuitry 244 then stores evaluation information generated by the generation circuitry 242 together with the determination result in the evaluation information storage circuitry 236 (step S307).

If the input circuitry 120 has received an input indicating that the determination result is incorrect (No in step S306), the storage circuitry 244 waits until a correction instruction input is received by the input circuitry 120 (No in step S308). If the input circuitry 120 has received a correction instruction input (Yes in step S308), the storage circuitry 244 then stores evaluation information in the evaluation information storage circuitry 236 according to the correction instruction input (step S309), and terminates the processing.

Note that the procedures of processing described above need not necessarily be performed in the order described above. For example, the processing of step S303 that is a process of generating evaluation information and the processing of step S304 of performing the determination process are not limited to the order described above, and the processing of step S303 may be performed after the processing of step S304 is performed.

Furthermore, for example, the processing from step S401 to step S406 that is a process of determining whether or not a person is a subject and the processing from step S407 to step S412 that is a process of determining whether or not a person is a caregiver are not limited to the order described above. Specifically, the processing from step S401 to step S406 may be performed after the processing from step S407 to step S412 is performed.

As described above, the motion information processing device 200 according to the seventh embodiment stores subject motion feature information indicating a feature of a motion of a subject of rehabilitation. The motion information processing device 200 then obtains motion information indicating a motion of a person. The motion information processing device 200 then determines whether or not the person associated with the obtained motion information is a subject by using the subject motion feature information. Thus, the motion information processing device 200 according to the seventh embodiment can determine whether or not a digitally recorded motion of a person is that of a subject of rehabilitation.

Figure 29:
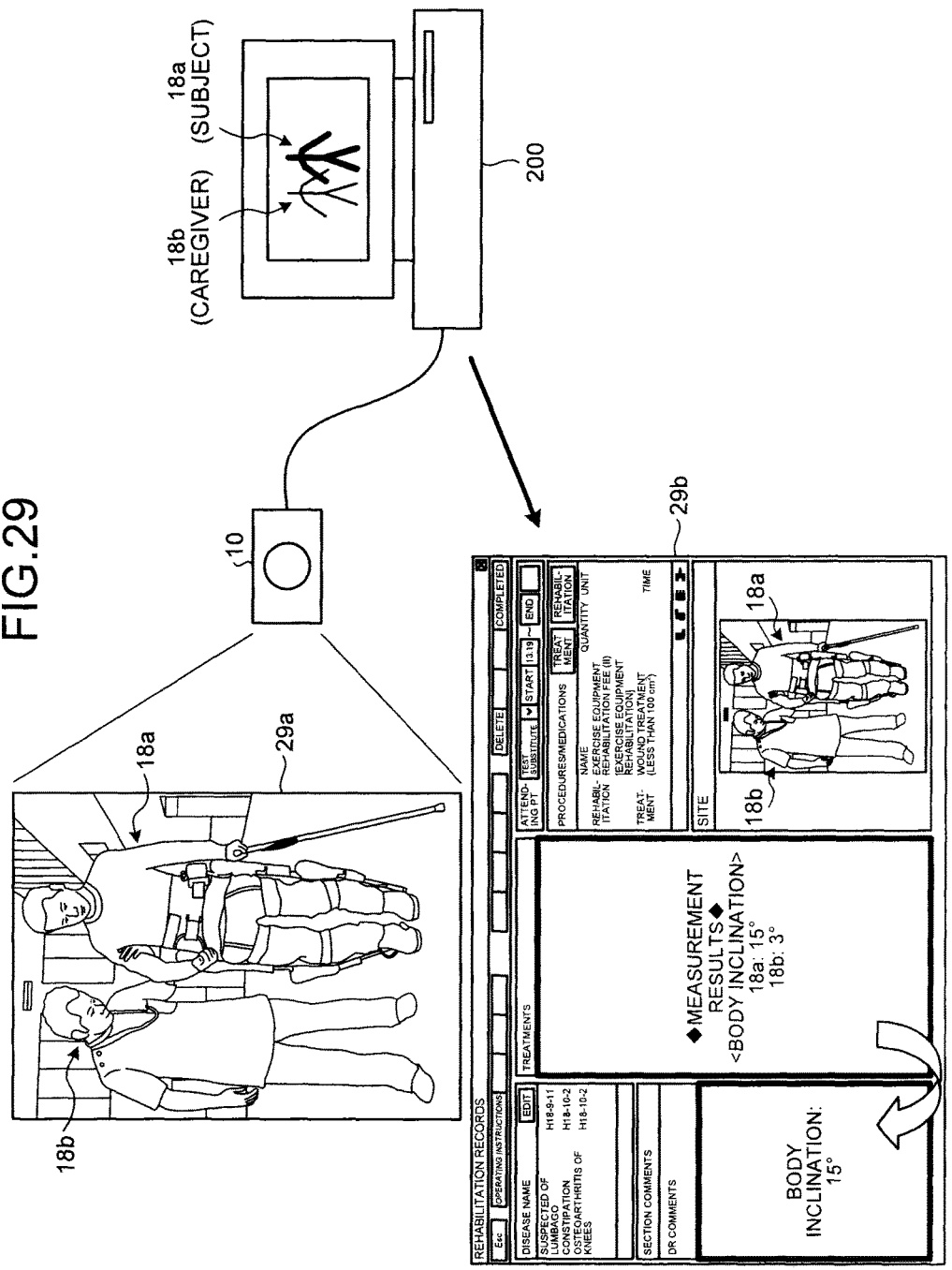
FIG. 29 is a diagram for explaining effects of the motion information processing device according to the seventh embodiment.

FIG. 29 is a diagram for explaining effects of the motion information processing device 200 according to the seventh embodiment. As illustrated in FIG. 29, for example, the motion information processing device 200 obtains motion information of each of the person 18a and the person 18b carrying out rehabilitation on the basis of a distance image 29a photographed by the motion information collector 10. The motion information processing device 200 then determines whether or not the person associated with the obtained motion information is a subject or whether or not the person is a caregiver by using the motion information. The motion information processing device 200 then displays the determination result on a display screen 29b and stores the determination result and evaluation information based on the motion information in the evaluation information storage circuitry 236. Thus, the motion information processing device 200 can evaluate the motion information of a subject, for example.

Furthermore, the motion information processing device 200 stores caregiver motion feature information indicating a feature of a motion of a caregiver assisting a subject, for example. The motion information processing device 200 then determines whether or not the person associated with the obtained motion information is a caregiver by using the caregiver motion feature information. Thus, the motion information processing device 200 according to the seventh embodiment can determine whether or not a digitally recorded motion of a person is that of a caregiver.

Furthermore, for example, the motion information processing device 200 displays a screen for confirmation of a determination result on a predetermined display, and when the determination result is confirmed, stores the determination result and the generated evaluation information in association with each other in predetermined storage circuitry. Thus, the motion information processing device 200 can prevent a person to be evaluated from being falsely evaluated, for example.

Furthermore, for example, the motion information processing device 200 stores subject image feature information indicating a feature of an image of a subject. The motion information processing device 200 then obtains a person image in which the person is photographed. The motion information processing device 200 then determines whether or not the person associated with the obtained person image is a subject by using the subject image feature information. It is therefore possible to determine whether or not a digitally recorded motion of a person is that of a subject.

Furthermore, for example, the motion information processing device 200 stores caregiver image feature information indicating a feature of an image of a caregiver. The motion information processing device 200 then obtains a person image in which the person is photographed. The motion information processing device 200 then determines whether or not the person associated with the obtained person image is a caregiver by using the caregiver image feature information. It is therefore possible to determine whether or not a digitally recorded motion of a person is that of a caregiver.

Eighth Embodiment

Although a case in which whether or not a person is a subject is determined by using a feature of a motion and a feature of an image of a subject has been described in the seventh embodiment described above, the embodiment is not limited thereto. For example, the motion information processing device 200 may determine whether or not a person is a subject by using personal information of the subject. Thus, in the eighth embodiment, a case in which the motion information processing device 200 determines whether or not a person is a subject by using personal information of the subject will be described.

Figure 30:
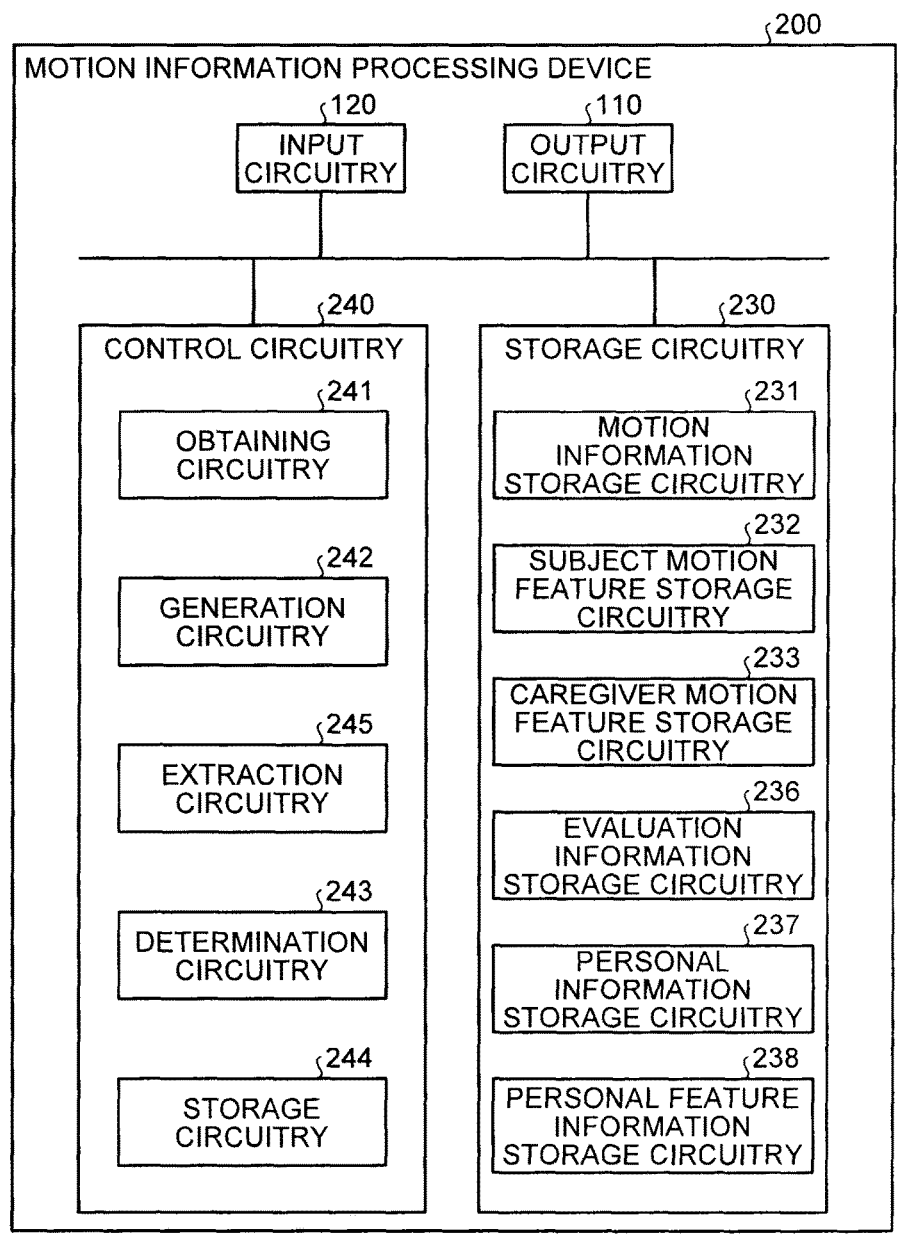
FIG. 30 is a block diagram illustrating an example configuration of a motion information processing device according to an eight embodiment.

FIG. 30 is a block diagram illustrating an example configuration of the motion information processing device 200 according to the eighth embodiment. As illustrated in FIG. 30, the motion information processing device 200 according to the eighth embodiment has a configuration similar to that of the motion information processing device 200 illustrated in FIG. 19, and differs therefrom in that the storage circuitry 230 further includes a personal information storage circuitry 237 and a personal feature information storage circuitry 238 and in that the control circuitry 240 further includes extraction circuitry 245. In the eighth embodiment, the description will be focused mainly on the differences from the seventh embodiment, and components having the same functions as those described in the seventh embodiment will be designated by the same reference numerals as those in FIG. 19 and the description thereof will not be repeated. Note that, in the motion information processing device 200 according to the eighth embodiment, the storage circuitry 230 may not include the subject image feature storage circuitry 234 and the caregiver image feature storage circuitry 235.

The personal information storage circuitry 237 stores identification information identifying a subject and personal information in association with each other. In the information, a subject ID is information for identifying a subject, such as a patient number or the like for identifying a patient in a medical institution, for example. The personal information is information peculiar to the corresponding subject, and contains information such as height, chest circumference, and abdominal circumference, for example. Note that the information stored in the personal information storage circuitry 237 is information obtained from a medical information system, a personal health record (PHR), or the like, for example, and a disease name, history of hospital visits, and the like in addition to physical features of a subject may be stored.

The personal feature information storage circuitry 238 stores a personal feature ID and personal feature information. The personal feature ID is information for identifying a feature that can be used to identify a person, and a number is allotted each time a record in the personal feature information storage circuitry 238 is registered by the designer of the motion information processing device 200. The personal feature information refers to an item of personal information that can be used for determining whether or not a person is a subject by using the personal information, and is defined in advance by the designer of the motion information processing device 200, for example. Note that the information stored in the personal feature information storage circuitry 238 is may be obtained from a medical information system, a personal health record (PHR), or the like, for example.

FIG. 31 is a table illustrating an example of information stored in the personal feature information storage circuitry 238. In the first record of FIG. 31, a personal feature ID "001" and personal feature information "( ) cm in height" are stored. Specifically, the personal feature information storage circuitry 238 stores "( ) cm in height," which is an item of personal information that can be used for determining whether or not a person is a subject by using the personal information, as personal feature information with the personal feature ID "001." The personal feature information "( ) cm in height" is used for determination after information on the height of the subject is obtained from the personal information storage circuitry 237. In the second record of FIG. 31, a personal feature ID "002" and personal feature information "( ) cm in chest circumference" are stored. Specifically, the personal feature information storage circuitry 238 stores "( ) cm in chest circumference," which is an item of personal information that can be used for determining whether or not a person is a subject by using the personal information, as personal feature information with the personal feature TD "002." In the third record of FIG. 31, a personal feature TD "003" and personal feature information "( ) cm in abdominal circumference" are stored. Specifically, the personal feature information storage circuitry 238 stores "( ) cm in abdominal circumference," which is an item of personal information that can be used for determining whether or not a person is a subject by using the personal information, as personal feature information with the personal feature ID "003." As for the other records, the personal feature information storage circuitry 238 stores an item of personal information that can be used for determining whether or not a person is a subject by using the personal information.

The extraction circuitry 245 receives identification information identifying a subject, and extracts personal information associated with the received identification information from the personal information storage circuitry 237. In one example, the extraction circuitry 245 extracts a physical feature of a subject from information recorded in an electronic medical record of the subject.

For example, when the input circuitry 120 receives an input of a subject ID of a subject carrying out rehabilitation when the rehabilitation is started, the extraction circuitry 245 receives the subject ID from the input circuitry 120.

Subsequently, the extraction circuitry 245 extracts personal information associated with the personal feature information in each record in the personal feature information storage circuitry 238 from the personal information storage circuitry 237 by using the received subject ID. In the example illustrated in FIG. 31, "( ) cm in height" is stored as the personal feature information in the first record. In this case, the extraction circuitry 245 refers to the personal information storage circuitry 237 and extracts "170 cm in height," for example, as the personal information associated with the received subject ID. The height extracted here is used by the determination circuitry 243 for determining whether or not a person is a subject by using the first record "( ) cm in height" in the personal feature information storage circuitry 238. As for the other records in the personal feature information storage circuitry 238, the extraction circuitry 245 similarly extracts personal information associated with each record in the personal feature information storage circuitry 238 from the personal information storage circuitry 237 by using the received subject ID.

Figure 32:
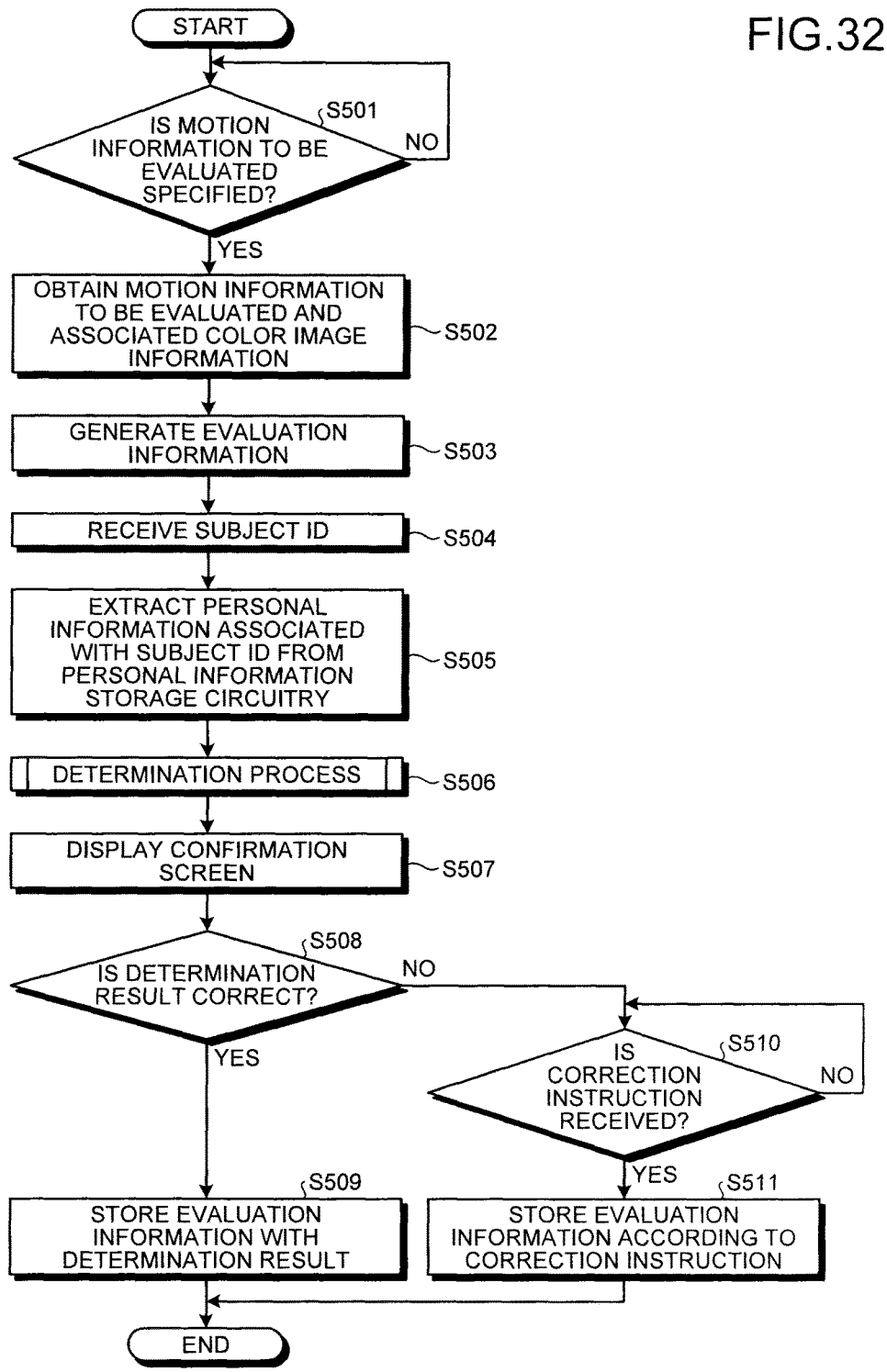
FIG. 32 is a flowchart for explaining an example of procedures of processing performed by the motion information processing device according to the eighth embodiment.

Next, procedures of processing of the motion information processing device 200 according to the eighth embodiment will be described with reference to FIG. 32. FIG. 32 is a flowchart for explaining an example of procedures of processing performed by the motion information processing device 200 according to the eighth embodiment. Note that the input circuitry 120 receives an input of a subject ID of a subject carrying out rehabilitation when the rehabilitation is started.

As illustrated in FIG. 32, in the motion information processing device 200 according to the eighth embodiment, since the processing from step S501 to step S503 is the same as the processing from step S301 to step S303, respectively, illustrated in FIG. 27, the description thereof will not be repeated.

After the processing in step S503 is terminated, the extraction circuitry 245 receives the subject ID of a subject carrying out rehabilitation from the input circuitry 120 (step S504). The extraction circuitry 245 then extracts personal information associated with the received subject TD from the personal information storage circuitry 237 (step S505).

The determination circuitry 243 performs a determination process of determining whether or not a person associated with motion information obtained by the obtaining circuitry 241 is a subject, or whether or not the person is a caregiver (step S506). Note that the determination circuitry 243 basically performs the determination process in the procedures of processing as illustrated in FIG. 28, but the determination process is different in that the personal feature information storage circuitry 238 is used for determination. The difference will thus be described below with reference to FIG. 28.

In step S401, the determination circuitry 243 selects one unprocessed record from the subject motion feature storage circuitry 232 and the personal feature information storage circuitry 238. Note that, when the motion information processing device 200 according to the eighth embodiment includes the subject image feature storage circuitry 234, the unprocessed record may be selected from the subject image feature storage circuitry 234.

Subsequently, in step S402, the determination circuitry 243 determines whether or not the obtained motion information and color image information correspond to the selected record. In this process, when the record is selected from the personal feature information storage circuitry 238, the determination circuitry 243 performs determination by using the personal information extracted by the extraction circuitry 245. For example, when the first record in FIG. 31 is selected, the determination circuitry 243 obtains the personal feature information "( ) cm in height" from the personal feature information storage circuitry 238.

Subsequently, the determination circuitry 243 obtains the personal information "170 cm in height" extracted by the extraction circuitry 245 as personal information associated with the personal feature information "( ) cm in height." The determination circuitry 243 then combines the obtained personal feature information "( ) cm in height" and the personal information "170 cm in height" to generate a condition "170 cm in height." The determination circuitry 243 then determines whether or not the motion information and color image information obtained by the obtaining circuitry 241 satisfy the generated condition "170 cm in height." Specifically, the determination circuitry 243 obtains the height from skeleton information contained in the motion information and determines whether or not the value is close to 170 cm.

The determination circuitry 243 then performs the processing in step S403 and subsequent steps. Since the processing in step S403 and subsequent steps is the same as that described in the seventh embodiment, the description thereof will not be repeated.

The description refers back to FIG. 32, in which the motion information processing device 200 performs processing in step S507 and subsequent steps. Since the processing from step S507 to step S511 in FIG. 32 is the same as that from step S305 to step S309 in FIG. 27, respectively, the description thereof will not be repeated.

Note that the procedures of processing described above need not necessarily be performed in the order described above. For example, the processing in step S503 that is a process of generating evaluation information may be performed after the processing in step S505 of extracting personal information is performed.

As described above, the motion information processing device 200 according to the eighth embodiment includes the personal information storage circuitry 237 that stores identification information for identifying a subject and personal information of the subject in association with each other. The motion information processing device 200 receives identification information, and extracts personal information associated with the received identification information from the personal information storage circuitry 237. The motion information processing device 200 then refers to the personal information extracted by the extraction circuitry 245, and determines whether or not a person associated with a person image is the person associated with the personal information. Thus, the motion information processing device 200 can correctly determine whether or not a digitally recorded motion of a person is that of a subject of rehabilitation.

Although a case in which the motion information processing device 200 stores the personal information storage circuitry 237 and the personal feature information storage circuitry 238 has been described in the eighth embodiment, the motion information processing device 200 need not necessarily store the personal information storage circuitry 237 and the personal feature information storage circuitry 238. For example, in a case where the motion information processing device 200 is connected to the medical information system described above via a network, the extraction circuitry 245 may extract personal information associated with personal feature information in each record in the personal feature information storage circuitry 238 from the medical information system.

Ninth Embodiment

Although a case in which the determination process is performed by using information capable of identifying a subject has been described in the eighth embodiment described above, the embodiment is not limited thereto. In the ninth embodiment, a case in which a determination process is performed by using information capable of identifying a caregiver will be described, for example.

Figure 33:
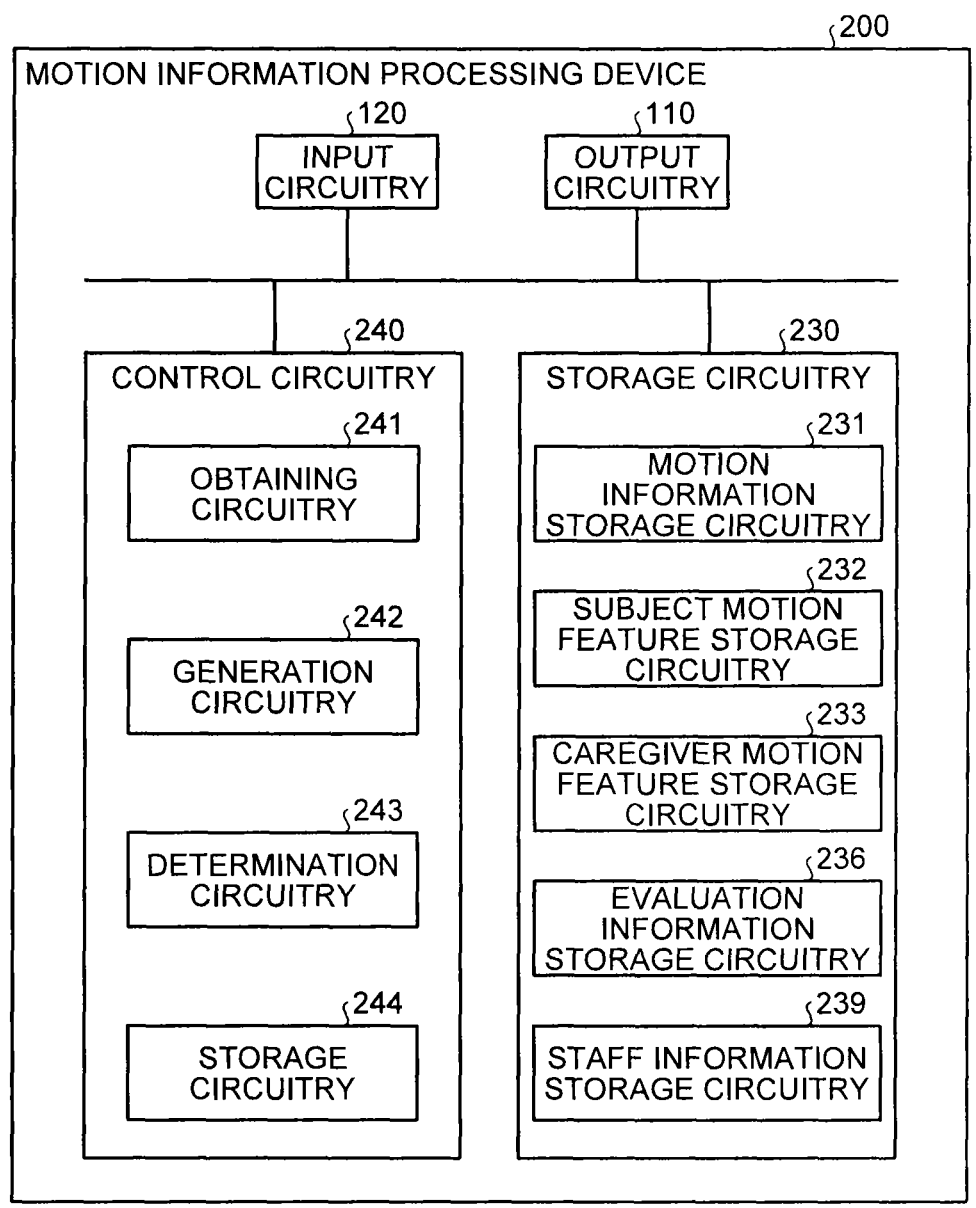
FIG. 33 is a block diagram illustrating an example configuration of a motion information processing device according to a ninth embodiment.

FIG. 33 is a block diagram illustrating an example configuration of a motion information processing device 200 according to the ninth embodiment. As illustrated in FIG. 33, the motion information processing device 200 according to the ninth embodiment has a configuration similar to that of the motion information processing device 200 illustrated in FIG. 19, and differs therefrom in that the storage circuitry 230 further includes a staff information storage circuitry 239. In the ninth embodiment, the description will be focused mainly on the differences from the seventh embodiment, and components having the same functions as those described in the seventh embodiment will be designated by the same reference numerals as those in FIG. 19 and the description thereof will not be repeated. Note that, in the motion information processing device 200 according to the ninth embodiment, the storage circuitry 230 may not include the subject image feature storage circuitry 234 and the caregiver image feature storage circuitry 235.

The staff information storage circuitry 239 stores a staff ID and a name in association with each other. The staff ID is information for identifying a staff, such as a number for identifying a person working in a medical institution, for example. The name is information indicating the name of a person corresponding to the staff ID. The information stored in the staff information storage circuitry 239 is information obtained from a staff personnel system for managing personnel of staffs in a medical institution in which the motion information processing device 200 is used, for example. Note that the staff includes a caregiver.

Figures 34, 35:
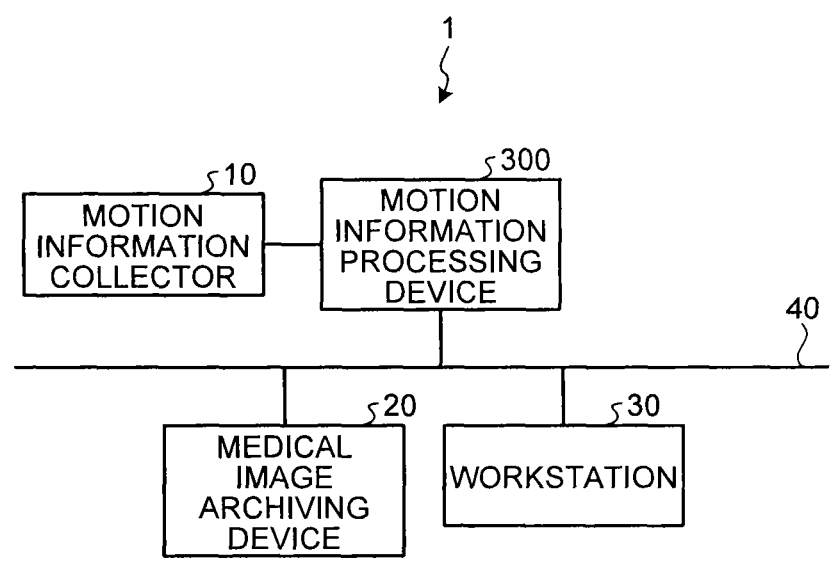
FIG. 34 is a table illustrating an example of information stored in staff information storage circuitry.
FIG. 35 is a block diagram illustrating an example configuration of a motion information processing system according to an eleventh embodiment.

FIG. 34 is a table illustrating an example of information stored in the staff information storage circuitry 239. In the first record of FIG. 34, a staff ID "1" and a name "AB" are stored. Specifically, the staff information storage circuitry 239 stores that the name of a staff represented by the staff ID "1" is "AB." In the second record of FIG. 34, a staff ID "2" and a name "CD" are stored. Specifically, the staff information storage circuitry 239 stores that the name of a staff represented by the staff ID "2" is "CD." In the third record of FIG. 34, a staff ID "3" and a name "EF" are stored. Specifically, the staff information storage circuitry 239 stores that the name of a staff represented by the staff ID "3" is "EF." As for staffs with other staff IDs, the staff information storage circuitry 239 similarly stores a staff ID and a name in association with each other.

Next, procedures of processing of the motion information processing device 200 according to the ninth embodiment will be described. The procedures of processing of the motion information processing device 200 according to the ninth embodiment are similar to those of the motion information processing device 200 according to the seventh embodiment described with reference to FIG. 27, but differs therefrom in that the staff information storage circuitry 239 is used for determination. The difference will thus be described below with reference to FIG. 28.

Since the processing from step S401 to step S405 is the same as that described with reference to FIG. 28, the description thereof will not be repeated.

In step S407, the determination circuitry 243 selects one unprocessed record from the caregiver motion feature storage circuitry 233 and the staff information storage circuitry 239. Note that, when the motion information processing device 200 according to the ninth embodiment includes the caregiver image feature storage circuitry 235, the unprocessed record may be selected from the caregiver image feature storage circuitry 235.

Subsequently, in step S408, the determination circuitry 243 determines whether or not the obtained motion information and color image information correspond to the selected record. In this process, when the record is selected from the staff information storage circuitry 239, the determination circuitry 243 performs pattern matching on a nameplate from the color image information obtained by the obtaining circuitry 241. When an image of the nameplate is extracted from the color image information through pattern matching, the determination circuitry 243 recognizes characters on the extracted nameplate by a known character recognition technology. When the characters, such as "AB," are recognized through character recognition, the determination circuitry 243 then determines whether or not the characters are stored in the staff information storage circuitry 239. If the characters recognized through character recognition are stored in the staff information storage circuitry 239, the determination circuitry 243 determines that the obtained color image information corresponds to the personnel information.

The determination circuitry 243 then performs the processing in step S409 and subsequent steps. Since the processing in step S409 and subsequent steps is the same as that described in the seventh embodiment, the description thereof will not be repeated.

As described above, the motion information processing device 200 according to the ninth embodiment includes an identification information storage circuitry that stores identification information for identifying a caregiver. In addition, the motion information processing device 200 then obtains a person image in which the person is photographed. The motion information processing device 200 then extracts identification information from the obtained person image, and determines whether or not the extracted identification information corresponds to a person associated with the identification information stored in the identification information storage circuitry. Thus, the motion information processing device 200 can identify the individual name of a caregiver.

Although a case in which the motion information processing device 200 determines whether or not a person is a caregiver by using the name of a staff has been described in the ninth embodiment, the embodiment is not limited thereto, and whether or not a person is a caregiver may be determined through face recognition of a staff. In this case, the staff information storage circuitry 239 stores a staff ID and a face image of the staff in association with each other. The determination circuitry 243 then recognizes an image of a face from color image information obtained by the obtaining circuitry 241, and performs matching on the recognized face image and the face image stored in the staff information storage circuitry 239 to determine whether or not the obtained color image information corresponds to staff information.

Furthermore, although a case in which the motion information processing device 200 stores the staff information storage circuitry 239 has been described in the ninth embodiment, the motion information processing device 200 need not necessarily store the staff information storage circuitry 239. For example, in a case where the motion information processing device 200 is connected to the staff personnel system described above via a network, the determination circuitry 243 may access the staff personnel system and perform determination by using information corresponding to that stored in the staff information storage circuitry 239.

Tenth Embodiment

While the seventh to ninth embodiments have been described above, various different embodiments other than the seventh to ninth embodiments can be employed.

For example, the configurations described in the seventh to ninth embodiments above are only examples, and all the configurations are not necessarily required. For example, the motion information processing device 200 may not have the generation circuitry 242. Specifically, in the motion information processing device 200, the obtaining circuitry 241 obtains motion information indicating a motion of a person. The determination circuitry 243 then determines whether or not a person associated with the obtained motion information is a subject by using the subject motion feature information. The storage circuitry 244 then outputs the determination result of the determination by the determination circuitry 243. Thus, the motion information processing device 200 can determine whether or not a digitally recorded motion of a person is that of a subject of rehabilitation. For example, the motion information processing device 200 may output the obtained motion information and the determination result in association with each other to another device. Furthermore, for example, in the motion information processing device 200, the storage circuitry 230 may have any of the subject motion feature storage circuitry 232, the caregiver motion feature storage circuitry 233, the subject image feature storage circuitry 234, and the caregiver image feature storage circuitry 235.

Furthermore, for example, the configurations described in the seventh to ninth embodiments above are exemplary only, and any one of multiple devices included in a medical information processing system may have the configurations described above. Specifically, a medical information processing system includes obtaining circuitry 241, generation circuitry 242, determination circuitry 243, and storage circuitry 244. The obtaining circuitry 241 obtains motion information indicating a motion of a person. The generation circuitry 242 generates the evaluation information of rehabilitation from the motion information obtained by the obtaining circuitry 241. The determination circuitry 243 then determines whether or not a person associated with the obtained motion information is a subject by using the subject motion feature information. The storage circuitry 244 then outputs the evaluation information on the basis of the determination result from the determination circuitry.

Furthermore, for example, although a case in which determination is performed by using a feature of a motion of a person has been described in the seventh to ninth embodiments above, the embodiment is not limited thereto.

In one example, the motion information processing device 200 may perform determination by using a speech recognition result. Specifically, as a result of concentrating on rehab, a subject tends to talk less or moan. In contrast, for caring for and encouraging a subject, a caregiver tends to utter words such as "are you all right?," "Right foot next," "Slowly," and the like. Thus, the motion information processing device 200 can determine a subject and a caregiver by using these features.

Here, a case in which determination on whether or not a person is a subject is performed by using the feature that a subject tends to talk less will be described. In this case, the subject motion feature storage circuitry 232 stores information in which a predetermined motion ID and subject motion feature information "not talking for three minutes or longer"

are associated with each other. The obtaining circuitry 241 then obtains motion information and a speech recognition result associated with each frame of the moLlon information. If a speech recognition result indicating not talking continues for three minutes for the motion information obtained by the obtaining circuitry 241, the determination circuitry 243 then determines that the motion information corresponds to subject motion feature information with the predetermined motion ID, that is, the person is not talking for three minutes or longer. In this manner, the motion information processing device 200 can determine a subject with high accuracy by using a speech recognition result.

Furthermore, a case in which determination on whether or not a person is a caregiver is performed by using an utterance "Are you all right?" of a caregiver will be described. In this case, the caregiver motion feature storage circuitry 233 stores information in which a predetermined motion ID and caregiver motion feature information "uttering words 'Are you all right?'" are associated with each other. The obtaining circuitry 241 then obtains motion information and a speech recognition result associated with each frame of the motion information. If a speech recognition result indicating the utterance of words "Are you all right?" is provided for the motion information obtained by the obtaining circuitry 241, the determination circuitry 243 then determines that the motion information corresponds to caregiver motion feature information with the predetermined motion ID, that is, the person has uttered the words "Are you all right?" In this manner, the motion information processing device 200 can determine a caregiver with high accuracy by using a speech recognition result.

In another example, the motion information processing device 200 may perform determination by using a thermal sensor (thermograph, etc.). Specifically, a subject puts his/her efforts to moves his/her body, and thus the body temperature of the subject rises during rehab. Thus, the motion information processing device 200 can determine a subject by using this feature. In this case, the motion information processing device 200 includes a thermal sensor as the input circuitry 120, and obtains the body temperature of a person associated with the motion information obtained by the obtaining circuitry 241 for each frame.

In one aspect, the subject motion feature storage circuitry 232 stores information in which a predetermined motion ID and subject motion feature information "body temperature being 36.5 degrees or higher" are associated. The obtaining circuitry 241 then obtains the motion information and the body temperature associated with each frame of the motion information. If the body temperature is 36.5 degrees or higher for the motion information obtained by the obtaining circuitry 241, the determination circuitry 243 then determines that the motion information corresponds to subject motion feature information with the predetermined ID. In this manner, the motion information processing device 200 can determine a subject with high accuracy by using a thermal sensor.

As described above, according to the seventh to tenth embodiments, the motion information processing device 200 can determine whether or not a digitally recorded motion of a person is that of a subject of rehabilitation.

Eleventh Embodiment

As described above, in the seventh to tenth embodiments, a case of enabling determination on whether or not a digitally recorded motion of a person is that of a subject of rehabilitation to support rehabilitation has been described. Thus, in eleventh and twelfth embodiments, a case of providing a motion information processing device 300 capable of providing information with which a motion can be confirmed while hiding personal information of a test subject (subject) will be described. Note that, in the eleventh and twelfth embodiments, the test subject includes a person carrying out a predetermined motion and a person who is a subject of rehabilitation.

FIG. 35 is a block diagram illustrating an example configuration of a medical information processing system 1 according to the eleventh embodiment. The medical information processing system 1 according to the eleventh embodiment is a system for supporting rehabilitation carried out in a medical institution, at home, in an office, or the like. Although a case in which the motion information processing device 300 is applied to the medical information processing system 1 will be described in the eleventh embodiment, the embodiment is not limited thereto. For example, the motion information processing device 300 can also provide information with which a motion can be confirmed while hiding personal information of a test subject without being applied to the medical information processing system 1.

As illustrated in FIG. 35, the medical information processing system 1 according to the eleventh embodiment includes a motion information collector 10, the motion information processing device 300, a medical image archiving device 20, and a workstation 30. Note that the motion information processing device 300, the medical image archiving device 20, and the workstation 30 are in state in which the devices can mutually communicate directly or indirectly via a local area network (LAN) 40 installed in a hospital, for example. For example, in a case where a picture archiving and communication system (PACS) is introduced in the medical information processing system 1, for example, the devices transmit and receive medical image information and the like according to the DICOM (Digital Imaging and Communications in Medicine) standard.

The medical image archiving device 20 archives various information data for supporting rehabilitation. For example, the medical image archiving device 20 includes a database that archives image information, stores various information data transmitted by the motion information processing device 300 into the database, and holds the information data. In one example, in a case where an electronic medical record (EMR) is applied to the medical information processing system 1, the medical image archiving device 20 stores information stored on the EMR. The information stored in the medical image archiving device 20 can be browsed by those authorized to access the medical information processing system 1 or having a predetermined authority such as an attending doctor or a hospital director, for example. Information stored in the medical image archiving device 20 will be described later.

Although a case in which the medical image archiving device 20 archives information in the medical information processing system 1 in a certain medical institution will be described in the eleventh embodiment, the embodiment is not limited thereto. For example, the medical image archiving device 20 may be provided on the Internet. In this case, the medical image archiving device 20 may archive information of multiple medical institutions connected to the Internet for each of the medical institutions, or may archive information of each medical institution in such a manner that the information can be mutually browsed. Furthermore, the medical image archiving device 20 may archive information data with an access authority set to each of the information data stored in the medical image archiving device 20.

The workstation 30 displays various information data for supporting rehabilitation. For example, the workstation 30 obtains motion information from the medical image archiving device 20, and displays the obtained information.

The motion information processing device 300 performs various processes for supporting rehabilitation by using motion information output from the motion information collector 10. The motion information processing device 300 is an information processing device such as a computer or a workstation, for example.

In the medical information processing system 1, it is considered useful in medical practice to archive motion information in rehab collected by the motion information collector 10 as information that can be browsed by doctors and physical therapist other than an attending doctor in the medical image archiving device 20, for example. For example, a doctor can show information (a moving image or skeleton information) with which a motion in rehab of a test subject can be checked as a good example to another test subject carrying out similar rehab by using the information stored in the medical image archiving device 20. This behavior, however, discloses personal information of the test subject presented as a good example to another test subject, which is undesirable in terms of protection of personal information.

Thus, the motion information processing device 300 according to the eleventh embodiment can provide information with which a motion can be confirmed while hiding personal information of a test subject by performing processing as will be described below.

Figure 36:
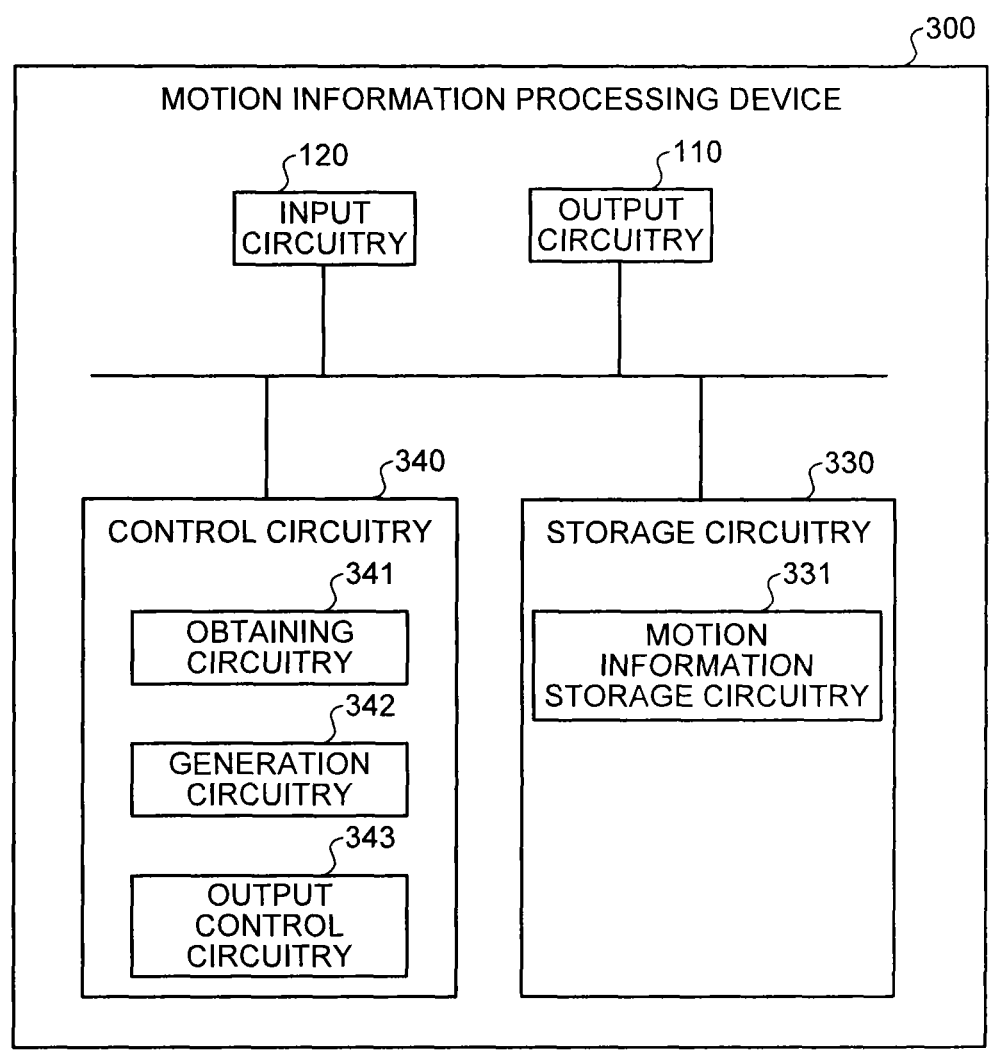
FIG. 36 is a block diagram illustrating a detailed example configuration of a motion information processing device according to the eleventh embodiment.

FIG. 36 is a block diagram illustrating a detailed example configuration of the motion information processing device 300 according to the eleventh embodiment. As illustrated in FIG. 36, in the motion information processing device 300, storage circuitry 330 includes motion information storage circuitry 331.

The motion information storage circuitry 331 stores various information data collected by the motion information collector 10. Specifically, the motion information storage circuitry 331 stores motion information generated by the motion information generation circuitry 14. More specifically, the motion information storage circuitry 331 stores skeleton information of each frame generated by the motion information generation circuitry 14. Note that the motion information storage circuitry 331 can also associate color image information, depth image information, and a speech recognition result output by the motion information generation circuitry 14 for each frame and store the association result. Note that the color image information is an example of photographed image information.

The motion information storage circuitry 331 according to the eleventh embodiment stores information similar to that stored in the motion information storage circuitry 131 illustrated in FIG. 7, for example.

The description refers back to FIG. 36. As illustrated in FIG. 36, in the motion information processing device 300, control circuitry 340 includes obtaining circuitry 341, generation circuitry 342, and output control circuitry 343.

The obtaining circuitry 341 obtains motion information of a test subject. For example, the obtaining circuitry 341 obtains motion information at least containing skeleton information and color image information in time series. In one example, each time the motion information collector 10 and the motion information processing device 300 are powered on and skeleton information of one frame is stored in the motion information storage circuitry 331, the obtaining circuitry 341 obtains the stored skeleton information and color image information of a frame corresponding to the stored skeleton information from the motion information storage circuitry 331. Note that the motion information obtained by the obtaining circuitry 341 is an example of first motion information.

Although a case in which, each time skeleton information and color image information of each frame are stored in the motion information storage circuitry 331 by the motion information collector 10, the obtaining circuitry 341 obtains various information data in real time will be described in the eleventh embodiment, the embodiment is not limited thereto. For example, the obtaining circuitry 341 may obtain a group of frames of skeleton information and color image information stored in the motion information storage circuitry 331.

The generation circuitry 342 generates image information, with which the skeleton of a test subject can be visually confirmed, as medical image information by using the positions of joints contained in the skeleton information, for example.

Figure 37A:
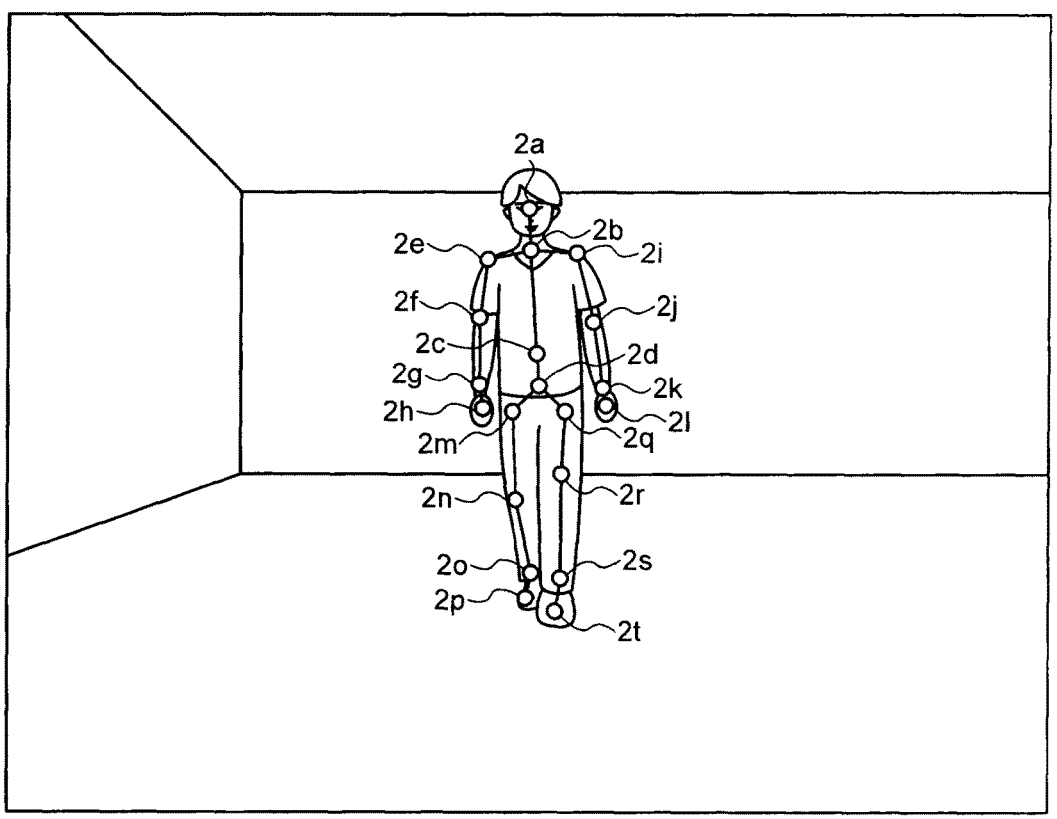
FIG. 37A is a diagram for explaining processing performed by generation circuitry according to the eleventh embodiment.
Figure 37B:
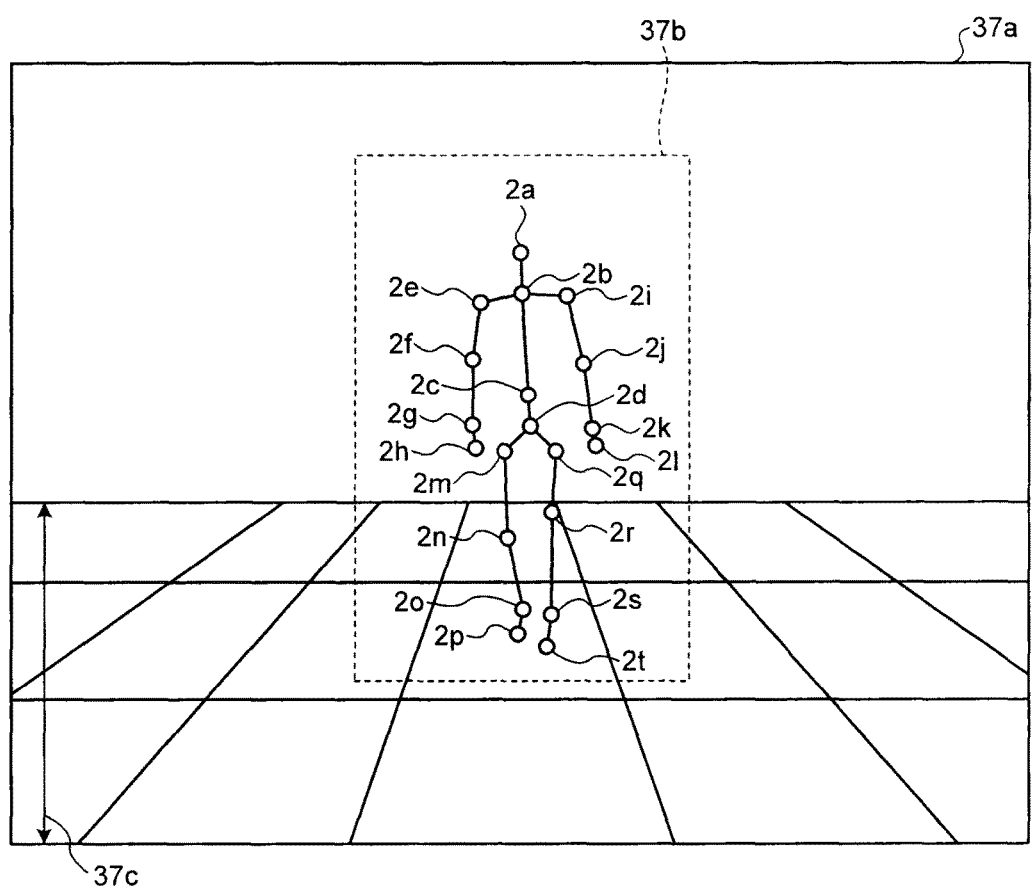
FIG. 37B is a diagram for explaining processing performed by the generation circuitry according to the eleventh embodiment.

FIGS. 37A and 37B are diagrams for explaining processing performed by the generation circuitry 342 according to the eleventh embodiment. FIG. 37A illustrates color image information presenting a state in which a test subject is carrying out gait training and skeleton information indicating the positions of joints of the test subject. FIG. 37B illustrates medical image information 37a generated on the basis of the color image information and skeleton information in FIG. 37A.

As illustrated in FIGS. 37A and 37B, the generation circuitry 342 generates a skeleton model 37b indicating the positions of joints 2a to 2t contained in the skeleton information obtained by the obtaining circuitry 341. Specifically, for example, the generation circuitry 342 places circles at positions corresponding to pixel positions X and pixel positions Y of the joints 2a to 2t in a photographed range of the medical image information 37a. The generation circuitry 342 also places lines connecting the circles on the basis of information indicating relative positions of the joints. As a result, the generation circuitry 342 generates the skeleton model 37b.

The generation circuitry 342 also generates a floor surface image 37c. Specifically, for example, the generation circuitry 342 specifies a pixel corresponding to the position of y=0 in the world coordinate system as a pixel of a floor surface. The generation circuitry 342 then generates the floor surface image 37c by placing parallel lines at intervals of 1 m in the x direction and the z direction among the pixels of the floor surface.

In this manner, the generation circuitry 342 generates the medical image information 37a containing the skeleton model 37b and the floor surface image 37c. The generation circuitry 342 then outputs the generated medical image information 37a to the output control circuitry 343.

Note that the above example is only an example, and the embodiment is not limited thereto. For example, the process in which the generation circuitry 342 generates the floor surface image 37c is not limited to the above example. For example, in a case where coordinates of the floor surface in the world coordinate system can be obtained from the motion information collector 10 or other sensors, the generation circuitry 342 may specify the pixels by using the obtained coordinates. The generation circuitry 342 can generate the floor surface image 37c by placing parallel lines at intervals of 1 m in the x direction and the z direction among the specified pixels of the floor surface. Furthermore, alternatively, the generation circuitry 342 may specify pixels corresponding to positions where the position of a tarsus (the joint 2p or the joint 2t) of a test subject does not change for a predetermined time as pixels of the floor surface, for example. Alternatively, for example, the floor surface image 37c need not necessarily be contained in the medical image information 37a.

The output control circuitry 343 outputs motion information for browsing containing skeleton information and medical image information in time series. In one example, the output control circuitry 343 associates the skeleton information of the test subject and the medical image information 37a generated by the generation circuitry 342 in time series, and stores the association result as the motion information for browsing in the medical image archiving device 20. Note that the motion information for browsing is an example of second motion information.

FIG. 38 is a table illustrating an example of motion information for browsing stored in the medical image archiving device 20 according to the eleventh embodiment. The medical image archiving device 20 stores information in which a name number, a date, and motion information for browsing are associated with each name as illustrated in FIG. 38. Note that the "name number" refers to an identifier for uniquely identifying a test subject, and is assigned to each name. The "date" refers to the date and time when the test subject has carried out gait training. The "motion information for browsing" refers to information stored in the medical image archiving device 20 by the output control circuitry 343.

As illustrated in FIG. 38, the medical image archiving device 20 stores a name "A," a name number "1," a date "20120801_1," motion information for browsing "medical image information, depth image information, speech recognition result, skeleton information" and the like. The above information indicates that motion information for browsing containing "medical image information," "depth image information," a "speech recognition result," and "skeleton information" is stored as motion information in the "first" gait training carried out by a person with a name "A" whose name number is "1" on "Aug. 1" in "2012." Note that, in the motion information for browsing illustrated in FIG. 38, the "medical image information," the "depth image information," the "speech recognition result" and the "skeleton information" for each of all the frames photographed during the gait training are stored in association with time in time series.

In this manner, the output control circuitry 343 associates the skeleton information of the test subject and the medical image information 37a generated by the generation circuitry 342 in time series, and stores the association result as the motion information for browsing in the medical image archiving device 20. Alternatively, the output control circuitry 343 may display the motion information for browsing on the output circuitry 110.

Figure 39:
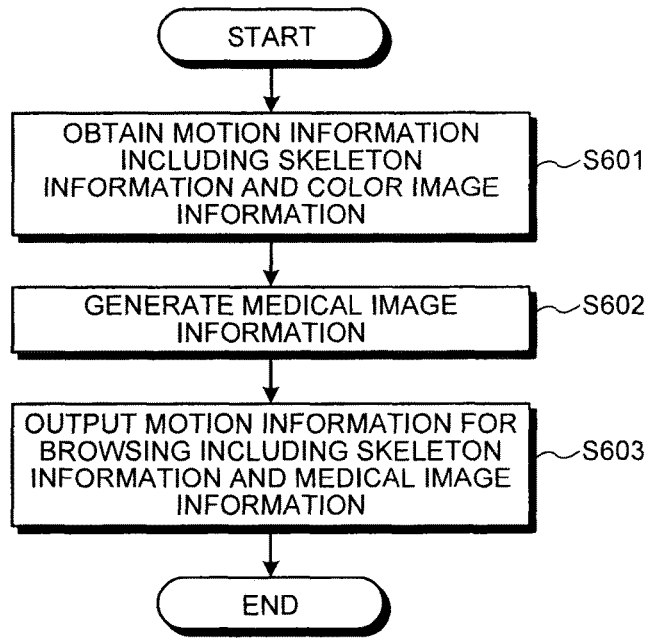
FIG. 39 is a flowchart illustrating procedures of processing performed by the motion information processing device according to the eleventh embodiment.

FIG. 39 is a flowchart illustrating procedures of processing performed by the motion information processing device 300 according to the eleventh embodiment. As illustrated in FIG. 39, the obtaining circuitry 341 obtains motion information containing skeleton information and color image information (step S601).

Subsequently, the generation circuitry 342 generates medical image information with which a motion of a test subject can be confirmed without containing personal information of the test subject (step S602). For example, the generation circuitry 342 generates image information, with which the skeleton of a test subject can be visually confirmed, as medical image information by using the positions of joints contained in the skeleton information.

The output control circuitry 343 then outputs motion information for browsing containing skeleton information and medical image information in time series (step S603). For example, the output control circuitry 343 associates the skeleton information of the test subject and the medical image information 37a generated by the generation circuitry 342 in time series, and stores the association result as the motion information for browsing in the medical image archiving device 20.

As described above, the motion information processing device 300 according to the eleventh embodiment obtains motion information containing skeleton information and color image information. The motion information processing device 300 then generates medical image information with which a motion of a test subject can be confirmed without containing personal information of the test subject on the basis of at least one of the skeleton information and the color image information. Thus, the motion information processing device 300 can provide information with which a motion can be confirmed while hiding personal information of a test subject.

Specifically, since the test subject is photographed in color image information, the test subject can be identified by viewing the color image information. It is thus undesirable in terms of protection of personal information to hold the color image information in the medical image archiving device 20. Thus, the motion information processing device 300 according to the eleventh embodiment generates the medical image information 37a with which a motion of a test. subject can be confirmed without containing the photographed test subject, and stores the generated medical image information 37a instead of the color image information in the medical image archiving device 20. The motion information processing device 300 according to the eleventh embodiment can therefore provide information with which a motion can be confirmed while hiding personal information of a test subject. As a result, since a test subject is not identified when the medical image information 37a of the subject is viewed by others, the motion information processing device 300 can provide image information that is clinically useful while protecting personal information of the test subject. Specifically, a doctor can show the medical image information 37a of a test subject as a good example to another test subject or as a guideline such as "a healthier condition one month later as a result of carrying out the rehab."

Furthermore, for example, the motion information processing device 300 according to the eleventh embodiment stores motion information for browsing in the medical image archiving device 20 in consideration of protection of personal information, which allows processing of motion information for browsing of multiple test subjects. As a result, the motion information processing device 300 allows feature quantities of each individual or each disease, for example, to be obtained more accurately by statistically processing the motion information for browsing.

Furthermore, as described above, in a case where the medical image archiving device 20 is provided on a network such as the Internet of a LAN, the motion information processing device 300 can store clinically-useful image information in the medical image archiving device 20 on the network while protecting personal information of test subjects. As a result, the motion information processing device 300 can share information with remote medical institutions. For example, it is possible to share information on a common subject among doctors and physical therapists in regional cooperation, and get advice from a remote doctor, for example.

Modified Example 1 of Eleventh Embodiment

Although a case in which the motion information processing device 300 generates medical image information 37a containing a skeleton model 37b has been described in the embodiment above, the embodiment is not limited thereto. For example, the motion information processing device 300 may generate image information in which a part of the image containing features of the test subject included in the color image information is hidden, as the medical image information. Note that the part containing features of the test subject is the head (face), for example. In the following, a case in which the motion information processing device 300 generates image information in which the image of the head of a test subject contained in color image information is hidden will be described as an example.

In the motion information processing device 300 according to modified example 1 of the eleventh embodiment, the generation circuitry 342 generates image information in which at least part of an image of the head of a test subject contained in color image information is hidden, as medical image information, by using the position of the joint at the head contained in the skeleton information.

Figure 40:
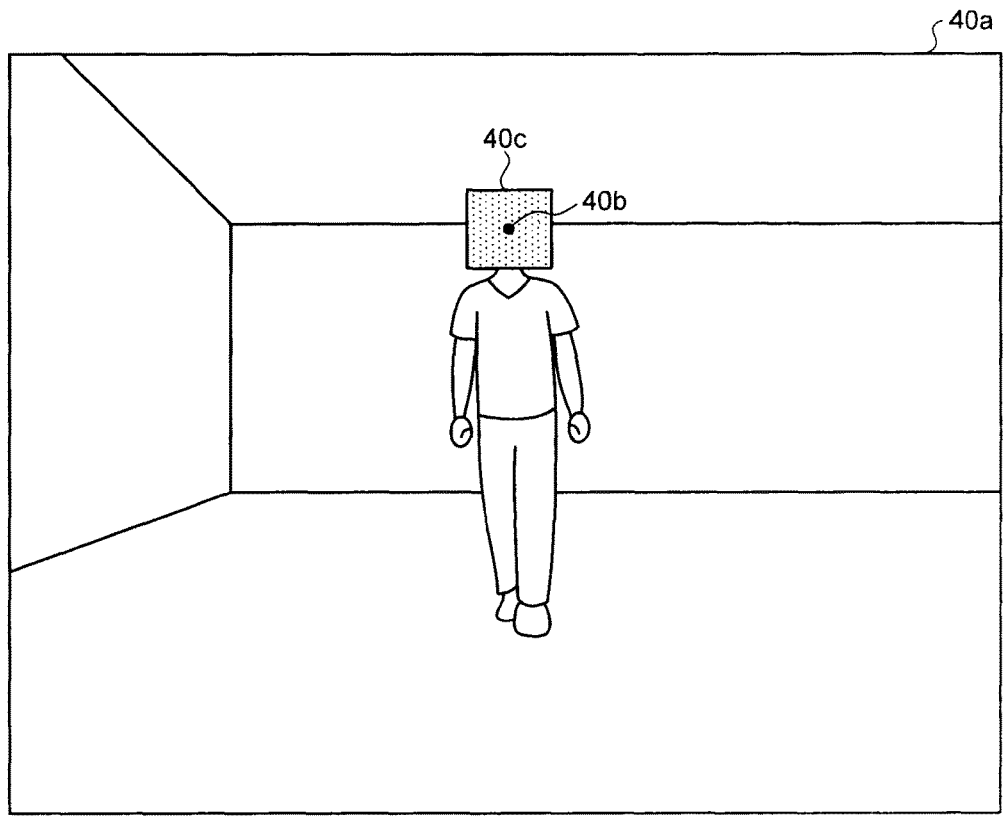
FIG. 40 is a diagram for explaining processing performed by generation circuitry according to a modified example 1 of the eleventh embodiment.

FIG. 40 is a diagram for explaining processing performed by the generation circuitry 342 according to the modified example 1 of the eleventh embodiment. FIG. 40 illustrates medical image information 40a generated on the basis of the color image information and skeleton information in FIG. 37A.

As illustrated in FIG. 40, the generation circuitry 342 hides an image of the head of a test subject contained in color image information by using the position of the joint at the head of the test subject contained in the skeleton information obtained by the obtaining circuitry 341. Specifically, the generation circuitry 342 specifies a pixel position 40b at the center of the head in the color image information by using the coordinates of the joint 2a of the head contained in the skeleton information. The generation circuitry 342 then changes the color of pixels contained in a head area 40c containing the pixel position 40b to a predetermined color (gray, for example). The head area 40c is a rectangular area of a predetermined size having the pixel position 40b at the center, for example. The generation circuitry 342 then outputs the color image information resulting from changing the color of the pixels contained in the head area 40c as the medical image information 40a to the output control circuitry 343. As a result, the output control circuitry 343 associates the skeleton information of the test subject and the medical image information 40a generated by the generation circuitry 342 in time series, and stores the association result as the motion information for browsing in the medical image archiving device 20.

As described above, the motion information processing device 300 according to the modified example 1 of the eleventh embodiment generates the medical image information 40a by hiding the image of the head of the test subject contained in the color image information. Specifically, the motion information processing device 300 generates medical image information with which a motion of a test subject can be confirmed without containing personal information of the test subject on the basis of at least one of the skeleton information and the color image information. The motion information processing device 300 then stores the generated medical image information instead of the color image information in the medical image archiving device 20. The motion information processing device 300 according to the eleventh embodiment can therefore provide information with which a motion can be confirmed while hiding personal information of a test subject.

Note that the size of the head area 40c can be changed to any size determined by an operator of the motion information processing device 300. Alternatively, the size of the head area 40c may be changed according to the value of the z coordinate of the joint 2a. In this case, for example, the motion information processing device 300 sets the head area 40c to be small if the z coordinate value of the joint 2a is large (if the test subject is far), or sets the head area 40c to be large if the z coordinate value of the joint 2a is small (if the test subject is close). Furthermore, although it is preferable that the size of the head area 40c be large enough to hide the entire head, the size is not limited thereto, and the head area 40c may have such a size that only hides the position of the eyes. Furthermore, the shape of the head area 40c need not necessarily be a rectangle. For example, the shape of the head area 40c may be a circle, or the contour of the face may be determined by a face recognition technology with the joint 2a at the center, and a range corresponding to the determined contour may be defined as the head area 40c.

Furthermore, although a case in which image information in which the image of the head is hidden as one example of the part containing features of a test subject has been described here, the embodiment is not limited thereto. For example, the motion information processing device 300 may detect a feature of a physical skeleton shape as the part containing features of the test subject, and hide the detected feature. Examples of a feature of the physical skeleton shape include loss of an arm. For example, for a test subject whose left arm is lost, the motion information processing device 300 generates image information in which a part containing a feature of the test subject is hidden by hiding the position corresponding to the left arm. For example, the generation circuitry 342 refers to the skeleton information of the test subject, and determines whether or not position information on all of the joints 2a to 2t is present. If the joints 2j, 2k, and 2l are not present, the generation circuitry 342 estimates the positions of the joints 2j, 2k, and 2l of the test subject. In one example, the generation circuitry 342 estimates the positions that are symmetrical with the positions of the joints 2f, 2g, and 2h of the right arm about a center line of the body (a line passing through the joints 2b and 2c to be the positions of the joints 2j, 2k, and 2l. The generation circuitry 342 then changes the color of the pixels contained in an area (a rectangular area, for example) containing the estimated joints 2j, 2k, and 2l of the left arm to a predetermined color. In this manner, the generation circuitry 342 generates image information in which the position corresponding to the left arm of the test subject is hidden.

Alternatively, for example, the motion information processing device 300 may detect a feature appearing on the skin of the test subject as a part containing the feature of the test subject, and hide the detected feature. A feature appearing on the skin is a scar (due to an injury) or the like. For example, for a test subject whose left arm has a scar, the motion information processing device 300 generates image information in which a part containing a feature of the test subject is hidden by hiding the position corresponding to the left arm. For example, the generation circuitry 342 generates a pixel histogram for an area of the color image information containing the positions corresponding to skeleton information of a test subject. When a peak is detected from a luminance histogram corresponding to the skin color, the generation circuitry 342 then changes the color of pixels in the area containing the position corresponding to the peak to a predetermined color. This is because, while a uniform luminance histogram can be obtained for a normal skin, a feature of the skin such as a car is considered present when a peak is detected from the luminance histogram. In this manner, the generation circuitry 342 generates image information in which the position corresponding to the left arm of the test subject is hidden.

Furthermore, the motion information processing device 300 is not limited to the examples above, and may generate image information in which an area specified by an operator is hidden. In one example, the generation circuitry 342 receives specification of an area from the operator via the input circuitry 120 such as a mouse. The generation circuitry 342 then generates image information in which the received area is hidden.

Furthermore, the generation circuitry 342 according to the modified example 1 of the eleventh embodiment may generate image information containing the floor surface image 37c described above as medical image information. For example, the generation circuitry 342 can generate the floor surface image 37c as described above and generate image information in which the generated floor surface image 37c is superimposed on the medical image information 40a.

Modified Example 2 of Eleventh Embodiment

Furthermore, there are cases in which color image information contains a photographed person or object other than test subjects, which should not be disclosed. For example, color image information may contain the face of a caregiver assisting rehab of a test subject or a notice or the like that should not be disclosed. Thus, in addition to the modified example 1 of the eleventh embodiment, the motion information processing device 300 may generate image information in which an area in which a person or an object other than a test subject is photographed contained in color image information is hidden, as medical image information.

In the motion information processing device 300 according to modified example 2 of the eleventh embodiment, the generation circuitry 342 further generates image information in which at least part of an image of a person or an object other than a test subject contained in color image information is photographed is hidden, as medical image information, by using the position of the joints contained in the skeleton information.

Figure 41:
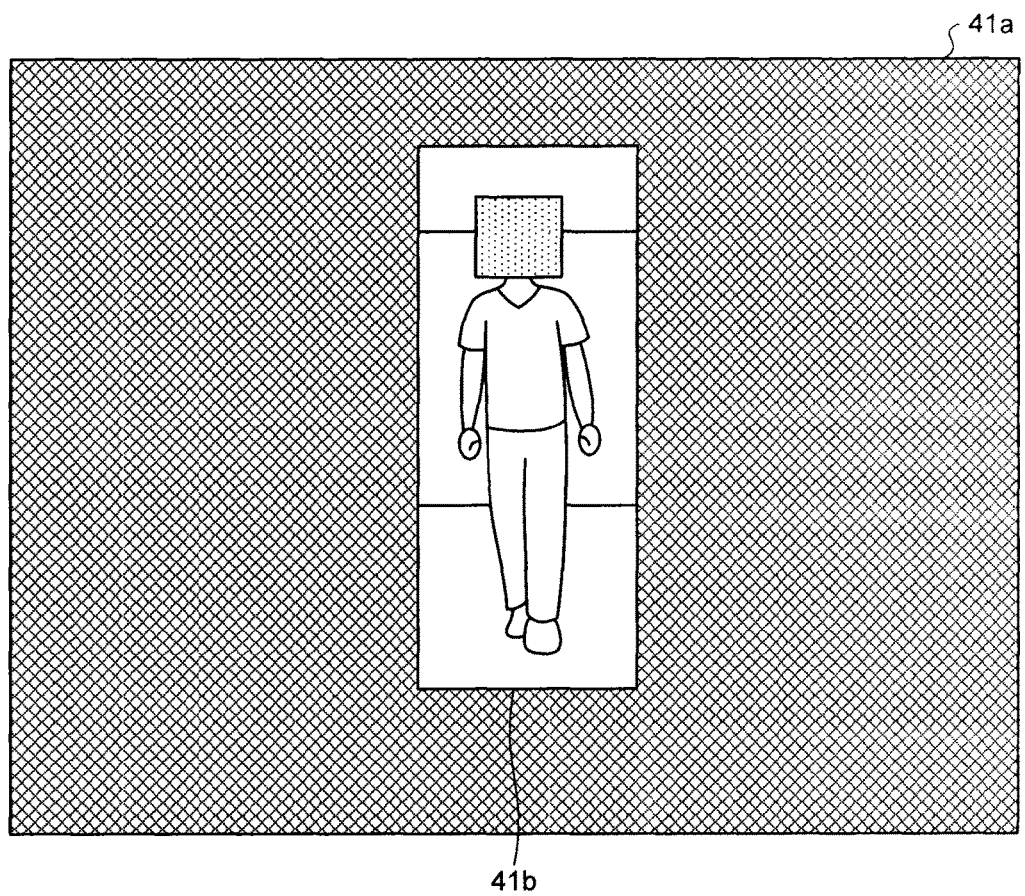
FIG. 41 is a diagram for explaining processing performed by generation circuitry according to a modified example 2 of the eleventh embodiment.

FIG. 41 is a diagram for explaining processing performed by the generation circuitry 342 according to the modified example 2 of the eleventh embodiment. FIG. 41 illustrates medical image information 41a generated on the basis of the medical image information 40a in FIG. 40.

As illustrated in FIG. 41, the generation circuitry 342 further hides an image in which a person or an object other than a test subject contained in color image information is photographed by using the positions of the joints contained in the skeleton information. Specifically, the generation circuitry 342 specifies a test subject area 41b containing a test subject by using the positions of the joints contained in skeleton information. More specifically, the generation circuitry 342 specifies a joint with the largest x coordinate value of the x coordinates of the joints of the test subject, and determines a line passing through a coordinate obtained by adding a predetermined value to the x coordinate value of the specified joint to be the right side of the test subject area 41b. The generation circuitry 342 also specifies a joint with the smallest x coordinate value of the x coordinates of the joints of the test subject, and determines a line passing through a coordinate obtained by subtracting a predetermined value to the x coordinate value of the specified joint to be the left side of the test subject area 41b. The generation circuitry 342 also specifies a joint with the largest y coordinate value of the y coordinates of the joints of the test subject, and determines a line passing through a coordinate obtained by adding a predetermined value to the y coordinate value of the specified joint to be the upper side of the test subject area 41b. The generation circuitry 342 also specifies a joint with the smallest y coordinate value of the y coordinates of the joints of the test subject, and determines a line passing through a coordinate obtained by subtracting a predetermined value to the y coordinate value of the specified joint to be the lower side of the test subject area 41b. The generation circuitry 342 then changes the color of pixels outside of the specified test subject area 41b to a predetermined color (gray, for example). The generation circuitry 342 then outputs the color image information resulting from changing the color of the pixels outside of the test subject area 41b as the medical image information 41a to the output control circuitry 343. As a result, the output control circuitry 343 associates the skeleton information of the test subject and the medical image information 41a generated by the generation circuitry 342 in time series, and stores the association result as the motion information for browsing in the medical image archiving device 20.

In this manner, the motion information processing device 300 according to the modified example 2 of the eleventh embodiment generates medical image information 41a by hiding an area in which a person or an object other than a test subject is photographed, and stores the generated medical image information 41a instead of the color image information in the medical image archiving device 20. The motion information processing device 300 according to the eleventh embodiment can therefore provide information with which a motion of a test subject can be confirmed while hiding a photographed person or object other than the test subject, which should not be disclosed. For example, the motion information processing device 300 can also hide the face of a caregiver assisting rehab of test subject a or a notice or the like that should not be disclosed.

Note that the size of the test subject area 41b can be changed to any size determined by an operator of the motion information processing device 300. Furthermore, the shape of the test subject area 41b need not necessarily be a rectangle. For example, the shape of the test subject area 41b may be an ellipse.

Furthermore, the generation circuitry 342 according to the modified example 2 of the eleventh embodiment may generate image information containing the floor surface image 37c described above as medical image information. For example, the generation circuitry 342 can generate the floor surface image 37c as described above and generate image information in which the generated floor surface image 37c is superimposed on the medical image information 41a.

Modified Example 3 of Eleventh Embodiment

Furthermore, the embodiment is not limited to the embodiments described above, and the motion information processing device 300 may generate image information presenting only a test substrate area as medical image information, for example.

In the motion information processing device 300 according to the modified example 3 of the eleventh embodiment, the obtaining circuitry 341 obtains motion information further containing pixels contained in a photographed range and depth image information in which the pixels and depths are associated with each other in time series. For example, each time the motion information collector 10 and the motion information processing device 300 are powered on and depth information of one frame is stored in the motion information storage circuitry 331, the obtaining circuitry 341 obtains the stored depth image information from the motion information storage circuitry 331.

In the motion information processing device 300 according to the modified example 3 of the eleventh embodiment, the generation circuitry 342 generates image information representing an area of a test subject as medical image information from the depth image information at the time point when the medical image information is processed on the basis of the depth image information at the time point when the medical image information is processed and depth image information at a time point different from the aforementioned depth image information.

Figure 42:
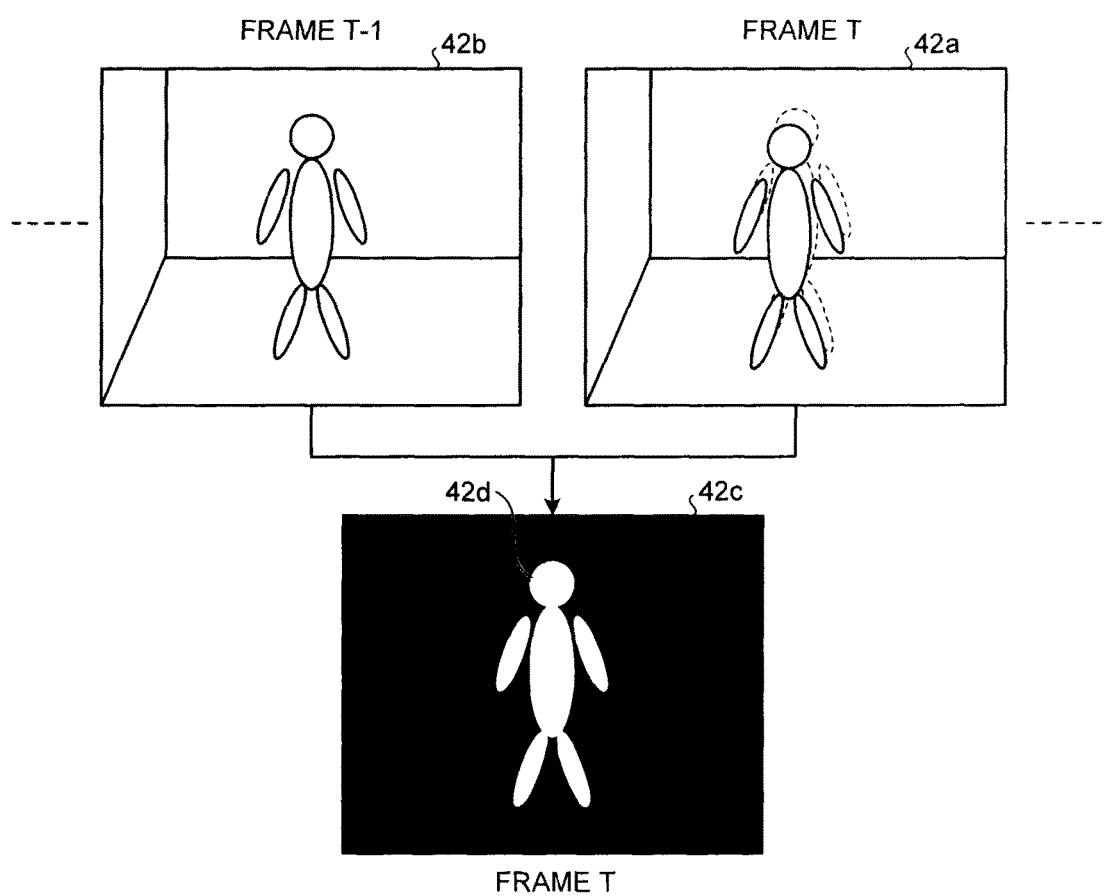
FIG. 42 is a diagram for explaining processing performed by generation circuitry according to a modified example 3 of the eleventh embodiment.

FIG. 42 is a diagram for explaining processing performed by the generation circuitry 342 according to the modified example 3 of the eleventh embodiment. FIG. 42 illustrates a depth image 42a of a frame T, and a depth image 42b and a binarized image 42c of a frame T−1. In the depth image 42a of the frame T and the depth image 42b of the frame T−1, a solid line represents the position of a test subject in each frame. In addition, in the depth image 42a of the frame T, a broken line represents the position of the test subject in the frame T−1. Thus, the depth image 42a of the frame T indicates that the test subject has moved from the position of the broken line to the position of the solid line. Note that a "pixel position X" and a "pixel position Y" in the binarized image 42c correspond to a "pixel position X" and a "pixel position Y" in the distance image coordinate system. In addition, the broken line indicates the position of the test subject in the frame T−1 for convenience, and the position of the test subject in the frame T−1 is not illustrated in the depth image 42a of the frame T.

As illustrated in FIG. 42, when the depth image 42a of the frame T is obtained by the obtaining circuitry 341, the generation circuitry 342 subtracts the depth of the depth image 42b of the frame T−1 from the depth of the depth image 42a of the frame T for each pixel. The generation circuitry 342 then generates the binarized image 42c of the frame T by performing binarization of setting pixels with values as a result of subtraction are not smaller than a threshold to white and setting pixels with values smaller than the threshold to black. In the binarized image 42c, an area of black pixels represents a position of an object that has moved less than a threshold in the depth direction between the frame T−1 and the frame T, that is, an object such as the floor surface, a wall, a desk, or a chair. An area of white pixels represents a position of a photographed person (a photographed person or object) that has moved equal to or more than the threshold in the depth direction between the frame T−1 and the frame T. Specifically, the generation circuitry 342 extracts a test subject area 42d representing the position of a test subject carrying out a walking motion by identifying an object that has not moved and an object that has moved. The generation circuitry 342 then outputs the binarized image 42c from which the test subject area 42d has been extracted as medical image information to the output control circuitry 343. As a result, the output control circuitry 343 associates the skeleton information of the test subject and the medical image information generated by the generation circuitry 342 in time series, and stores the association result as the motion information for browsing in the medical image archiving device 20.

In this manner, the motion information processing device 300 according to the modified example 3 of the eleventh embodiment generates image information indicating only an area of a test subject as medical image information, and stores the medical image information instead of the color image information in the medical image archiving device 20. The motion information processing device 300 according to the eleventh embodiment can therefore provide information with which a motion can be confirmed while hiding personal information of a test subject.

Note that the processing of the generation circuitry 342 is only an example, and is not limited thereto. For example, although the generation circuitry 342 extracts the test subject area by using depth image information of successive frames in time series in the above description, the extraction is not limited thereto. For example, the generation circuitry 342 may calculate the difference in depth for each pixel between depth image information data of frames separated by several frames in time series, and extract a pixel area where the calculated difference is equal to or larger than a threshold as the test subject area. Alternatively, for example, the generation circuitry 342 may use depth image information in which no person is present as a reference, calculate the difference in depth for each pixel between the depth image information of the frame T and the reference depth image information, and extract a pixel area where the calculated difference is equal to or larger than a threshold as the test subject area.

Furthermore, the generation circuitry 342 according to the modified example 3 of the eleventh embodiment may generate image information containing the floor surface image 37c described above as medical image information. For example, the generation circuitry 342 can generate the floor surface image 37c as described above and generate image information in which the generated floor surface image 37c is superimposed on the binarized image 42c.

Twelfth Embodiment

Although a case in which the motion information processing device 300 hides personal information of a test subject when storing motion information for browsing in the medical image archiving device 20 has been described in the above embodiment, the embodiment is not limited thereto. For example, when motion information for browsing of another test subject is shown as a good example to a test subject at the workstation 30, an image of the test subject may be displayed on the basis of the motion of the motion information for browsing that is a good example. As a result, the test subject can view an image in which the test subject himself/herself moves as if the test subject is carrying out a motion of the good example.

A medical information processing system 1 according to the twelfth embodiment has a configuration similar to that of the medical information processing system 1 illustrated in FIG. 35, but differs therefrom in part of processing at the workstation 30. In the twelfth embodiment, the description will be focused mainly on the difference from the eleventh embodiment, and components having the same functions as those described in the eleventh embodiment will be designated by the same reference numerals as those in FIG. 35 and the description thereof will not be repeated.

Figure 43:
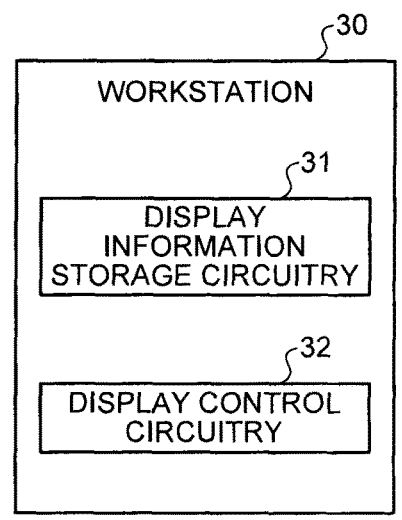
FIG. 43 is a block diagram illustrating a detailed example configuration of a workstation according to a twelfth embodiment.

FIG. 43 is a block diagram illustrating a detailed example configuration of the workstation 30 according to the twelfth embodiment. As illustrated in FIG. 43, the workstation 30 includes display information storage circuitry 31 and display control circuitry 32.

The display information storage circuitry 31 stores display information in which test subject image information representing a test subject and the positions of joints of the test subject in the test subject image information are associated.

Figure 44:
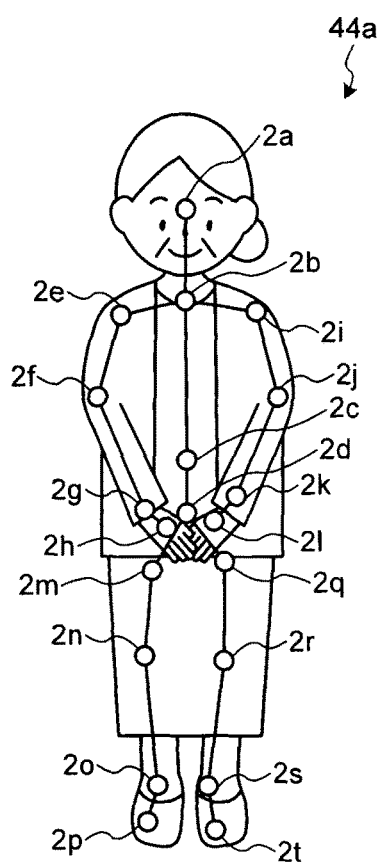
FIG. 44 is a diagram illustrating an example of information stored in display information storage circuitry.

FIG. 44 is a diagram illustrating an example of information stored in the display information storage circuitry 31. In FIG. 44, a case in which the test subject is an elderly female will be described. In this case, the display information storage circuitry 31 stores information in which image information of the test subject and the positions of the joints 2a to 2t of the test subject are associated as display information 44a. Specifically, the display information storage circuitry 31 stores positional relations of the positions of the joints of the test subject and the positions of the pixels contained in the image information of the test subject.

Although the display information 44a containing a character of an elderly female as test subject image information is presented in the example illustrated in FIG. 44 for convenience of explanation, the embodiment is not limited thereto. For example, male and female characters c all age groups such as 0 to 9 years old, 10 to 19 years old, 20 to 29 years old, and so on may be provided in the display information storage circuitry 31 in such a manner that the characters can be selected according to the age and sex of the test subject. Furthermore, alternatively, the display information storage circuitry 31 may store the display information 44a containing a photograph of the test subject as test subject image information.

The display control circuitry 32 obtains motion information for browsing from the medical image archiving device 20. The display control circuitry 32 then performs display control to display an image of the test subject on the basis of the motion information for browsing by mapping image information on the test subject on the medical image information contained in the motion information for browsing on the basis of the positions of joints contained in the display information.

Figure 45:
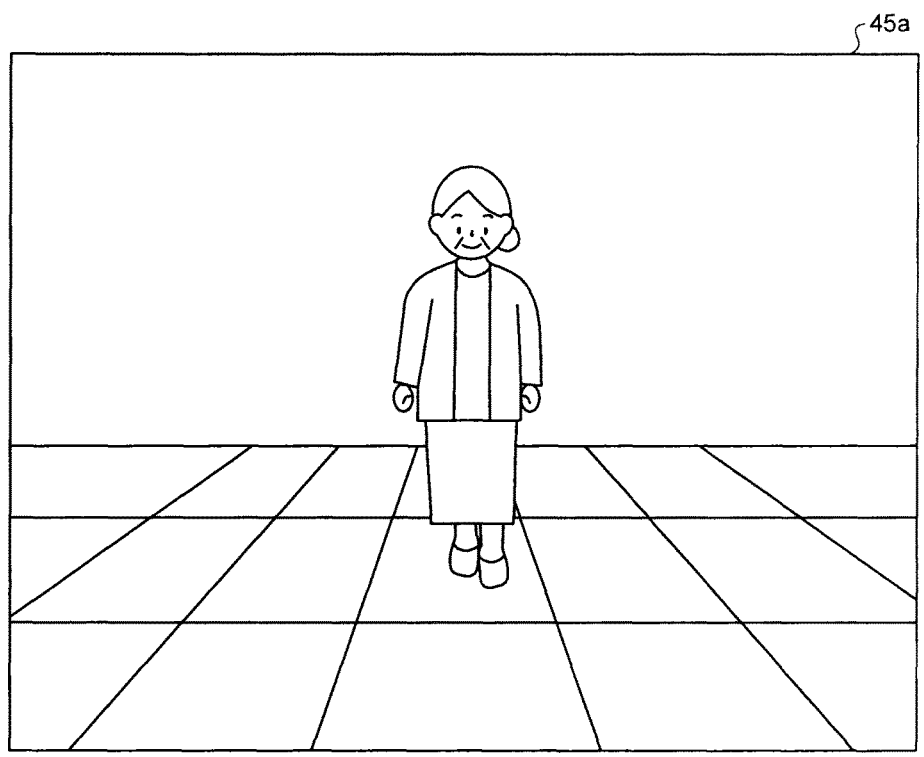
FIG. 45 is a diagram for explaining processing performed by display control circuitry according to the twelfth embodiment.

FIG. 45 is a diagram for explaining processing performed by the display control circuitry 32 according to the twelfth embodiment. FIG. 45 illustrates a display image 45a that is browsed by a test subject at the workstation 30. In FIG. 45, a case in which pixels contained in the display information 44a in FIG. 44 on the medical image information 37a in FIG. 37B will be explained as an example.

As illustrated in FIG. 45, for example, the display control circuitry 32 obtains motion information for browsing from the medical image archiving device 20. The motion information for browsing contains the medical image information 37a in FIG. 37B. The display control circuitry 32 then performs mapping of image information of the test subject on the medical image information 37a on the basis of the positions of the joints contained in the display information 44a stored in the display information storage circuitry 31. Specifically, the display control circuitry 32 positions the pixels contained in the display information 44a on the medical image information 37a on the basis of the positional relation between the pixel positions of the pixels and the positions of the joints. More specifically, for example, the display control circuitry 32 positions the pixels at the position of the joint 2a in the display information 44a at the position of the joint 2a of the head in the medical image information 37a. Furthermore, for example, the pixels at the positions of hair in the display information 44a are positioned at positions of ΔX and ΔY from the position of the head in the medical image information 37a by using the positional relation of the pixels and the position of the joint 2a of the head (a distance ΔX in the X direction and a distance ΔY in the Y direction). As a result, the display control circuitry 32 generates the display image 45a that displays the display information 44a of an elderly female with the posture of the medical image information 37a. The display control circuitry 32 generates a floor surface image by the same processing as that of the generation circuitry 342 according to the first embodiment, and superimposes the generated floor surface image on the display image 45a. The display control circuitry 32 then displays the display image 45a on which the floor surface image is superimposed in time series to display a moving image appearing as if the elderly female is carrying out the motion of the medical image information 37a. Note that the display control circuitry 32 need not necessarily generates a floor surface image.

As described above, the workstation 30 according to the twelfth embodiment, the image information of a test subject is displayed on the basis of the motion of the motion information for browsing of another test subject. Thus, the workstation 30 can display, to a test subject, an image appearing as if the test subject is carrying out a motion of another test subject. As a result, since the image appears to the test subject as if the test subject is carrying out a motion of another person, the test subject can easily and practically visualize himself/herself, in a healthier condition, in a month time after starting rehab. As a result, the motion information processing device 300 can encourage motivation of the test subject who carries out rehab.

Although a case in which the display control circuitry 32 displays the display image 44a on the basis of the medical image information 37a in FIG. 37B has been described in the twelfth embodiment, the embodiment is not limited thereto. For example, the display control circuitry 32 may display the display image 44a on the basis of the medical image information 40a in FIG. 40 or may display the display image 44a on the basis of the binarized image 42c in FIG. 42. Alternatively, the display control circuitry 32 may obtain motion information from the motion information processing device 300 and display the display image 44a on the basis of color image information and skeleton information, for example. In this case, the display control circuitry 32 performs the processing of the display control circuitry 32 after performing the processing of the generation circuitry 342.

As described above, according to the eleventh and twelfth embodiments, the motion information processing device of the present embodiment can provide information with which a motion can be confirmed while hiding personal information of a test subject.

Thirteenth Embodiment

As described above, in the first to sixth embodiments, a case of allowing prevention of falsely recognizing a person or object other than the person carrying out a predetermined motion has been described. Furthermore, in the seventh to tenth embodiments, a case of determining whether or not a digitally recorded motion of a person is that of a subject of rehabilitation has been described. Furthermore, in the eleventh and twelfth embodiments, a case in which a digitally recorded motion of a person provides information with which a motion can be confirmed while hiding personal information of a test subject has been described. Note that the processes described above can be performed as a series of processes. Thus, in a thirteenth embodiment, a case in which the processes described above are performed as a series of processes will be described. As a result, a motion information processing device 400 according to the thirteenth embodiment can reliably determine motion information of a rehab subject, and further hide personal information of the rehab subject. Note that, in the thirteenth embodiment, a person carrying out a predetermined motion will be referred to as a "subject," and a subject of rehabilitation will be referred to as a "rehab subject."

Figure 46:
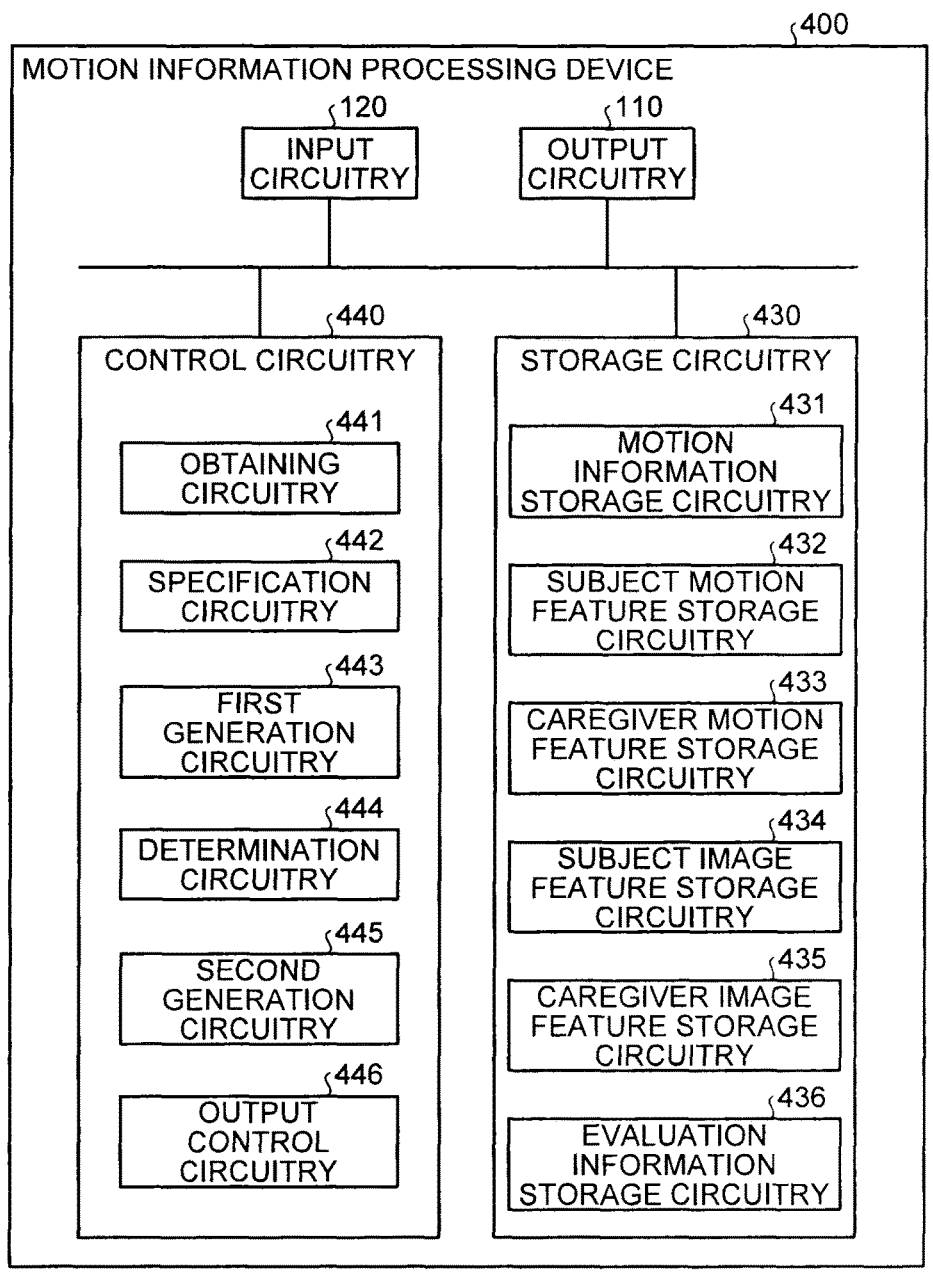
FIG. 46 is a block diagram illustrating a detailed example configuration of a motion information processing device according to a thirteenth embodiment.

FIG. 46 is a block diagram illustrating an example configuration of the motion information processing device 400 according to the thirteenth embodiment. As illustrated in FIG. 46, the motion information processing device 400 is an information processing device such as a computer or a workstation, and includes output circuitry 110, input circuitry 120, storage circuitry 430, and control circuitry 440. Since the output circuitry 110 and the input circuitry 120 are similar to those described in the first embodiment, the description thereof will not be repeated.

The storage circuitry 430 has a configuration similar to that of the storage circuitry 230 illustrated in FIG. 19. Specifically, the storage circuitry 430 includes motion information storage circuitry 431, subject motion feature storage circuitry 432, caregiver motion feature storage circuitry 433, subject image feature storage circuitry 434, caregiver image feature storage circuitry 435, and evaluation information storage circuitry 436. In the thirteenth embodiment, since the motion information storage circuitry 431, the subject motion feature storage circuitry 432, the caregiver motion feature storage circuitry 433, the subject image feature storage circuitry 434, the caregiver image feature storage circuitry 435, and the evaluation information storage circuitry 436 are the same as the motion information storage circuitry 231, the subject motion feature storage circuitry 232, the caregiver motion feature storage circuitry 233, the subject image feature storage circuitry 234, the caregiver image feature storage circuitry 235, and the evaluation information storage circuitry 236 illustrated in FIG. 19, the description thereof will not be repeated.

The control circuitry 440 includes obtaining circuitry 441, specification circuitry 442, first generation circuitry 443, determination circuitry 444, second generation circuitry 445, and output control circuitry 446.

The obtaining circuitry 441 has the same functions as those of the obtaining circuitry 141 illustrated in FIG. 4. For example, the obtaining circuitry 441 obtains motion information stored in the motion information storage circuitry 431. Note that the obtaining circuitry 441 need not necessarily obtain motion information containing all of the color image information, the distance image information, the speech recognition result, and the skeleton information. For example, the obtaining circuitry 441 may obtain at least one of the color image information, the distance image information, the speech recognition result, and the skeleton information, where necessary.

The specification circuitry 442 has the same functions as those of the specification circuitry 142 illustrated in FIG. 4. For example, the specification circuitry 442 specifies motion information of the subject carrying out the predetermined motion on the basis of predetermined features in the image information obtained by the obtaining circuitry 441.

The first generation circuitry 443 has the same functions as those of the generation circuitry 242 illustrated in FIG. 19. For example, the first generation circuitry 443 generates evaluation information for evaluating rehabilitation from the motion information specified by the specification circuitry 442.

The determination circuitry 444 has the same functions as those of the determination circuitry 243 illustrated in FIG. 19. For example, the determination circuitry 444 determines whether or not a person associated with motion information specified by the specification circuitry 442 is a subject of rehabilitation by using information indicating a feature of a rehab subject that is a subject of rehabilitation.

The second generation circuitry 445 has the same functions as those of the generation circuitry 342 illustrated in FIG. 36. For example, the second generation circuitry 445 generates medical image information with which a motion of a subject can be confirmed without containing personal information of the subject on the basis of at least one of skeleton information representing a skeleton of a human body, and color image information in which the subject is photographed contained in time series in the motion information specified by the specification circuitry 442. Furthermore, for example, the second generation circuitry 445 generates medical image information of the subject on the basis of at least one the skeleton information and color image information contained in time series in motion information determined to correspond to the subject by the determination circuitry.

The output control circuitry 446 has the functions of the display control circuitry 143 illustrated in FIG. 4, the functions of the storage circuitry 244 illustrated in FIG. 19, and the functions of the output control circuitry 343 illustrated in FIG. 36. The output control circuitry 446 performs output control where appropriate.

For example, when the motion information of the subject is specified by the specification circuitry 442, the output control circuitry 446 performs control to display a display image in which information indicating the subject is superimposed on the image information at a position corresponding to the motion information specified by the specification circuitry 442.

When determination is performed by the determination circuitry 444, the output control circuitry 446 also output a determination result of determination by the determination circuitry 444, for example. Specifically, the output control circuitry 446 associates the evaluation information generated by the first generation circuitry 443 and the determination result of determination by the determination circuitry 444 with each other, and stores the association result in the evaluation information storage circuitry 436.

Furthermore, when medical image information is generated by the second generation circuitry 445, the output control circuitry 446 outputs motion information for browsing containing skeleton information and the medical image information in time series, for example. In one example, the output control circuitry 446 associates skeleton information of a test subject and medical image information generated by the second generation circuitry 445 in time series, and stores the association result as motion information for browsing in the medical image archiving device 20.

Figure 47:
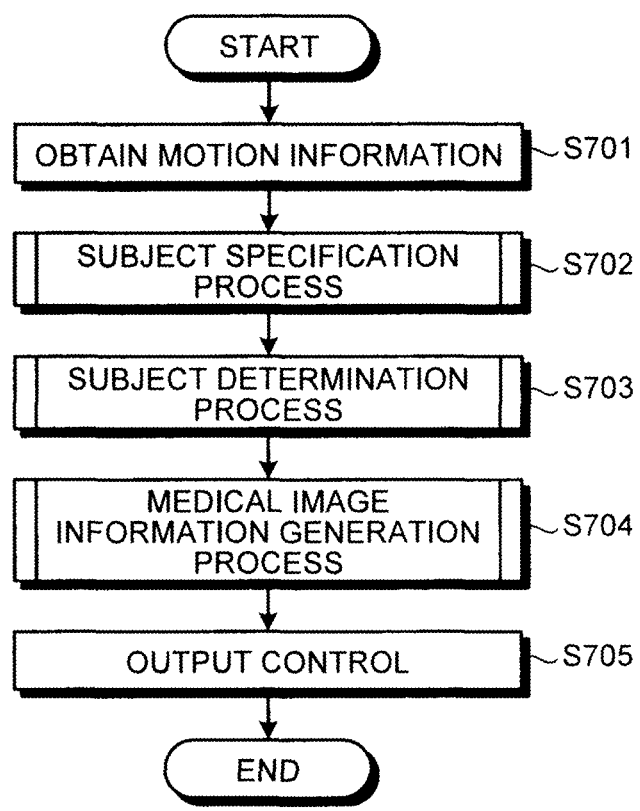
FIG. 47 is a flowchart illustrating procedures of processing performed by the motion information processing device according to the thirteenth embodiment.

FIG. 47 is a flowchart illustrating procedures of the processing performed by the motion information processing device 400 according to the thirteenth embodiment. As illustrated in FIG. 47, in the motion information processing device 400 according to the thirteenth embodiment, the obtaining circuitry 441 obtains motion information (step S701). For example, the obtaining circuitry 441 obtains color image information and skeleton information as the motion information.

Subsequently, the specification circuitry 442 performs a subject specification process (step S702). The subject specification process corresponds to the processing in steps S103 to S105 illustrated in FIG. 9. Specifically, the specification circuitry 442 specifies motion information of the subject by performing the subject specification process.

Subsequently, the first generation circuitry 443 and the determination circuitry 444 perform the subject determination process (step S703). The subject determination process corresponds to the processing in steps S303 and S304 illustrated in FIG. 27. Specifically, the first generation circuitry 443 generates evaluation information for evaluating rehabilitation from the motion information specified by the specification circuitry 442. The determination circuitry 444 then determines whether or not a person associated with motion information specified by the specification circuitry 442 is a subject of rehabilitation by using information indicating a feature of a rehab subject that is a subject of rehabilitation.

The second generation circuitry 445 then performs a medical image information generation process (step S704). The medical image information generation process corresponds to the processing in step S602 illustrated in FIG. 39. Specifically, the second generation circuitry 445 generates medical image information of the subject on the basis of at least one the skeleton information and color image information contained in time series in motion information determined to correspond to the subject by the determination circuitry.

Thereafter, the output control circuitry 446 performs output control (step S705). For example, the output control circuitry 446 outputs motion information for browsing containing skeleton information and medical image information in time series.

Note that the procedures of processing illustrated in FIG. 47 are not limited to the example described above. For example, although a case in which the motion information processing device 400 successively performs the subject specification process, the subject determination process, and the medical image information generation process as a series of processes after acquiring the motion information has been described in the example described above, the embodiment is not limited thereto. Specifically, the subject specification process, the subject determination process, and the medical image information generation process may be terminated when the output control circuitry 446 has stored necessary information as appropriate in the storage circuitry 430 after these processes have been performed or the obtaining circuitry 441 may obtain necessary information from the storage circuitry 430 as appropriate before performing these processes to start the processes.

Furthermore, for example, the subject specification process, the subject determination process, and the medical image information generation process need not necessarily be performed in the order described above. Specifically, these processes may be performed in the order of the medical image information generation process, the subject determination process, and the subject specification process.

Furthermore, for example, the subject specification process, the subject determination process, and the medical image information generation process need not necessarily be performed. Specifically, after performing the subject specification process, the motion information processing device 400 may perform the subject determination process or the medical image information generation process, and output information resulting from the process as appropriate. Alternatively, the motion information processing device 400 may sequentially perform the subject determination process and the medical image information generation process, and then output information resulting from the processes as appropriate.

As described above, the motion information processing device 400 according to the thirteenth embodiment performs the subject specification process, the subject determination process, and the medical image information generation process as a series of processes. As a result, the motion information processing device 400 according to the thirteenth embodiment can reliably determine motion information of a rehab subject, and further hide personal information of the rehab subject.

Other Embodiments

While the first to thirteenth embodiments have been described above, various different embodiments other than the embodiments described above can be employed.

Application to Service Providing Device

In the first to thirteenth embodiments described above, a case in which the motion information processing device specifies motion information (skeleton information) of a subject carrying out rehab has been described. The embodiment, however, is not limited thereto, and there may be cases where the processes are performed by a service providing device on a network, for example.

Figure 48:
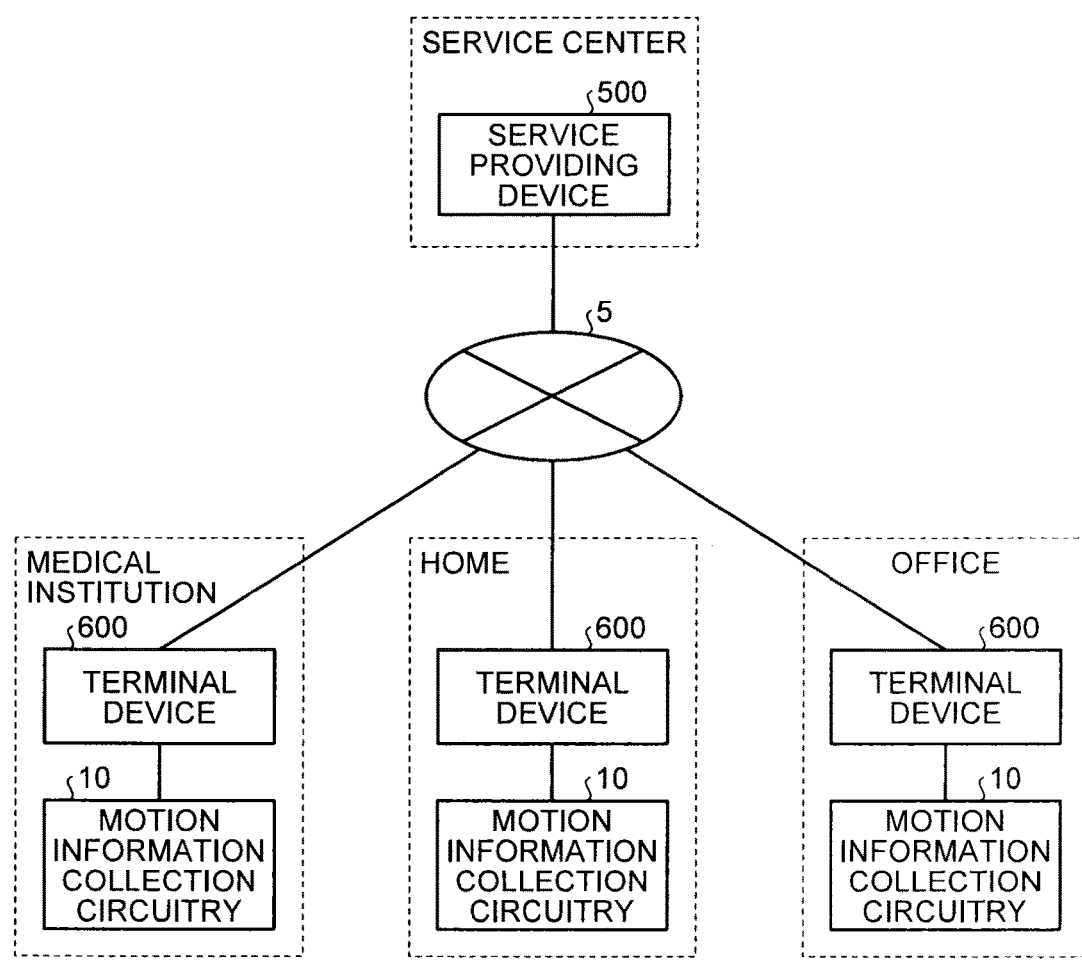
FIG. 48 is a diagram for explaining an example of application to a service providing device.

FIG. 48 is a diagram for explaining an example of application to a service providing device. As illustrated in FIG. 48, a service providing device 500 is installed in a service center, and connected to terminal devices 600 installed in a medical institution, at home, and in an office via a network 5, for example. The terminal devices 600 installed in the medical institution, at home, and in the office are each connected with a motion information collector 10. The terminal devices 600 each have a client function of using services provided by the service providing device 500.

For example, the service providing device 500 provides processes similar to those of the motion information processing device 100 described with reference to FIG. 4 as services to the terminal devices 600. Thus, the service providing device 500 has functional units similar to the obtaining circuitry 141 and the specification circuitry 142. The functional unit similar to the obtaining circuitry 141 obtains image information of a subject carrying out a predetermined motion and the surroundings of the subject. The functional unit similar to the specification circuitry 142 specifies motion information of the subject carrying out a predetermined motion on the basis of predetermined features in the image information obtained by the functional unit similar to the obtaining circuitry 141. For the network 5, any type of wired or wireless communication network can be used, such as the Internet and a wide area network (WAN).

Furthermore, the service providing device 500 has functions similar to those of the motion information processing device 200 described with reference to FIG. 19, and provides services to the terminal devices 600 by these functions, for example. Specifically, the service providing device 500 has functional units similar to the obtaining circuitry 241 and the determination circuitry 243. The functional unit similar to the obtaining circuitry 241 obtains motion information representing a motion of a person. The functional unit similar to the determination circuitry 243 determines whether or not the person associated with the motion information obtained by the functional unit similar to the obtaining circuitry 241 is a subject of rehabilitation by using information representing a feature of the subject. In view of the above, the service providing device 500 can determine whether or not a digitally recorded motion of a person is that of a subject of rehabilitation.

Furthermore, for example, the service providing device 500 has functions similar to those of the motion information processing device 300 described with reference to FIG. 36, and provides services to the terminal devices 600 by these functions. Specifically, the service providing device 500 has functional units similar to the obtaining circuitry 341, the generation circuitry 342, and the output control circuitry 343. The functional unit similar to the obtaining circuitry 341 obtains motion information containing skeleton information representing positions of joints contained in the skeleton of the test subject and photographed image information in which the test subject is photographed in time series. The functional unit similar to the generation circuitry 342 generates medical image information with which a motion of a test subject can be confirmed without containing personal information of the test subject on the basis of at least one of the skeleton information and the photographed image information.

For example, the service providing device 500 accepts upload of frames of the motion information to be processed from the terminal devices 600. The service providing device 500 then performs the processes described above to generate motion information for browsing. The service providing device 500 causes the motion information for browsing to be downloaded at the terminal devices 600. The terminal devices 600 then stores the downloaded motion information for browsing in the medical image archiving device 20.

Furthermore, for example, the service providing device 500 has functions similar to those of the motion information processing device 400 described with reference to FIG. 46, and provides services to the terminal devices 600 by these functions. Specifically, the service providing device 500 have functional units similar to the obtaining circuitry 441, the specification circuitry 442, the first generation circuitry 443, the determination circuitry 444, the second generation circuitry 445, and the output control circuitry 446. The functional unit similar to the obtaining circuitry 441 obtains image information of a subject carrying out a predetermined motion and the surroundings of the subject. The functional unit similar to the specification circuitry 442 specifies motion information of the subject carrying out a predetermined motion on the basis of predetermined features in the image information obtained by the functional unit similar to the obtaining circuitry 441. The functional unit similar to the determination circuitry 444 determines whether or not the person associated with the motion information specified by the functional unit similar to the specification circuitry 442 is a subject of rehabilitation by using information representing a feature of the subject. The functional unit similar to the second generation circuitry 445 generates medical image information with which a motion of a test subject can be confirmed without containing personal information of the test subject on the basis of at least one of the skeleton information and the photographed image information. The functional unit similar to the output control circuitry 446 then outputs motion information for browsing containing skeleton information and medical image information in time series.

Note that the configuration of the motion information processing device 100 according to the first to sixth embodiments is only an example, and the components thereof can be integrated or divided where appropriate. For example, the motion information storage circuitry 131 and the recognition information storage circuitry 132 can be integrated, or the specification circuitry 142 may be divided into calculation circuitry that calculates distances between joints and the like and comparison circuitry that compares calculated values with thresholds.

Furthermore, the configuration of the motion information processing device 200 according to the seventh to tenth embodiments is only an example, and the components thereof can be integrated or divided where appropriate. For example, the subject motion feature storage circuitry 232 and the caregiver motion feature storage circuitry 233 can be integrated, or the determination circuitry 243 can be divided into processing circuitry that extracts a condition for performing the determination process from the storage circuitry 230 and processing circuitry that performs determination by using the motion information.

Furthermore, the configuration of the motion information processing device 300 according to the eleventh and twelfth embodiments is only an example, and the components thereof can be integrated or divided where appropriate. For example, the obtaining circuitry 341 and the generation circuitry 342 can be integrated.

Furthermore, the functions of the obtaining circuitry 241 and the determination circuitry 243 described in the seventh to tenth embodiments can be implemented by software. For example, the functions of the obtaining circuitry 241 and the determination circuitry 243 are achieved by making a computer execute medical information processing programs defining the processes described as being performed by the obtaining circuitry 241 and the determination circuitry 243 in the embodiment described above. The medical information processing programs are stored in a hard disk, a semiconductor memory, or the like, and read and executed by a processor such as a CPU and a MPU, for example. Furthermore, the medical information processing program can be recorded distributed on a computer-readable recording medium such as a CD-ROM (Compact Disc-Read Only Memory), a MO (Magnetic Optical disk), or a DVD (Digital Versatile Disc).

Furthermore, the functions of the obtaining circuitry 341 and the generation circuitry 342 described in the eleventh and twelfth embodiments can be implemented by software. For example, the functions of the obtaining circuitry 341 and the generation circuitry 342 are achieved by making a computer execute medical information processing programs defining the processes described as being performed by the obtaining circuitry 341 and the generation circuitry 342 in the embodiment described above. The medical information processing programs are stored in a hard disk, a semiconductor memory, or the like, and read and executed by a processor such as a CPU and a MPU, for example. Furthermore, the medical information processing program can be recorded distributed on a computer-readable recording medium such as a CD-ROM (Compact Disc-Read Only Memory), a MO (Magnetic Optical disk), or a DVD (Digital Versatile Disc).

Note that rehabilitation rule information, recommended status of assistance, and the like presented in the first to ninth embodiments described above may be those provided by various organization in addition to those provided by The Japanese Orthopaedic Association and the like. For example, various regulations and rules provided by associations as follows may be employed: "International Society of Orthopaedic Surgery and Traumatology (SICOT)," "American Academy of Orthopaedic Surgeons (AAOS)," "European Orthopaedic Research Society (EORS)," "International Society of Physical and Rehabilitation Medicine (ISPRM)," and "American Academy of Physical Medicine and Rehabilitation (AAPM&R)." While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A motion information processing device for supporting a rehabilitation, the motion information processing device comprising:
obtaining circuitry configured to obtain image information of a subject carrying out a predetermined motion in the rehabilitation and surroundings of the subject, the image information including photographic image information and depth image information; and
specification circuitry configured to calculate positions of joints of the subject from the photographic image information and the depth image information included in the image information obtained by the obtaining circuitry, and to specify motion information of the subject carrying out the predetermined motion on the basis of a feature represented by the calculated positions of joints.

2. The motion information processing device according to claim 1, further comprising receiving circuitry configured to receive a specification operation for specifying a predetermined area in the image information, wherein
the specification circuitry is configured to specify motion information of a subject carrying out the predetermined motion within the area received by the receiving circuitry as the feature.

3. The motion information processing. device according to claim 1, wherein the specification circuitry is configured to extract subject information indicating the subject as the feature from the image information obtained by the obtaining circuitry, and specifies motion information of the subject carrying out the predetermined motion on the basis of the extracted subject information.

4. The motion information processing device according to claim 3, wherein the specification circuitry is configured to extract, as the subject information, at least one of information indicating a moving object contained in the image information, information representing a human body skeleton, and a set item set in advance for the subject, and specifies motion information of the subject carrying out the predetermined motion on the basis of the extracted subject information.

5. The motion information processing device according to claim 4, wherein the specification circuitry is configured to determine an object whose position changes in a three-dimensional space around the subject to be the moving object in image information obtained over time by the obtaining circuitry.

6. The motion information processing device according to claim 4, wherein the specification circuitry is configured to determine a set of joint points along a human body structure in information of joint points contained in the image information to be information representing the human body skeleton.

7. The motion information processing device according to claim 1, further comprising display control circuitry configured to perform control to display a display image obtained by superimposing the information indicating the subject on the image information at a position corresponding to the motion information specified by the specification circuitry.

8. The motion information processing device according to claim 1, further comprising:
determination circuitry configured to determine whether or not the subject associated with the motion information specified by the specification circuitry is a rehabilitation subject that receives rehabilitation by using information representing a feature of the rehabilitation subject; and
output control circuitry configured to output a determination result of the determination by the determination circuitry.

9. The motion information processing device according to claim 1, further comprising generation circuitry configured to generate medical image information allowing confirmation of a motion of the subject without containing personal information of the subject on the basis of at least one of information representing the human body skeleton of the subject, the information being contained in the motion information specified by the specification circuitry in time series, and image information in which the subject is photographed.

10. A motion information processing device comprising:
obtaining circuitry configured to obtain motion information representing a motion of a person;
determination circuitry configured to detect positons of joints of the person from the motion information and to determine whether or not a person associated with the motion information is a subject of rehabilitation based on whether or not a feature represented the detected positions of joints of the person corresponds to information representing a feature of motion of joints of the subject; and
output control circuitry configured to output a determination result of determination by the determination circuitry.

11. The motion information processing device according to claim 10, further comprising subject motion feature storage circuitry configured to store subject motion feature information representing a feature of a motion of the subject as information representing the feature of the subject, wherein
the determination circuitry is configured to refer to the subject motion feature storage circuitry and determines whether or not a person associated with the motion information obtained by the obtaining circuitry is the subject.

12. The motion information processing device according to claim 10, further comprising a caregiver motion feature storage circuitry configured to store caregiver motion feature information representing a feature of a motion of a caregiver assisting the subject, wherein
the determination circuitry is further configured to refer to the caregiver motion feature storage circuitry, and determines whether or not a person associated with the motion information obtained by the obtaining circuitry is the caregiver.

13. The motion information processing device according to claim 10, further comprising generation circuitry configured to generate evaluation information for evaluating the rehabilitation from the motion information obtained by the obtaining circuitry, wherein
the output control circuitry is configured to store the evaluation information generated by the generation circuitry and the determination result of determination by the determination circuitry in association with each other in a predetermined storage circuitry.

14. The motion information processing device according to claim 13, wherein the output control circuitry is configured to display a screen for confirmation of the determination result of determination by the determination circuitry on a predetermined display circuitry, and when the determination result is confirmed, stores the determination result and the evaluation information generated by the generation circuitry in association with each other in the predetermined storage circuitry.

15. The motion information processing device according to claim 10, further comprising a subject feature storage circuitry configured to store subject feature information representing a physical feature of the subject or an object accompanying the subject, wherein
the obtaining circuitry is further configured to obtain an image in which a person is photographed, and
the determination circuitry is further configured to refer to the subject feature storage circuitry, and determines whether or not a person in the image obtained by the obtaining circuitry is the subject.

16. The motion information processing device according to claim 15, wherein the physical feature of the subject is obtained from information recorded on an electronic medical record.

17. The motion information processing device according to claim 10, further comprising caregiver feature storage circuitry configured to store caregiver feature information representing a physical feature of the caregiver or an object accompanying the caregiver, wherein
the obtaining circuitry is further configured to obtain an image in which a person is photographed, and
the determination circuitry is further configured to refer to the caregiver feature storage circuitry, and determines whether or not a person in the image obtained by the obtaining circuitry is the caregiver.

18. The motion information processing device according to claim 10, further comprising an identification information storage circuitry configured to store identification information for identifying the caregiver, wherein
the obtaining circuitry is further configured to obtain a person image in which a person is photographed, and
the determination circuitry is further configured to extract the identification information from the person image obtained by the obtaining circuitry, and determines whether or not the extracted identification information corresponds to a person associated with identification information stored in the identification information storage circuitry.

19. The motion information processing device according to claim 10, further comprising generation circuitry configured to generate medical image information allowing confirmation of a motion of the subject without containing personal information of the subject on the basis of at least one of skeleton information representing positions of joints contained in a skeleton of the subject and photographed image information in which the subject is photographed, the skeleton information and the photographed image information being contained in the motion information determined to be the subject by the determination circuitry.

20. A motion information processing device comprising:
obtaining circuitry configured to obtain motion information containing skeleton information representing positions of joints contained in a skeleton of a test subject and photographed image information in which the test subject is photographed in time series; and
generation circuitry configured to generate medical image information allowing confirmation of a motion of the test object without containing personal information of the test subject on the basis of at least one of the skeleton information and the photographed image information.

21. The motion information processing device according to claim 20, wherein the generation circuitry is configured to generate, as the medical image information, image information allowing visual confirmation of the skeleton of the test subject by using positions of joints contained in the skeleton information.

22. The motion information processing device according to claim 20, wherein the generation circuitry is configured to generate, as the medical image information, image information in which at least a part containing a feature of the test subject contained in the photographed image information is hidden by using a position of a predetermined part contained in the skeleton information.

23. The motion information processing device according to claim 22, wherein the generation circuitry is further configured to generate, as the medical image information, image information in which at least a part of an image containing photographed object other than the test subject contained in the photographed image information is hidden by using the positions of joints contained in the skeleton information.

24. The motion information processing device according to claim 20, wherein the obtaining circuitry is configured to obtain the motion information further containing depth image information in time series in which pixels contained in a photographed range and depths of the pixels are associated, and
the generation circuitry is configured to generate, as the medical image information, image information representing an area of a test subject from depth image information at a time point of processing on the basis of the depth image information at the time point of processing and depth image information at a time point different from that of the depth image information.

25. The motion information processing device according to claim 20, wherein the generation circuitry is configured to generate, as the medical image information, image information containing a floor surface image representing a position of a floor in the photographed image.

* * * * *